US012668628B2

(12) United States Patent
Lin et al.

(10) Patent No.: US 12,668,628 B2
(45) Date of Patent: Jun. 30, 2026

(54) SIRP-GAMMA TARGETED AGENTS FOR USE IN THE TREATMENT OF CANCER

(71) Applicant: Wake Forest University Health Sciences, Winston-Salem, NC (US)

(72) Inventors: Hui-Kuan Lin, Winston-Salem, NC (US); Chuan Xu, Chengdu (CN); Xiu-Wu Bian, Chongqing (CN); Sarah Haigh Molina, Winston-Salem, NC (US); Mark Furth, Chapel Hill, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 2098 days.

(21) Appl. No.: 16/470,719

(22) PCT Filed: Dec. 19, 2017

(86) PCT No.: PCT/US2017/067257
§ 371 (c)(1),
(2) Date: Jun. 18, 2019

(87) PCT Pub. No.: WO2018/118887
PCT Pub. Date: Jun. 28, 2018

(65) Prior Publication Data
US 2023/0139592 A1 May 4, 2023

Related U.S. Application Data

(60) Provisional application No. 62/438,227, filed on Dec. 22, 2016.

(51) Int. Cl.
| | |
|---|---|
| *A61K 39/395* | (2006.01) |
| *A61K 31/713* | (2006.01) |
| *A61K 45/06* | (2006.01) |
| *A61P 35/00* | (2006.01) |
| *C07K 16/28* | (2006.01) |
| *C12N 15/113* | (2010.01) |
| *A61K 39/00* | (2006.01) |
| *C07K 14/705* | (2006.01) |

(52) U.S. Cl.
CPC ........ *C07K 16/2803* (2013.01); *A61K 31/713* (2013.01); *A61K 39/3955* (2013.01); *A61K 45/06* (2013.01); *A61P 35/00* (2018.01); *C12N 15/1138* (2013.01); *A61K 2039/505* (2013.01); *C07K 2317/76* (2013.01); *C12N 2310/122* (2013.01); *C12N 2310/531* (2013.01); *C12N 2320/30* (2013.01)

(58) Field of Classification Search
CPC ........... C07K 16/2803; C07K 2317/76; C07K 14/705; C07K 14/70503; C07K 14/70596; A61K 31/713; A61K 39/3955; A61K 45/06; A61K 2039/505; A61K 2039/57; A61K 39/39558; A61K 47/6807; A61K 31/7105; A61P 35/00; C12N 15/1138; C12N 2310/122; C12N 2310/531; C12N 2320/30; C12N 2310/141; C12N 2310/11
See application file for complete search history.

(56) References Cited

U.S. PATENT DOCUMENTS

| | | |
|---|---|---|
| 4,036,945 A | 7/1977 | Haber |
| 4,311,688 A | 1/1982 | Burchiel et al. |
| 4,342,566 A | 8/1982 | Theofilopoulos et al. |
| 4,676,980 A | 6/1987 | Segal et al. |
| 4,816,567 A | 3/1989 | Cabilly et al. |
| 4,897,255 A | 1/1990 | Fritzberg et al. |
| 5,103,098 A | 4/1992 | Fenyves |
| 5,109,397 A | 4/1992 | Gordon et al. |
| 5,208,581 A | 5/1993 | Collins |
| 5,210,421 A | 5/1993 | Gullberg et al. |
| 5,223,409 A | 6/1993 | Ladner et al. |
| 5,406,479 A | 4/1995 | Harman |
| 5,446,799 A | 8/1995 | Tuy |
| 5,600,145 A | 2/1997 | Plummer |
| 5,608,221 A | 3/1997 | Bertelsen et al. |
| 5,946,371 A | 8/1999 | Lai |
| 6,072,177 A | 6/2000 | McCroskey et al. |
| 6,115,446 A | 9/2000 | Pan |
| 6,151,377 A | 11/2000 | Nilsson |

(Continued)

FOREIGN PATENT DOCUMENTS

| | | |
|---|---|---|
| CN | 101880324 | 11/2010 |
| CN | 103665165 | 3/2014 |

(Continued)

OTHER PUBLICATIONS

Yipling Yang, Cancer immunotherapy: Harnessing the immune system to battle cancer, 2015, J Clin Invest;125(9):3335-3337 (Year: 2015).*
David E. Gerber, Targeted Therapies: A New Generation of Cancer Treatments, 2008, Am Fam Physician;77(3):311-9 (Year: 2008).*
Alberts B, et al, Molecular Biology of the Cell, 2002, Garland Science, 4th edition, Chapters 6,8,23 (Year: 2002).*
Burnett JC, et al. Current progress of siRNA/shRNA therapeutics in clinical trials. Biotechnol J. Sep. 2011;6(9):1130-46. doi: 10.1002/biot.201100054 (Year: 2011).*
Smaglo BG, Aldeghaither D, Weiner LM. The development of immunoconjugates for targeted cancer therapy. Nat Rev Clin Oncol. Nov. 2014;11(11):637-48. doi: 10.1038/nrclinonc.2014.159. Epub Sep. 30, 2014. PMID: 25265912; PMCID: PMC4700536. (Year: 2014).*

(Continued)

*Primary Examiner* — Bridget E Bunner
(74) *Attorney, Agent, or Firm* — Kilpatrick Townsend & Stockton LLP

(57) ABSTRACT

Provided are methods relating to SIRPgamma as a biomarker for cancer cells, and in particular of cancer stem cells and lung adenocarcinoma. Disclosed are also methods of treatment, which involve administering a SIRPgamma targeted agent to a subject with cancer, alone or with another cancer therapy. Methods for diagnosing cancer, identifying subjects with high SIRPgamma levels for treatment, and monitoring SIRPgamma expressing tumors are also provided.

13 Claims, 20 Drawing Sheets

Specification includes a Sequence Listing.

(56) References Cited

U.S. PATENT DOCUMENTS

| | | | |
|---|---|---|---|
| 8,562,997 | B2 | 10/2013 | Jaiswal et al. |
| 9,399,682 | B2 | 7/2016 | Jaiswal et al. |
| 2003/0027213 | A1 | 2/2003 | Zhu et al. |
| 2009/0181855 | A1 | 7/2009 | Vasquez et al. |
| 2010/0227774 | A1 | 9/2010 | Hua et al. |
| 2013/0197201 | A1 | 8/2013 | Vasquez et al. |
| 2013/0331297 | A1 | 12/2013 | Fan |
| 2014/0221250 | A1 | 8/2014 | Vasquez et al. |
| 2014/0377269 | A1 | 12/2014 | Mabry et al. |
| 2016/0176978 | A1 | 6/2016 | Jaiswal et al. |
| 2016/0340397 | A1* | 11/2016 | Ring ........................ A61P 35/00 |
| 2017/0151282 | A1 | 6/2017 | Discher et al. |

FOREIGN PATENT DOCUMENTS

| | | | | |
|---|---|---|---|---|
| WO | 9429348 | | 12/1994 | |
| WO | 9748723 | | 12/1997 | |
| WO | 9940940 | | 8/1999 | |
| WO | 0066159 | | 11/2000 | |
| WO | 0140307 | | 6/2001 | |
| WO | 0148020 | | 7/2001 | |
| WO | 2006110728 | | 10/2006 | |
| WO | 2009046541 | | 4/2009 | |
| WO | 2009091547 | | 7/2009 | |
| WO | 2009091601 | | 7/2009 | |
| WO | 2009131453 | | 10/2009 | |
| WO | WO-2010037134 | A2 * | 4/2010 | ........... C12N 5/0606 |
| WO | 2013056352 | | 4/2013 | |
| WO | 2015094995 | | 6/2015 | |
| WO | 2015105995 | | 7/2015 | |
| WO | 2015138600 | | 9/2015 | |
| WO | WO-2015138600 | A2 * | 9/2015 | ......... A61K 51/1027 |
| WO | WO-2015170108 | A1 * | 11/2015 | ........... C12Q 1/6883 |
| WO | 2016049276 | | 3/2016 | |
| WO | 2016057980 | A1 | 4/2016 | |
| WO | 2016063233 | | 4/2016 | |
| WO | 2016065329 | | 4/2016 | |
| WO | 2018149938 | | 8/2018 | |

OTHER PUBLICATIONS

Warram JM, de Boer E, Sorace AG, Chung TK, Kim H, Pleijhuis RG, van Dam GM, Rosenthal EL. Antibody-based imaging strategies for cancer. Cancer Metastasis Rev. Sep. 2014;33(2-3):809-22. doi: 10.1007/s10555-014-9505-5. PMID: 24913898; PMCID: PMC4116453. (Year: 2014).*

ClinicalTrials.gov NCT01363024 https://www.clinicaltrials.gov/study/NCT01363024?term=MFGR1877S&rank=2&tab=history&a=46 (Year: 2016).*

Humphrey RW et al. Opportunities and challenges in the development of experimental drug combinations for cancer. J Natl Cancer Inst. Aug. 17, 2011;103(16):1222-6. doi: 10.1093/jnci/djr246. Epub Jul. 15, 2011. PMID: 21765011; PMCID: PMC4415086. (Year: 2011).*

Trucillo, P. Drug Carriers: Classification, Administration, Release Profiles, and Industrial Approach. Processes 2021, 9, 470. https://doi.org/10.3390/pr9030470 (Year: 2021).*

Hoelder S, et al. Discovery of small molecule cancer drugs: successes, challenges and opportunities. Mol Oncol. Apr. 2012;6(2):155-76. doi: 10.1016/j.molonc.2012.02.004 (Year: 2012).*

Xiao YF, et al. Peptide-Based Treatment: A Promising Cancer Therapy. J Immunol Res. 2015;2015:761820. doi: 10.1155/2015/761820 (Year: 2015).*

Eramo A, Lotti F, Sette G, Pilozzi E, Biffoni M, Di Virgilio A, Conticello C, Ruco L, Peschle C, De Maria R. Identification and expansion of the tumorigenic lung cancer stem cell population. Cell Death Differ. Mar. 2008;15(3):504-14. doi: 10.1038/sj.cdd.4402283. Epub Nov. 30, 2007. PMID: 18049477. (Year: 2007).*

Cabrera MC, Hollingsworth RE, Hurt EM. Cancer stem cell plasticity and tumor hierarchy. World J Stem Cells. Jan. 26, 2015;7(1):27-36. doi: 10.4252/wjsc.v7.i1.27. PMID: 25621103; PMCID: PMC4300934. (Year: 2015).*

Parvez A, Choudhary F, Mudgal P, Khan R, Qureshi KA, Farooqi H, Aspatwar A. PD-1 and PD-L1: architects of immune symphony and immunotherapy breakthroughs in cancer treatment. Front Immunol. Dec. 1, 2023;14:1296341. doi: 10.3389/fimmu.2023.1296341. PMID: 38106415; PMCID: PMC10722272. (Year: 2023).*

Jutten B, Rouschop KM. EGFR signaling and autophagy dependence for growth, survival, and therapy resistance. Cell Cycle. 2014; 13(1):42-51. doi: 10.4161/cc.27518. Epub Dec. 13, 2013. PMID: 24335351; PMCID: PMC3925733. (Year: 2013).*

Abhold EL, et al. EGFR kinase promotes acquisition of stem cell-like properties: a potential therapeutic target in head and neck squamous cell carcinoma stem cells. PLoS One. 2012;7(2):e32459. doi: 10.1371/journal.pone.0032459. Epub Feb. 27, 2012. PMID: 22384257; PMCID: PMC3288103. (Year: 2012).*

Clark JD, Flanagan ME, Telliez JB. Discovery and development of Janus kinase (JAK) inhibitors for inflammatory diseases. J Med Chem. Jun. 26, 2014;57(12):5023-38. doi: 10.1021/jm401490p. Epub Jan. 23, 2014. PMID: 24417533. (Year: 2014).*

Guido RV, Oliva G, Andricopulo AD. Virtual screening and its integration with modern drug design technologies. Curr Med Chem. 2008;15(1):37-46. doi: 10.2174/092986708783330683. PMID: 18220761. (Year: 2008).*

Dallas DC, Guerrero A, Parker EA, Robinson RC, Gan J, German JB, Barile D, Lebrilla CB. Current peptidomics: applications, purification, identification, quantification, and functional analysis. Proteomics. Mar. 2015;15(5-6):1026-38. doi: 10.1002/pmic.201400310. Epub Jan. 21, 2015. PMID: 25429922. (Year: 2015).*

Wang SH, Yu J. Structure-based design for binding peptides in anti-cancer therapy. Biomaterials. Feb. 2018;156:1-15. doi: 10.1016/j.biomaterials.2017.11.024. PMID: 29182932. (Year: 2018).*

Luo et al. SIRPG expression positively associates with an inflamed tumor microenvironment and response to PD-1 blockade. Cancer Immunol Immunother 73: 147, 2024 (16 total pages).*

Xu et al. SIRPγ-expressing cancer stem-like cells promote immune escape of lung cancer via Hippo signaling. J Clin Invest 132(5): e141797, 2022 (20 total pages).*

Iyer et al. ELA026, a monoclonal antibody targeting SIRP-expressing myeloid cells and T lymphocytes, demonstrates broad anti-tumor activity in patients with lymphoma. Hematol Oncol 43(Suppl 3): #445, 2026.*

Abrahmsen et al., "Engineering Subtilisin and Its Substrates for Efficient Ligation of Peptide Bonds in Aqueous Solution", Biochemistry, vol. 30, No. 17, Apr. 1991, pp. 4151-4159.

Baggiolini et al., "Interleukin-8, A Chemotactic and Inflammatory Cytokine", Febs Letters, vol. 307, No. 1, Jul. 27, 1992, pp. 97-101.

Barclay et al., "The Interaction Between Signal Regulatory Protein Alpha (SIRPα) and Cd47: Structure, Function, and Therapeutic Target", Annual Review of Immunology, vol. 32, No. 1, Mar. 2014, pp. 25-50.

Barclay et al., "The SIRP Family of Receptors and Immune Regulation", Nature Reviews Immunology, vol. 6, Jun. 2006, pp. 457-464.

Berkner et al., "Abundant Expression of Polyomavirus Middle T Antigen and Dihydrofolate Reductase in an Adenovirus Recombinant", Journal of Virology, vol. 61, No. 4, Apr. 1987, pp. 1213-1220.

Brooke et al., "Human Lymphocytes Interact Directly with Cd47 Through a Novel Member of the Signal Regulatory Protein (SIRP) Family", Journal of Immunology, vol. 173, No. 4, Aug. 15, 2004, pp. 2562-2570.

Cheng et al., "Functional Genomics Screen Identifies YAP1 as a Key Determinant to Enhance Treatment Sensitivity in Lung Cancer Cells", Oncotarget, vol. 7, No. 20, Dec. 22, 2015, pp. 28976-28988.

Cho et al., "An Unnatural Biopolymer", Science, vol. 261, No. 5126, Sep. 3, 1993, pp. 1303-1305.

Clark-Lewis et al., "Chemical Synthesis, Purification, and Characterization of Two Inflammatory Proteins, Neutrophil Activating Peptide 1 (Interleukin-8) and Neutrophil Activating Peptide 2", Biochemistry, vol. 30, No. 12, Mar. 26, 1991, pp. 3128-3135.

Contag et al., "Use of Reporter Genes for Optical Measurements of Neoplastic Disease in Vivo1", Neoplasia, vol. 2, No. 1-2, Jan.-Apr. 2000, pp. 41-52.

Cull et al., "Screening for Receptor Ligands Using Large Libraries of Peptides Linked to the C Terminus of the lac Repressor",

(56) References Cited

OTHER PUBLICATIONS

Proceedings of the National Academy of Sciences of the United States of America, vol. 89, No. 5, Mar. 1992, pp. 1865-1869.

Cwirla et al., "Peptides on Phage: A Vast Library of Peptides for Identifying Ligands", Proceedings of the National Academy of Sciences of the United States of America, vol. 87, No. 16, Aug. 1990, pp. 6378-6282.

Davidson et al., "Overproduction of Polyomavirus Middle T Antigen in Mammalian Cells Through the Use of an Adenovirus Vector", Journal of Virology, vol. 61, No. 4, Apr. 1987, pp. 1226-1239.

Dewitt et al., ""Diversomers": An Approach to Nonpeptide, Nonoligomeric Chemical Diversity", Proceedings of the National Academy of Sciences, vol. 90, No. 15, Aug. 1993, pp. 6909-6913.

Erb et al., "Recursive Deconvolution of Combinatorial Chemical Libraries", Proceedings of the National Academy of Sciences of the United States of America, vol. 91, No. 24, Nov. 1994, pp. 11422-11426.

Fodor et al., "Multiplexed Biochemical Assays With Biological Chips", Nature, vol. 364, Aug. 5, 1993, pp. 555-556.

Fotherby, "Bioavailability of Orally Administered Sex Steroids Used in Oral Contraception and Hormone Replacement Therapy", Contraception, vol. 54, Issue 2, Aug. 1996, pp. 59-69.

Garcea et al., "Virus-like Particles as Vaccines and Vessels for the Delivery of Small Molecules", Current Opinion in Biotechnology, vol. 15, No. 6, Dec. 15, 2004, pp. 513-517.

Haj-Ahmad et al., "Development of a Helper-Independent Human Adenovirus Vector and Its Use in the Transfer of the Herpes Simplex Virus Thymidine Kinase Gene", Journal of Virology, vol. 57, No. 1, Jan. 1986, pp. 267-274.

Harlow et al., "Antibodies: A Laboratory Manual", Cold Spring Harbor Laboratory Press, 1988, 105 pages.

Hoogenboom et al., "By-Passing Immunisation: Human Antibodies From Synthetic Repertoires of Germline Vh Gene Segments Rearranged in Vitro", Journal of Molecular Biology, vol. 227, No. 2, Sep. 20, 1992, pp. 381-388.

Hsu et al., "YAP promotes erlotinib resistance in human non-small cell lung cancer cells", Oncotarget, vol. 7, 32, 2016, pp. 51922-51933.

Ichigotani et al., "Molecular Cloning of a Novel Human Gene (SIRP-B2) which Encodes a New Member of the SIRP/SHPS-1 Protein Family", Journal of Human Genetics, vol. 45, Feb. 2000, pp. 378-382.

Jakobovits et al., "Analysis of Homozygous Mutant Chimeric Mice: Deletion of the Immunoglobulin Heavy-Chain Joining Region Blocks B-cell Development and Antibody Production", Proceedings of the National Academy of Sciences of the United States of America, vol. 90, No. 6, Mar. 15, 1993, pp. 2551-2555.

Jakobovits et al., "Germ-Line Transmission and Expression of a Human-Derived Yeast Artificial Chromosome", Nature, vol. 362, Mar. 18, 1993, pp. 255-258.

Johnson et al., "Permeation of Steroids Through Human Skin", Journal of Pharmaceutical Sciences, vol. 84, No. 9, Sep. 1995, pp. 1144-1146.

Jones et al., "Replacing the Complementarity-Determining Regions in a Human Antibody with those from a Mouse", Nature, vol. 321, No. 6069, May 29-Jun. 4, 1986, pp. 522-525.

Kohler et al., "Continuous Cultures of Fused Cells Secreting Antibody of Predefined Specificity", Nature, vol. 256, No. 5517, Aug. 7, 1975, pp. 495-497.

Lam et al., "A New Type of Synthetic Peptide Library for Identifying Ligand-Binding Activity", Nature, vol. 354, Nov. 7, 1991, pp. 82-84.

Lee et al., "Hippo pathway effector YAP inhibition restores the sensitivity of EGFR-TKI in lung adenocarcinoma having primary or acquired EGFR-TKI resistance", Biochemical and Biophysical Research Communications, vol. 474, No. 1, 2016, pp. 154-160.

Lonberg et al., "Human Antibodies from Transgenic Mice", International Reviews of Immunology, vol. 13, No. 1, 1995, pp. 65-93.

Marks et al., "By-Passing Immunization: Human Antibodies From V-Gene Libraries Displayed on Phage", Journal of Molecular Biology, vol. 222, No. 3, Dec. 5, 1991, pp. 581-597.

Massie et al., "Construction of a Helper-Free Recombinant Adenovirus that Expresses Polyomavirus Large T Antigen", Molecular and Cellular Biology, vol. 6, No. 8, Aug. 1986, pp. 2872-2883.

Nettleship et al., "Crystal Structure of Signal Regulatory Protein Gamma (SIRPy) in Complex with an Antibody Fab Fragment", BMC Structural Biology, vol. 13, Jul. 2013, pp. 1-8.

Patel et al., "Non-Small Cell Lung Cancer Disease Coverage", Data Monitor Healthcare, Aug. 10, 2016, 512 pages.

Piccio et al., "Adhesion of Human T Cells to Antigen-Presenting Cells Through SIRP132-CD47 Interaction Costimulates T-Cell Proliferation", Blood, vol. 105, No. 6, Mar. 15, 2005, pp. 2421-2427.

Riechmann et al., "Reshaping Human Antibodies for Therapy", Nature, vol. 332, No. 6162, Mar. 1988, pp. 323-327.

Stefanidakis et al., "Endothelial Cd47 Interaction with SIRPy Is Required for Human T-Cell Transendothelial Migration Under Shear Flow Conditions in Vitro", Blood, vol. 112, No. 4, Aug. 15, 2008, pp. 1280-1289.

Sun et al., "Cytoplasmic YAP expression is associated with prolonged survival in patients with lung adenocarcinomas and epidermal growth factor receptor tyrosine kinase inhibitor treatment", Annals of Surgical Oncology, vol. 21, 2014, pp. S610-S618.

Tuschl et al., "The siRNA User Guide", May 6, 2004,.

Xu et al., "B-Catenin/POU5F1/SOX2 Transcription Factor Complex Mediates IGF-I Receptor Signaling and Predicts Poor Prognosis in Lung Adenocarcinoma", Cancer Research, vol. 73, No. 10, May 15, 2013, pp. 3181-3189.

Zoller et al., "Oligonucleotide-Directed Mutagenesis Using M13-Derived Vectors: An Efficient and General Procedure for the Production of Point Mutations in any Fragment of DNA", Nucleic Acids Research, vol. 10, No. 20, Oct. 25, 1982, pp. 6487-6500.

Zuckermann et al., "Discovery of Nanomolar Ligands for 7-Transmembrane G-Protein-Coupled Receptors from a Diverse N-(Substituted)Glycine Peptoid Library", Journal of Medicinal Chemistry, vol. 37, No. 17, Aug. 1994, pp. 2678-2685.

Dragu et al., "Therapies Targeting Cancer Stem Cells: Current Trends and Future Challenges", World Journal of Stem Cells, vol. 7, No. 9, Oct. 26, 2015, 17 pages.

International Search Report and Written Opinion mailed Mar. 4, 2018 for PCT Appl. No. PCT/US2017/067257.

Deonarain, M.P. et al., "Antibodies targeting cancer stem cells", mAbs, vol. 1, No. 1, 2009, pp. 12-26.

Dragu, D.L. et al., "Therapies targeting cancer stem cells: Current trends and future challenges," World Journal of Stem Cells, vol. 7, No. 9, Oct. 26, 2015, pp. 1185-1201.

Naujokat, C, "Targeting Human Cancer Stem Cells with Monoclonal Antibodies," Journal of Clinical and Cellular Immunology, vol. S5, 007, 2012.

Hong, K.P. et al., "Therapeutic affect of anti-CEACAM6 monoclonal antibody against lung adenocarcinoma by enhancing anoikis sensitivity", Biomaterials, vol. 67, 2015, pp. 32-41.

McCracken, M.N., "Molecular Pathways: Activating T Cells after Cancer Cell Phagocytosis from Blockade of CD47 "Don't Eat Me" Signals," Clinical Cancer Research, vol. 21, No. 16, Jun. 26, 2015, pp. 3597-3601.

Llu, J. et al., "Pre-Clinical Development of a Humanized Anti-CD47 Antibody with Anti-Cancer Therapeutic Potential," PLOS One, vol. 10, No. 9, Sep. 21, 2015, pp. 1-23.

Yanagita, T. et al., "Anti-SIRPa antibodies as a potential new tool for cancer immunotherapy", JCI INSIGHT, vol. 2, No. 1, Dec. 1, 2017, pp. 1-15.

* cited by examiner

FIG. 3A                                          FIG. 3B
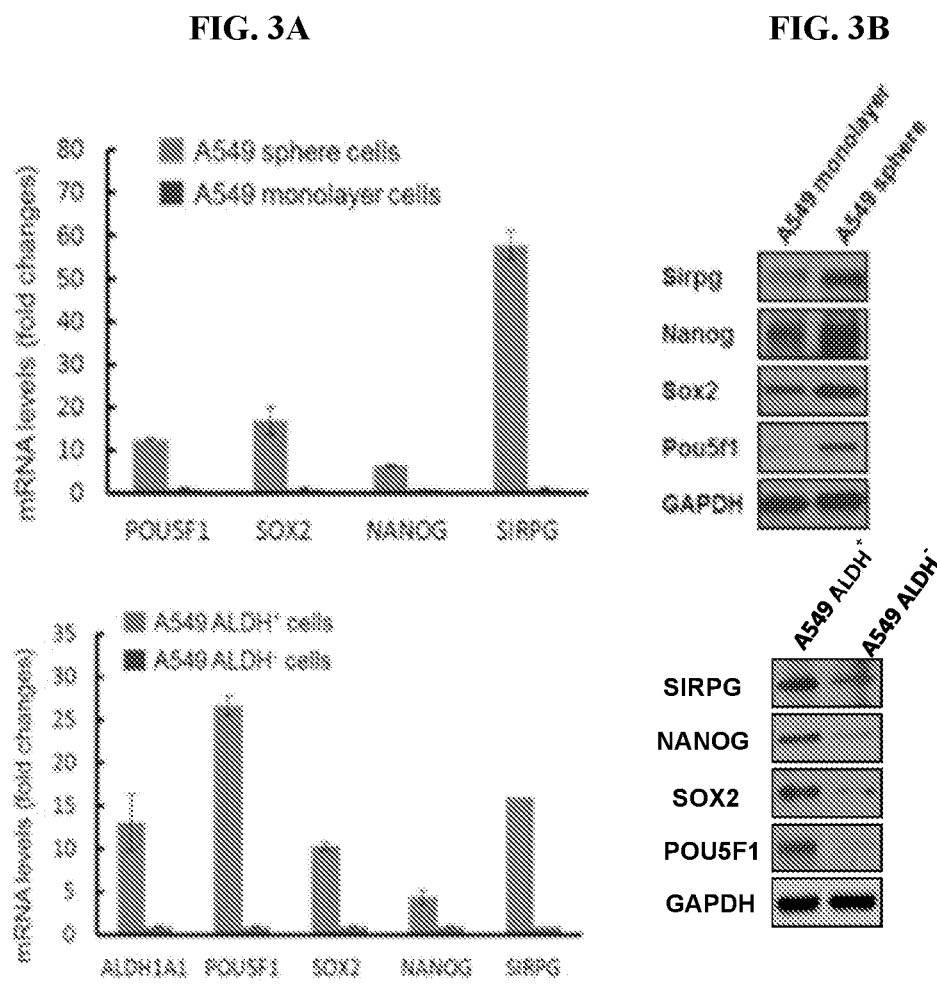
FIG. 3C                                          FIG. 3D

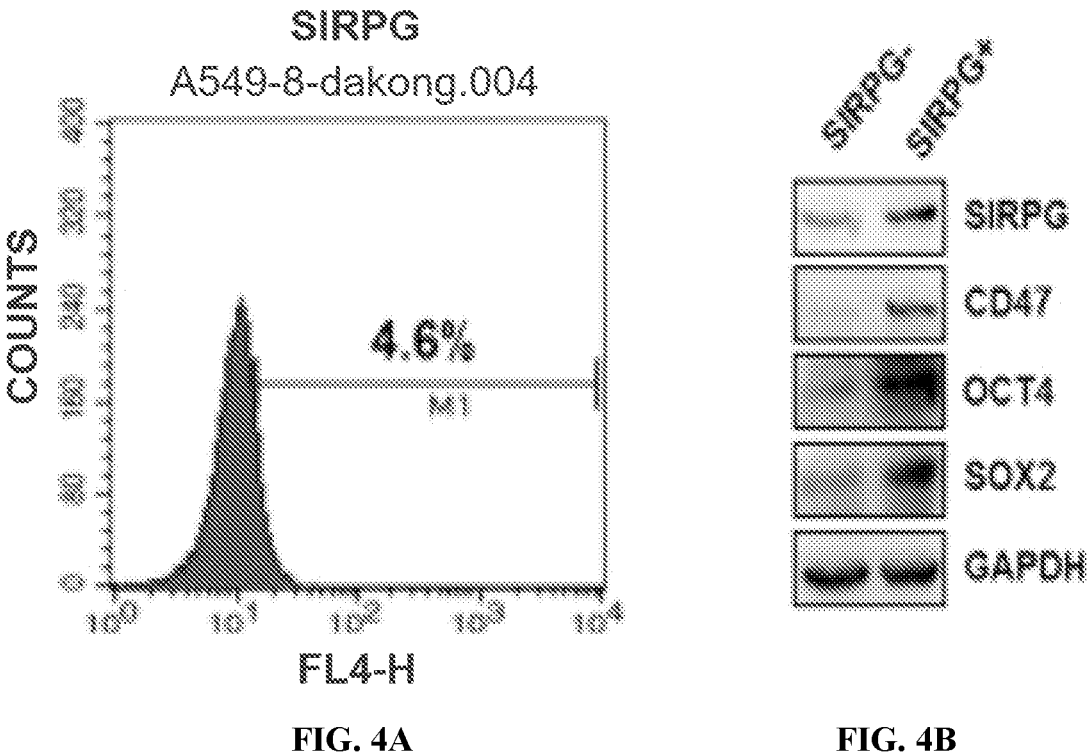
FIG. 4A                    FIG. 4B
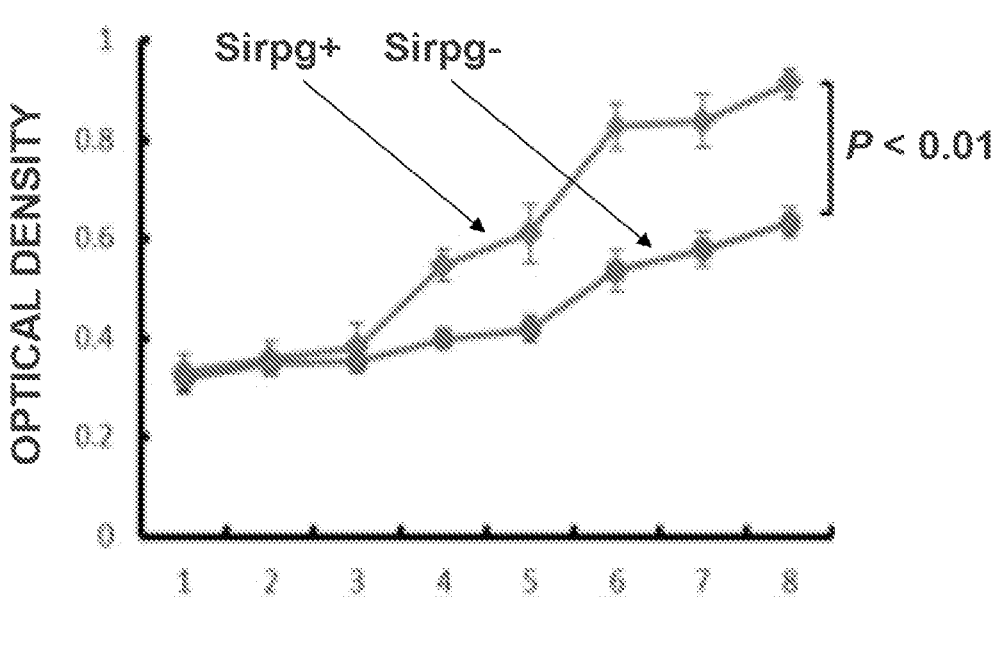
FIG. 4C

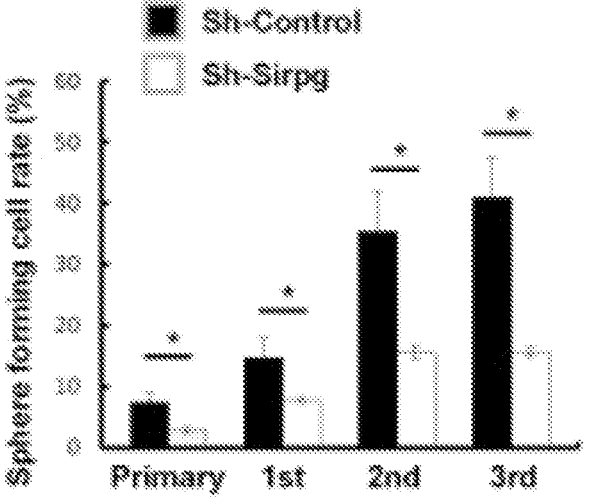
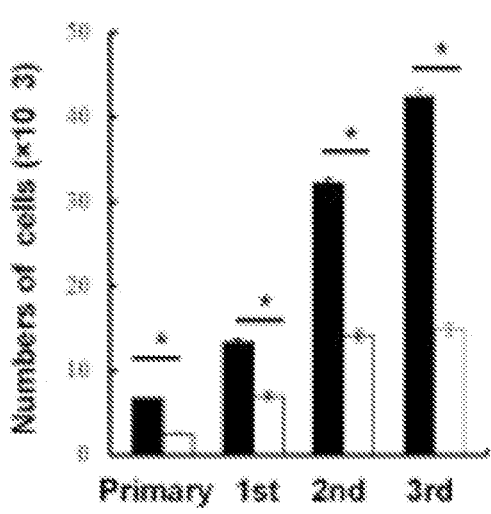
FIG. 5A                                                    FIG. 5B
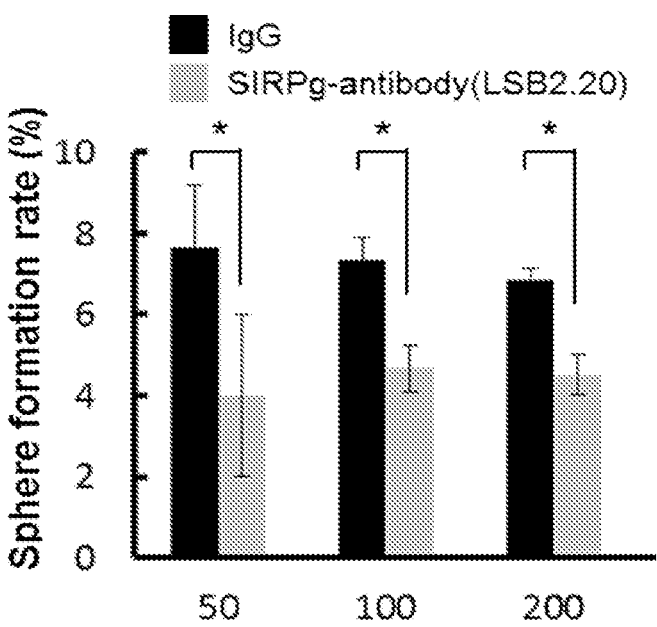
FIG. 6

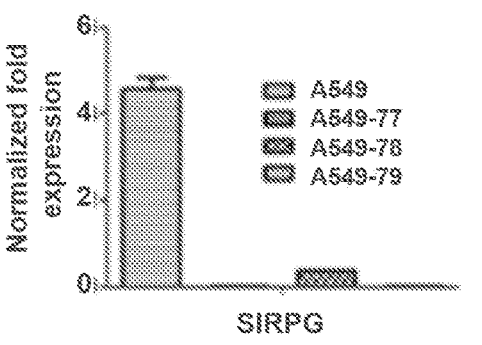
FIG. 11A
FIG. 11B
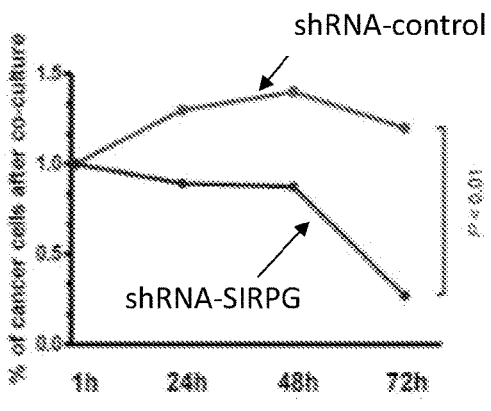
FIG. 12A
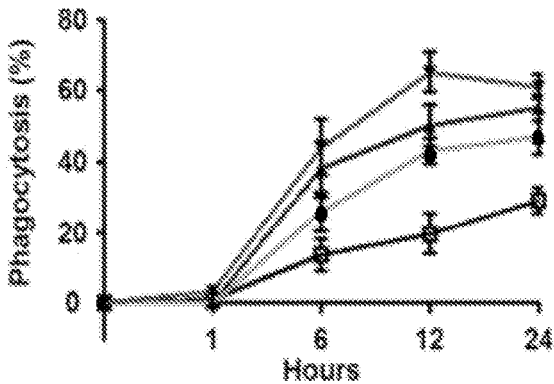
A549 Cells+RAW264.7+IgG
A549 Cells+RAW264.7+Anti-CD47
A549 Cells+RAW264.7+Anti-SIRPG
A549 Cells+RAW264.7+Anti-CD47+Anti-SIRPG
FIG. 12B

Cell number/well

FIG. 17A                    FIG. 17B                    FIG. 17C
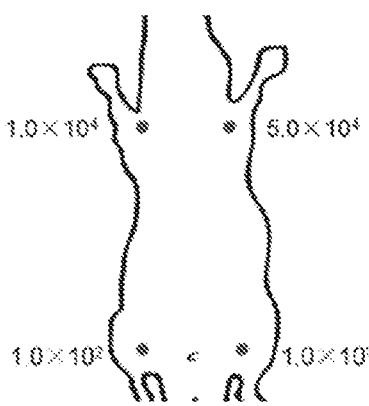
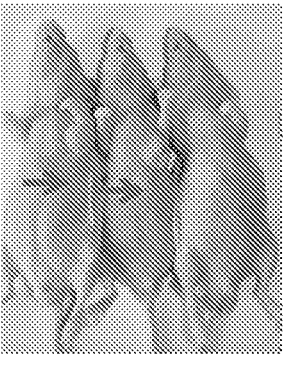
SIRPG<sup>high</sup> A549 cells
5 Weeks
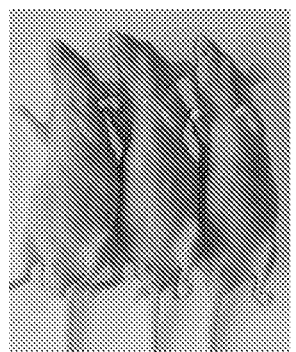
SIRPG<sup>low</sup>-A549 cells
5 Weeks
FIG. 17D
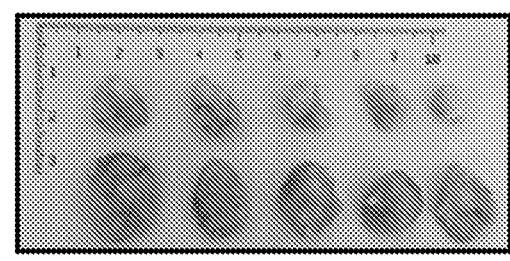

FIG. 19A
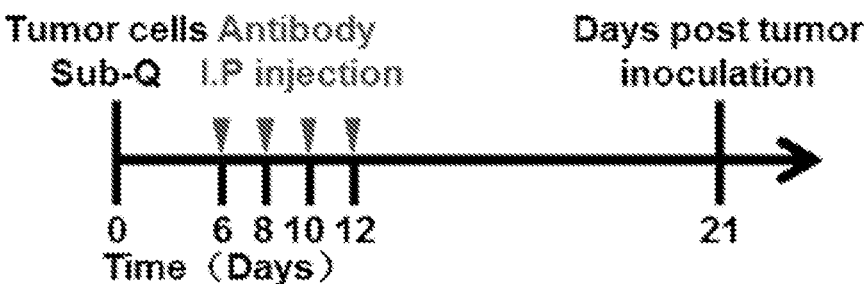
FIG. 19B                                                    FIG. 19C
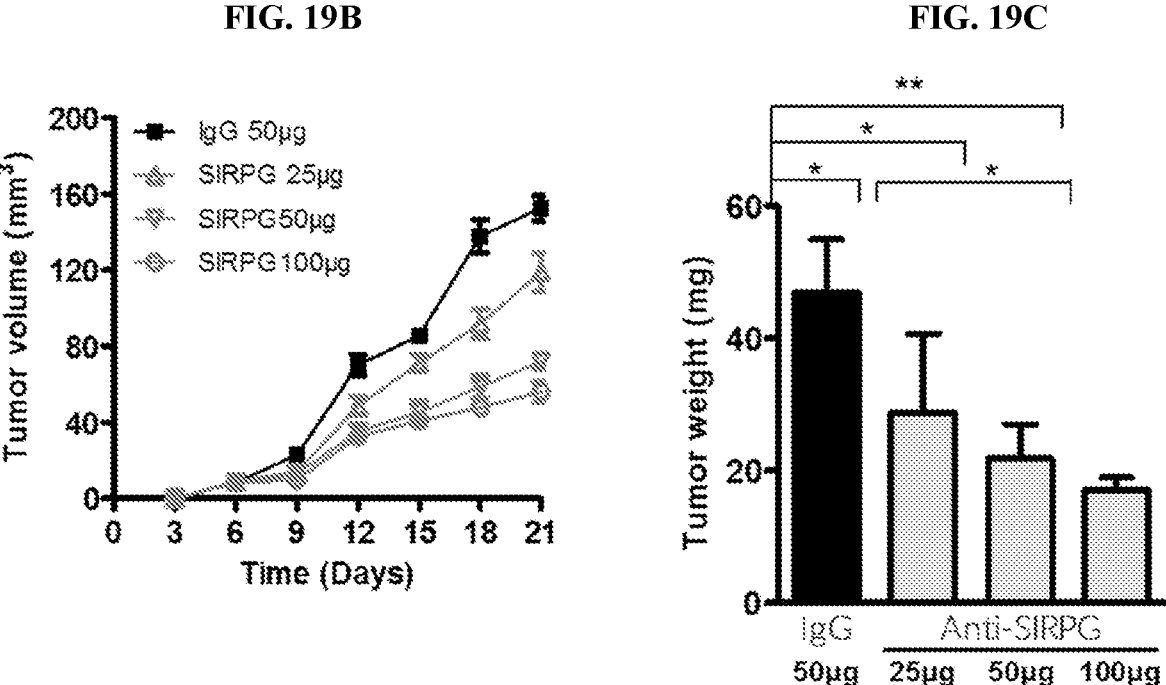

SIRP-GAMMA TARGETED AGENTS FOR USE IN THE TREATMENT OF CANCER

CROSS-REFERENCE TO RELATED PATENT APPLICATIONS

This application is a U.S. National Phase under 35 U.S.C. § 371 of International Patent Application No. PCT/US2017/067257, filed Dec. 19, 2017, which claims the benefit of and priority to U.S. Provisional Patent Application No. 62/438,227, filed on Dec. 22, 2016, the entire content of which is incorporated herein by this reference as if fully set forth herein.

SEQUENCE LISTING

The official copy of the sequence listing is submitted electronically via EFS-Web as an ASCII formatted sequence listing with a file named 1143062_SEQLISTING.txt, created on Sep. 3, 2019, and having a size of 3,319 bytes. The sequence listing contained in this ASCII formatted document is part of the specification and is herein incorporated by reference in its entirety.

BACKGROUND

The initiation and perpetuation of cancer depends on several aberrant processes including cell invasion and migration, proliferation, inhibition of growth suppression, angiogenesis, and survival by evading normal cell death processes such as apoptosis and necrosis. While under normal physiological conditions damaged/aberrant cells are identified and eliminated by cells of the immune system, many cancers have evolved diverse mechanisms to evade such regulation.

Cancer stem cells (CSC), also referred to as tumor-initiating cells, are believed essential for the ongoing, long-term growth of cancers, as they uniquely possess the critical property of self-renewal. CSC also are generally considered the cells responsible for initiating tumor metastases. Moreover, CSC display broadly elevated resistance to standard cancer treatments such as chemotherapy and radiation and may also play key roles in conditioning an inflammatory tumor microenvironment and evading control by the immune system.

The presence of CSC has been described in a wide variety of cancers, both leukemias and solid tumors. The CSC represent a subset of tumor cells that are believed to be crucial for the sustained growth and metastatic capacity of most malignant disease. The CSC may be defined most rigorously by their ability to form tumors efficiently when transplanted into recipient animals. For human tumors the assay can be carried out using severely immune-deficient mice that lack both innate and adaptive immune cells and functionality. Enriched CSC form transplanted tumors much more efficiently, that is at far lower numbers of transplanted cells, than the bulk population of tumor cells. In principle, a single CSC should suffice to initiate a new tumor. Depending on the cancer, the frequency of CSC may range from a few percent to fewer than one per 100,000. Remarkably, even many tumor-derived cell lines that have been maintained in laboratory culture for decades retain a lineage hierarchy. That is, they contain a population of relatively rare CSC that sustain the "immortality" of the cell line and its ability to form tumors in animals. The remainder of the cells in cell line cultures are more differentiated than the CSC, having lost the capacity for self-renewal that is a central, defining feature of stem cells, and in some cases expressing specialized functions of the normal tissue type in which the cancer arose.

Therapies targeted to CSC would thus have several advantages for treating both early stage and metastatic cancers by reducing tumor growth and/or increasing sensitivity to existing cancer therapies.

BRIEF SUMMARY

Aspects of the present invention encompass methods relating to SIRPgamma as a cancer stem cell marker for therapeutic, diagnostic, and prognostic purposes. Provided herein are methods to treat, inhibit, or ameliorate cancer in a subject. The methods include administering to a subject an effective amount of one or more SIRPgamma targeted agents described herein. Also, provided are prognostic and diagnostic methods for cancer based on detection and/or quantitation of SIRPgamma using a SIRPgamma targeted agent.

In one aspect, provided is a method of treating a subject with cancer, the method including the step of administering to the patient a pharmaceutically effective amount of a composition comprising a SIRPgamma targeted agent. The SIRPgamma targeted agent may work at the gene, transcript, or protein level. The SIRPgamma targeted agent may be a SIRPgamma targeted antibody, a SIRPgamma targeted peptide, a SIRPgamma targeted small molecule, a SIRPgamma targeted RNA molecule, or a combination thereof. In some instances, the SIRPgamma targeted agent may be conjugated to a therapeutic agent. In some instances, the method further includes administering a second form of cancer therapy to the subject. In some embodiments, the second form of cancer therapy comprises an epidermal growth factor receptor (EGFR) inhibitor. In some embodiments, the EGFR inhibitor is a receptor tyrosine kinase inhibitor.

In another aspect, provided is a method of inhibiting expression of the SIRPgamma protein in a cancer cell, the method including the steps of contacting a cell expressing the SIRPgamma gene with a synthetic SIRPgamma targeted RNA molecule.

In another aspect, provided is a method of imaging a tumor in a subject with a SIRPgamma expressing cancer, the method including the steps of: (a) administering to the subject a SIRPgamma targeted agent conjugated to an imaging label, and (b) detecting the imaging label in the subject to obtain an image of the tumor.

In another aspect, provided is a method of monitoring response of a subject with a SIRPgamma expressing cancer to cancer therapy, the method including the steps of: (a) administering to the subject a SIRPgamma targeted agent conjugated to an imaging label at a first time point prior to the subject before the subject receives cancer therapy, (b) detecting the imaging label in the subject to obtain a first image of the tumor; (c) administering to the subject a SIRPgamma targeted agent conjugated to an imaging label at a second time point after the subject receives cancer therapy, (d) detecting the imaging label in the subject to obtain a second image of the tumor; and (e) comparing the first image to the second image to determine whether a change in tumor size has occurred. In some instances, steps (c) to (e) may be repeated at a third time point after the subject receives cancer therapy.

In another aspect, provided is a method of assessing responsiveness of a subject with cancer to a SIRPgamma targeted agent including the steps of: (a) measuring in a tumor sample from a subject the amount of SIRPgamma; (b)

determining if a subject has a cancer characterized as having a high level of SIRPgamma expression; and (c) indicating that the subject is more likely to respond to the SIRPgamma targeted agent if the subject's cancer is characterized as having a high level of SIRPgamma expression or that the subject is less likely to respond to the SIRPgamma targeted agent if the subject's cancer is characterized as having a low level of SIRPgamma expression.

In another aspect, provided herein is a method of assessing the eligibility of a subject for a clinical trial of SIRP-gamma targeted therapy including the steps of: (a) measuring in a tumor sample from a subject the amount of SIRPgamma; (b) determining if a subject has a cancer characterized as having a high level of SIRPgamma expression, i.e., above a predetermined threshold; and (c) indicating that the subject eligible for a clinical trial of SIRPgamma targeted therapy if the subject's cancer is characterized as having a high level of SIRPgamma expression or that the subject is ineligible for the SIRPgamma targeted therapy if the subject's cancer is characterized as having a low level of SIRPgamma expression.

The above described features, and many other features and attendant advantages of the present invention, will become apparent and further understood by reference to the following detailed description when considered in conjunction with the accompanying drawings.

BRIEF DESCRIPTION OF THE DRAWINGS

These figures are intended to be illustrative, not limiting. Although the aspects of the disclosure are generally described in the context of these figures, it should be understood that it is not intended to limit the scope of the disclosure to these particular aspects.

FIG. 2A shows immunohistochemistry analysis for SIRPgamma (labeled as Sirpg) in two representative human lung adenocarcinoma tissue samples. Left: a tumor classified as SIRPgamma$^{high}$ (high expression); Right: a tumor classified as SIRPgamma$^{low}$ (low expression). FIG. 2B depicts a summary of the intensity of SIRPgamma expression (labeled as SIRPG) in tumor and adjacent normal tissue in tissue biopsies from 35 cases of lung cancer cohort (relative scoring scale of 1-15). Adenocarcinomas showed significantly elevated expression relative to adjacent normal tissue (p<0.001). FIG. 2C shows that high expression of SIRPgamma (SIRPgamma$^{high}$, labeled HIGH) in lung adenocarcinoma correlates with significantly poorer disease specific survival, shown in months after diagnosis (x axis) (p<0.05).

FIG. 3A-3D show cancer stem cells (CSC) of human lung adenocarcinoma cell lines express elevated levels of SIRP-gamma according to some aspects of this disclosure. Cells of human lung adenocarcinoma cell line AS49 were grown in standard monolayer culture or in spheroid cultures that strongly enrich for CSC. mRNA analysis is shown in FIG. 3A and protein analysis (Western immunoblot) is shown in FIG. 3B. In FIG. 3A, for each mRNA assessed, the bar on the left corresponds to the spheroid culture (A549 sphere cells) and the bar on the right corresponds to the monolayer culture (A549 monolayer cells). Cells were assayed for expression of SIRPgamma (labeled SIRPG) and three transcription factors (POU5F1/OCT4; SOX2; NANOG) associated with early embryonic cells and with various normal adult stem cells and CSC. The results show dramatically enhanced expression of the four genes in the CSC-enriched spheres. In a separate experiment, A549 cells grown in monolayer culture were incubated with fluorescent ALDH substrate and separated by FACS into ALDH positive (ALDH) and ALDH negative (ALDH) fractions, ALDH being a marker for CSC. These were assayed for mRNA (FIG. 3C) and protein (FIG. 3D) expression of POU5F1/OCT4, SOX2, NANOG, and SIRPgamma. In FIG. 3C, for each mRNA assessed, the left bar corresponds to A549 ALDH$^+$ cells and the right bar corresponds to A549 ALDH cells. The level of mRNA for ALDHA1 was used to quantify the extent of enrichment of ALDH cells (approx. 13-fold). These results demonstrate that the ALDH$^+$ CSC population shows significantly higher expression of all the three "stemness-associated" transcription factors and SIRPgamma than the bulk population of A549 cells.

FIG. 4A-4C show FACS selection for SIRPgamma expression enriches for cancer stem cells (CSC) according to some aspects of this disclosure. FIG. 4A shows FACS sorting for SIRPgamma positive (SIRPG*) cells. A549 human lung adenocarcinoma cells, grown in monolayer culture, were incubated with a commercially available monoclonal antibody to the SIRPgamma protein and a fluorescent-labeled secondary anti-IgG antibody. The most highly fluorescent cells (4.6%; labeled SIRPG$^+$) were separated from the remainder of the population with the gating shown. FIG. 4B shows Western immunoblots of FACS-sorted SIRPgamma positive (SIRPG*) A549 cells that confirm enrichment of SIRPgamma protein and also show strong enrichment of CD47 protein as compared to SIRP-gamma negative (SIRPG). The SIRPgamma positive cells further show comparably elevated expression of OCT4 (POUSF1) and SOX2 transcription factors as CSC isolated by spheroid culture or by sorting for ALDH expression (see FIGS. 3A-3D). The results imply that SIRPgamma is expressed preferentially by CSC of the A549 cell population. FIG. 4C shows growth curves (8 days) of fractionated A549 SIRPgamma positive (Sirpg*) and SIRPgamma negative (Sirpg⁻) cells from FIG. 4A in standard culture demonstrate increased proliferative capacity of the SIRPgamma positive putative CSC from A549 cells. The SIRPgamma positive cells also showed significantly greater tumor-forming capacity in vivo (see FIG. 7A-7C).

FIG. 5A and FIG. 5B show that sphere formation of human lung adenocarcinoma cancer stem cells requires SIRPgamma according to some aspects of this disclosure. The experiment probes the "stemness" of the CSC. A knockdown experiment was performed using shRNA targeting SIRPgamma. Human A549 human lung adenocarcinoma cells were tested for dependence of sphere formation on SIRPgamma by exposure to a specific shRNA (labeled Sh-Sirpg) and incubation under sphere-forming conditions (see FIG. 3A-3D) in four sequential passages (primary through 3$^{rd}$; CSC selective medium: serum-free medium supplemented with EGF and FGF). A nonspecific shRNA was used as control (labeled Sh-Control). Both the efficiency of sphere formation (percentage of cells found in oncospheres) and the number of cells per sphere were reduced significantly by the specific SIRPgamma shRNA as shown in FIG. 5A and FIG. 5B, respectively. Comparable results were obtained for H1975 cells (not shown).

FIG. 6 shows that sphere formation of human lung adenocarcinoma cancer stem cells can be inhibited by a SIRPgamma monoclonal antibody (mAb) according to some aspects of this disclosure. Cells were incubated in CSC selective medium in 96-well non-adherent plates as in FIG. 5A-5B at the indicated densities per well in the presence of the following mAbs (all at 20 mg/ml): control IgG (black); SE7C2 to SIRPalpha (SIRPa), but cross-reactive with SIRPgamma (dark grey); and LSB2.20 specific for SIRPgamma (light grey). Oncosphere formation was assessed by light microscopy. Representative images of these cells are shown in FIG. 16A.

As shown in FIG. 7A, SIRPgamma positive FACS-selected cells show enhanced tumor initiating capacity (diamonds) as compared to SIRPgamma negativecells (circles). The data demonstrate much faster initiation of tumors in mice injected with SIRPgamma positive cells; tumor formation by the SIRPgamma negative cells lagged that of SIRPgamma positive cells by approximately 2 weeks. This is consistent with the approximately 20-fold enrichment of CSC (tumor-initiating cells) in the SIRPgamma positive population. A knockdown experiment was also performed using shRNA targeting SIRPgamma (shRNA-SIRPG). As shown in FIG. 7B and FIG. 7C, shRNA-SIRPgamma inhibits tumor formation by SIRPgamma positive FACS-selected CSC. SIRPgamma positive FACS-selected A549 cells (as described in FIG. 7A) were infected with a lentiviral vector encoding either of two different shRNAs for SIRPgamma (designated Sh-SIRPG-1 and Sh-SIRPG-2) or a control shRNA, and then fixed numbers of cells were injected into flanks of immune-deficient mice.

FIG. 7B shows photographs of tumors, and FIG. 7C shows measurement of tumor volume, both at 6 weeks post-injection. The knockdown of SIRPgamma by each gene-specific shRNA reduced the tumorigenic potential of the CSC to a level equivalent to that of the SIRPgamma negative FACS-selected population shown in FIG. 7A.

FIG. 9A shows confocal immunofluorescence showing localization of YAP1 and SOX2 proteins in cells treated with control shRNA (Sh-Cont=shLUC) or shRNA to SIRPgamma (Sh-Sirpg). DAPI=nuclear staining; Merge=superimposition of DAPI, YAP1, SOX2 staining. FIG. 9B shows that knockdown of SIRPgamma activates Hippo pathway signaling in lung adenocarcinoma cells. A549 cells were transduced with vectors expressing a control shRNA (shLuc for luciferase), or with a shRNA specific to the SIRPgamma gene (shSIRPG-1, shSIRPG-2) as in FIG. 9. Protein lysates were assessed by Western immunoblot using antibodies specific to total MST1, LATS1, YAP1, or SOX2, and to the phosphorylated forms p-MST1, p-LATS1, and pYAP (P-Ser127) GAPDH served as a loading control. (LATS1 is labeled as LAST1 in figure.) FIG. 9C shows that a SIRPgamma monoclonal antibody activates Hippo pathway signaling in lung adenocarcinoma cells. A549 cells were incubated with a control mouse IgG1 mAb, mAb SE7C2 to SIRPalpha, or mAb LSB2.20 to SIRPgamma. Protein lysates were prepared for Western immunoblot analysis using antibodies specific to total MST1, LATS1, YAP1, or SOX2, or to the phosphorylated forms p-MST1, p-LATS1, and pYAP (P-Ser127). GAPDH served as a loading control.

FIG. 11A and FIG. 11B show regulation of CD47 expression by SIRPgamma in human lung cancer cells according to some aspects of this disclosure, including reciprocal effects of knock down and overexpression. FIG. 11A shows the relative expression of SIRPgamma mRNA by qRT-PCR in control A549 cells and after introduction of expression vectors for three different gene-specific shRNAs (Sh-SIRPG-77, Sh-SIRPG-78, Sh-SIRPG-79; labeled as A549-77, A549-78, and A549-79, respectively). FIG. 11B (left side) shows protein expression of CD47, SIRPgamma (SIRPG), and GAPDH (loading control) by Western immunoblotting in A549 cells treated with control shRNA (Sh-Control) and the three shRNAs specific for the SIRPgamma gene. FIG. 11B (right side) shows protein expression of CD47, SIRPgamma (SIRPG), and GAPDH in A549 cells infected with a control empty expression vector or the same vector containing a cloned, full-length SIRPgamma cDNA (labeled as Ov-SIRPG).

FIG. 12A and FIG. 12B show enhanced sensitivity of human lung cancer cells to phagocytosis by macrophages by treatment with a shRNA-targeting SIRPgamma (shRNA-SIRPG) or binding of a SIRPgamma-specific monoclonal antibody according to some aspects of this disclosure. Human A549 lung adenocarcinoma cells, untreated or treated with a nonspecific shRNA (shRNA-control), are largely refractory to phagocytic killing by macrophages (using the transformed murine RAW264.7 cell line as a convenient, reproducible source of functional macrophages). FIG. 12A shows knockdown of SIRPgamma expression using shRNA-SIRPG strongly enhances killing of A549 cells when co-cultured with RAW264.7 macrophages. FIG. 12B shows that A549 cells remain largely resistant to phagocytosis by RAW264.7 macrophages in the presence of a non-specific IgG. However, incubation with a monoclonal antibody to either of the paired receptors SIRP-gamma or CD47 activates phagocytosis of the A549 cells, consistent with shutting off "don't eat me" signaling. Phagocytosis appears somewhat further increased by incubation of the lung cancer cells with both anti-SIRPgamma and anti-CD47.

FIG. 15A shows the mRNA levels of Yap target genes in A549 cells after treatment with blocking antibodies (20 µg/mL) for 24 h, assessed by qRT-PCR. In the graph, for each mRNA assessed, the bars from left to right, correspond to IgG, SIRPalpha-antibody, SIRPgamma-antibody (LSB2.20), SIRPg-antibody (OX119), and CD47 antibody, respectively. FIG. 15B, the left panel, shows double label flow cytometry analysis of the number of CD47+ cells in GFP-labeled A549 cells that are treated with isotype control IgG or infected with lentiviruses carrying different constructs: a control shRNA ("vector+shControl"), a SIRP-gamma transgene and a control shRNA ("Sirpg+shControl"), a shRNA against Yap ("Vector+shYap"), or a SIRPgamma cDNA and a shRNA against Yap ("Sirpg+shYap"). FIG. 15B, the right panel, shows the number of CD47' cells in the GFP-labeled A549 cells in bar chart format. The four bars, from left to right, correspond to "vector+shControl", "Sirpg+shControl", "Vector+shYap", and "Sirpg+shYap", respectively. FIG. 15C shows that A549 cancer cells infected with lentiviruses carrying SIRPgamma cDNA and shRNA against Yap (Sirpg+shYap) and A549 cells infected with a shRNA against Yap were significantly phagocytosed by macrophages. RFP bone marrow derived macrophages (BMDM) were co-cultured with GFP' cancer cells infected with lentiviruses carrying SIRPgamma or/and shRNA against Yap. Percentage of phagocytosis was determined by the percentage of GFP' A549 cells within RFP macrophage cell gate.

FIG. 17A-17D show that SIRPgamma high expressing A549 cells (SIRPG$^{high}$) displayed enhanced subcutaneous xenograft growth compared to SIRPgamma low expressing A549 cells (SIRPG$^{low/-}$) in vivo, according to some aspects of this disclosure. FIG. 17A indicates the locations and amount of sorted SIRPG$^{high}$ A549 cells or SIRPG$^{low}$ A549 cells that were implanted into immune deficient, male, nude mice; and FIG. 17B shows photographs of exemplary mice after sacrifice at 5 weeks after the implantation; arrows indicate tumor growth. FIG. 17C shows photographs of exemplary mice after sacrifice at 5 weeks after the implantation. FIG. 17D illustrates the tumor growth (volume) over time in the mice implanted with SIRPG$^{high}$ A549 cells (upper row) and SIRPG$^{low}$ A549 cells (lower row) as described with respect to FIGS. 17A-17D. FIG. 17D shows photographic images of tumors harvested at the end of the study period of 6 weeks, from mice implanted with SIRP-G$^{low}$ A549 cells (top row) and mice implanted with SIRPG$^{high}$ A549 cells (bottom row). SIRPgamma high cells show enhanced tumor initiating capacity (diamonds) as compared to SIRPgamma low cells (circles), as shown in FIG. 7A.

FIG. 18B shows the mRNA levels of some of the Yap target genes in A549 cells after treatment with an anti-SIRPgamma mAb blocking antibodies (20 µg/mL) for 24 h, assessed by qRT-PCR. Each sample was tested in triplicates. In the graph, for each mRNA assessed, the bar on the left corresponds to IgG-treated cells and the bar on the right corresponds to anti-SIRPgamma antibody-treated cells. Treating A549 cells with anti-SIRPgamma antibody LSB2.20 (SIRPg LSB2.20) enhanced phorphorylation of MST1, LATS1, and YAP (FIG. 18A) and inhibited mRNA expression levels of SOX2, IL1B, GM-CSF, and CD47 (FIG. 18B). Treating cells with anti-SIRPalpha antibody (SIRPa) did not affect the assessed markers (FIG. 18A). FIG. 18C shows RT-PCR results of the A549 cells treated with a control shRNA ("shControl"), an anti-SIRPgamma antibody (Ab-SIRPG), cytokines IL-1β (IL-1β), GM-CSF, or combinations thereof. mRNA were extracted from the treated A549 cells and RT-PCR reactions were performed to assess the expression levels of CD47. FIG. 18D shows the results of sphere formation of the A549 cells treated with IgG or anti-SIRPgamma for 48 hours. FIG. 18E shows the percentages of A549 cells treated with, from left to right in the graph, i) IgG (20 µg/mL), ii) anti-CD47 antibody (20 µg/mL), iii) anti-SIRPgamma (20 µg/mL) for 48 hours, and iv) anti-SIRPgamma for 48 hours which is followed by incubating with a combination of anti-SIRPgamma (20 µg/mL) and anti-CD47 (20 µg/mL) for an additional 4 hours. The A549 cells treated as described above were incubated with PE-cy7 labeled rat anti-mouse CD11-b and APC labeled rat anti-mouse F4/80 under 4° C. for 30 minutes, then washed and re-suspended in cold flow buffer and analyzed by flow cytometry. Cells that have undergone phagocytosis are those positive for both CD11-b and F4/80.

FIG. 19A-19E show the effect of an anti-SIRPgamma antibody treatment in vivo in a xenograft model, according to some aspects of this disclosure. FIG. 19A shows a schematic of the timeline for implantation of A549 cells into immune-deficient, nude, male mice and anti SIRPgamma antibody treatment schedule. FIG. 19B shows the tumor growth (volume) curve from mice treated with control IgG and SIRPgamma antibody as per the timeline (administered 25 µg, 50 µg, and 100 µg per mouse, with the average weight of the mice being 21 gram). Each group contained 5 mice, and the graphs show average tumor volume in each group. FIG. 19C shows the corresponding tumor weight measurements. FIG. 19D shows the results of phagocytosis in the tumor cells as assessed by flow cytometry. Tumors were removed from the treated mice and minced and digested into a single cell suspension as described in the methods in Example 9. The single cell suspension were then incubated with PE-cy7 labeled rat anti-mouse CD11-b and APC labeled rat anti-mouse F4/80 under 4° C. for 30 minutes, then washed and re-suspended in cold flow buffer and analyzed by flow cytometry. Cells that have undergone phagocytosis are shown as those positive for both CD11-b and F4/80 and the percentages of these cells are shown in FIG. 19D. FIG. 19E shows the ratio of human to mouse DNA in xenograft macrophages in tumors from mice treated with IgG, and different doses of anti-SIRPgamma antibody (50 µg or 100 µg).

DETAILED DESCRIPTION

I. Definitions

Figure 1A:
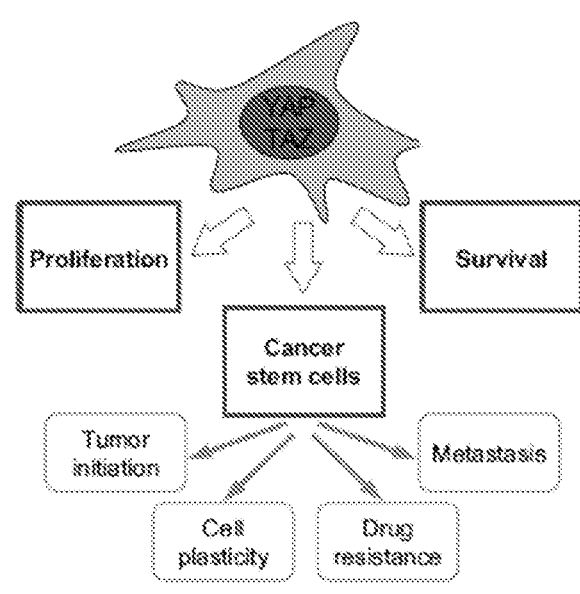
FIG. 1A shows a schematic overview of cancer cell properties mediated by YAP/TAZ.

Unless defined otherwise, all technical and scientific terms used herein have the same meaning as commonly understood by one of ordinary skill in the art. Practitioners are particularly directed to Current Protocols in Molecular Biology (Ausubel) for definitions and terms of the art. Abbreviations for amino acid residues are the standard 3-letter and/or 1-letter codes used in the art to refer to one of the 20 common L-amino acids.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10. Additionally, any reference referred to as being "incorporated herein" is to be understood as being incorporated in its entirety.

It is further noted that, as used in this specification, the singular forms "a," "an," and "the" include plural referents unless expressly and unequivocally limited to one referent. The term "or" is used interchangeably with the term "and/or" unless the context clearly indicates otherwise.

Also, the terms "portion" and "fragment" are used interchangeably to refer to parts of a polypeptide, nucleic acid, or other molecular construct.

As used herein the terms "cancer" and "tumor" are used to indicate malignant tissue. The term, "cancer" is also used to refer to the disease associated with the presence of malignant tumor cells in an individual, and the term "tumor" is used to refer to a plurality of cancer cells that are physically associated with each other. Cancer cells are malignant cells that give rise to cancer, and tumor cells are malignant cells that can form a tumor and thereby give rise to cancer.

As used herein, an "effective amount" means the amount of an agent that is effective for producing a desired effect in a subject. The actual dose which comprises the effective amount may depend upon the route of administration, the size and health of the subject, the disorder being treated, and the like.

The term "pharmaceutically acceptable carrier" as used herein may refer to compounds and compositions that are suitable for use in human or animal subjects, as for example, for therapeutic compositions administered for the treatment of a disorder or disease of interest.

"Treat," "treatment," and other forms of this word refer to the administration of an agent to impede growth of a cancer, to do one or more of the following: cause a cancer to shrink by weight or volume, extend the expected survival time of the subject, or extend the expected time to progression of the tumor, or the like.

II. SIRPgamma

This disclosure describes methods relating to Signal Regulatory Protein Gamma (SWISSPROT accession no. Q9P1W8; also referred to herein as SIRPgamma, SIRPγ, SIRPg, and SIRPG). Signal-regulatory protein gamma is encoded by the SIRPgamma gene; also known as SIRP-gamma (SIRPgamma or SIRPG), SIRPB2, SIRP-B2, CD172g, or bA77C3.1. It is one of three members of a gene family involved in immune regulation. The other family members are named SIRPalpha (SWISSPROT accession no. P78324) and SIRPbeta (SWISSPROT accession no. O00241). See Brooke et al. J. Immunol. 2004 173:2562-2570, which is hereby incorporated by reference.

Human SIRPgamma (SWISSPROT accession no. Q9P1W8) is expressed as a precursor of 387 amino acids, with a 28 residue signal peptide which is cleaved from the mature membrane-bound protein. It has extracelluclar Ig-like domains, which are (from the N-terminus, which is distal to the plasma membrane): D1, Ig-like V-type, redisues 29-D1, Ig-like V-type, residues 29-137; D2, Ig-like C1-type, residues 146-245. D3, Ig-like C1-type, residues 252-340. There is a transmembrane domain and an intracellular "stub" of four amino acids.

Expression of SIRPgamma, like that of its close family members SIRPalpha and SIRPbeta, has been reported primarily in cells of the adaptive and innate immune systems. SIRPgamma is most prominent on certain sets of lymphocytes and activated natural killer (NK) cells, while SIRPalpha is associated primarily with myeloid lineage cells, particularly macrophages. The SIRP proteins function as paired receptors with CD47 (integrin associated protein). Binding of SIRPalpha to CD47, in particular, elicits "don't eat me" signaling that inhibits phagocytosis by macrophages. SIRPgamma appears to play roles in the interaction of human T cells with antigen-presenting cells and in their transendothelial migration.

Considerable attention has been paid to the related protein SIRPalpha, which functions in both innate and adaptive immunity and also has activities in the nervous system, bone, and cardiac tissue. SIRPalpha is expressed by myeloid lineage cells, as well as a number of non-blood cell types. It participates in the regulation of dendritic cell function and phagocytosis via interaction with its paired receptor, the integrin-associated protein CD47. In the cells that express SIRPalpha, the intracellular domain undergoes phosphorylation on tyrosine residue. This can occur in response to mitogens and growth factors. This phosphorylation is regulated both by engagement with CD47 and with integrin in a cell type-dependent manner. The phosphorylated signal regions on SIRPalpha recruit SH2 domain-containing protein tyrosine phosphatases such as SHP-2. In at least some cells this enhances the activation of receptor tyrosine kinases by their mitogenic ligands.

SIRPgamma also binds CD47, via engagement of the two proteins' extracellular domains, albeit approximately 10-fold less tightly than SIRPalpha. The interaction of SIRPgamma on human T cells with CD47 on antigen-presenting cells (e.g., dendritic cells) enhances antigen-specific proliferation of the T cells. However, the underlying signal transduction mechanism on the side of the SIRP-gamma-expressing immune cells remains undetermined. Without being held to any specific theory, it may require interaction with some as yet unidentified membrane protein because the intracellular domain of SIRPgamma is a mere stump of 4 amino acids. Thus, the mechanism of direct activation of tyrosine phosphorylation and recruitment of protein tyrosine phosphatases seen with SIRPalpha cannot apply.

CD47 expressed on cancer cells is believed to down-modulate anti-tumor immune responses through interaction with SIRPalpha expressed on macrophages. The interaction of these paired receptors inhibits the phagocytosis of cancer cells by macrophages. Elucidation of this "don't eat me signal" has prompted a number of efforts to develop a therapeutic capable of blocking the SIRPalpha/CD47 interaction, such as an anti-CD47 monoclonal antibody (mAb).

High expression of CD47 is an adverse prognostic factor in both leukemias and solid tumors. There is a specific correlation of elevated CD47 with aggressive, metastatic disease. For example, in a study of NSCLC while just slightly more than half of both squamous cell carcinomas and adenocarcinomas of the lung showed high CD47 expression, the overwhelming majority (>95%) of cases with multiple lymph node metastases, distant metastases, and more advanced clinical staging (Stage III or IV disease) were CD47$^{high}$ (Zhao, H., et al. CD47 promotes tumor invasion and metastasis in non-small cell lung cancer. *Sci Rep* 2016; 6:29719) The relationship of CD47 expression with the aggressiveness of cancer may reflect both intrinsic effects on cell signaling and modulation of the anti-tumor immune response. As provided herein, SIRPgamma expression in cancer stem cells positively regulates the expression of CD47. As such, methods are provided for down-modulating SIRPgamma thereby decreasing CD47 expression and, in some instances, thus inhibiting metastasis.

III. Methods

Provided herein are methods to treat, inhibit, or ameliorate cancer in a subject. The methods include administering to a subject an effective amount of one or more SIRPgamma targeted agents described herein. Also, provided are prognostic and diagnostic methods for cancer based on detection and/or quantitation of SIRPgamma using a SIRPgamma targeted agent.

As used throughout, subject can be a vertebrate, more specifically a mammal (e.g. a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and the term patient or subject includes human and veterinary subjects. The SIRPgamma targeted agents described herein are useful for treating cancer in humans, including, without limitation, pediatric and geriatric populations, and in animals, e.g., veterinary applications. In one embodiment, the subject is a human.

The subject may have one of various of different cancers, including, for example, lung cancer, colorectal cancer, breast cancer, prostate cancer, ovarian cancer, cervical cancer, a sarcoma, skin cancer, testicular cancer, renal cancer, brain cancer, or leukemia. Where the subject has lung cancer, the lung cancer may include bronchogenic cancer, squamous cell carcinoma, small cell lung cancer, adenocarcinoma, or undifferentiated large cell lung cancer. In one example, the subject has lung cancer. In some instances, the subject has non-small cell lung cancer. In another example, the subject has breast cancer. In another example, the subject has colorectal cancer. In some instances, the subject may have a primary cancer. In other instances, the subject may have metastatic cancer. Effective amount, when used to describe an amount of compound in a method, refers to the amount of a SIRPgamma targeted agent (alone or part of a combination therapy) that achieves the desired pharmacological effect or other biological effect.

In one aspect, provided are methods for assessing SIRP-gamma expression in a tumor, the method comprising measuring in a tumor sample from a subject the amount of SIRPgamma. In some instances, the method comprises determining if a subject has a high level of SIRPgamma expression or a low to undetectable level of SIRPgamma expression. A subject's cancer may be characterized as SIRPgamma$^{high}$ or SIRPgamma$^{low}$ by this method using, for example, immunohistochemistry. In some instances, where flow cytometry is used in the method of assessing SIRP-gamma expression, cancers may be characterized as SIRP gamma positive or SIRPgamma negative based on the detected expression of SIRPgamma or not, respectively.

In another aspect, provided are methods of assessing eligibility of a subject for inclusion in or exclusion from a clinical trial. The method comprises (a) measuring in a tumor sample from a subject the amount of SIRPgamma; (b) determining if a subject has a cancer characterized as having a high level of SIRPgamma expression; and (c) indicating that the subject is eligible for a clinical trial of a SIRPgamma targeted therapy if the subject's cancer is characterized as having a high level of SIRPgamma expression, i.e., above a predetermined threshold or that the subject is ineligible for a clinical trial of SIRPgamma targeted therapy if the subject's cancer is characterized as having a low level of SIRPgamma expression, i.e., below a predetermined threshold. In some instances, the threshold level is a median amount of SIRPgamma determined in a reference population of patients having the same kind of cancer as the subject. In another instance, the threshold level is an optimal amount of SIRPgamma determined in a reference population of patients having the same kind of cancer as the subject. "Optimal cutoff" as used herein, refers to the value of a predetermined measure on subjects exhibiting certain attributes that allow the best discrimination between two categories of an attribute. For example, finding a value for an optimal cutoff that allows one to best discriminate between two categories (subgroups) of patients for determining at least one of overall survival, time to disease progression, progression-free survival, and likelihood to respond to treatment (e.g., based on clinical assessment using the RECIST criteria, e.g., Eisenhauer, E. A., et al., Eur. J. Cancer 45:228-247 (2009) or the like as recognized in the medical field). Optimal cutoffs are used to separate the subjects with values lower than or higher than the optimal cutoff to optimize the prediction model, for example, without limitation, to maximize the specificity of the model, maximize the sensitivity of the model, maximize the difference in outcome, or minimize the p-value from hazard ratio or a difference in response.

In another aspect, provided are methods for assessing responsiveness of a subject with cancer to a SIRPgamma targeted agent comprising: (a) measuring in a tumor sample from a subject the amount of SIRPgamma; (c) determining if the subject has a cancer characterized as having a high level of SIRPgamma expression; and (d) indicating that the subject is more likely to respond to the SIRPgamma targeted agent if the subject's cancer is characterized as having a high level of SIRPgamma expression. Conversely, if the subject's cancer is characterized as having a low level of SIRPgamma expression, the subject is less likely to respond to a SIRP-gamma targeted agent.

In another aspect, provided are methods to diagnose cancer in a subject. Specifically, the diagnosis may be of a SIRPgamma expressing cancer. The method may comprise measuring in a sample from a subject the amount of SIRP-gamma and diagnosing the subject with cancer if the amount of SIRPgamma expression in the sample is high. In some instances, the method may comprise (a) measuring in a tumor sample from a subject the amount of SIRPgamma; and (c) determining if the subject has a cancer characterized as having a high level of SIRPgamma expression. Conversely, if the amount of SIRPgamma expression in the sample or the subject's cancer low level, the subject may not be diagnosed with cancer or may not be diagnosed with a SIRPgamma expressing cancer.

In some instances, to diagnose cancer in a subject, or to characterize a subject's cancer, a biopsy is typically taken from a subject having an abnormal tissue growth, such as a tumor. Samples may be formalin-fixed, paraffin-embedded tissue samples obtained from the subject's cancer (tumor). In other instances, such as where circulating tumor cells are to be assessed, the sample from the subject is a blood, plasma, or lymph sample. Typically, the tissue or cells of the patient sample re examined under a microscope in order to confirm the diagnosis and/or assess information about the tumor. In some cases, additional tests may need to be performed on the proteins, DNA, and/or mRNA of the cells in the ample to verify the diagnosis or characterization.

In some embodiments, SIRPgamma expression in cancer cells can be examined by using one or more routine biochemical analyses. In some embodiments, SIRPgamma expression is determined by detecting SIRPgamma transcript expression, using methods such as microarray and RT-PCR. In other embodiments, SIRPgamma expression may be determined by detecting protein expression, using methods such as, Western blot analysis, flow cytometry, and immunohistochemistry staining. In yet other embodiments, SIRPgamma expression may be determined using a combination of these methods.

In some instances, a threshold amount of SIRPgamma expression is used to characterize SIRPgamma expression as either high or low. A high level of SIRPgamma expression refers to a measure of SIRPgamma expression above a particular threshold. For example, the threshold may be a normal, an average, or a median amount of SIRPgamma expression as measured in a particular set of samples, referred to as a reference population. In some instances, the reference population may be a population of normal/healthy subjects. In other instances, the reference population may be a population of subjects having a particular type of cancer (the same type of cancer that the subject being assessed has). A low level of SIRPgamma expression refers to the converse of the above. For example, the threshold may be determined by identifying two distinct subgroups in the reference population by dividing samples around a mathematically determined point, such as, without limitation, a median, thus creating a subgroup whose measure is high (i.e., higher than the median) and another subgroup whose measure is low. SIRPgamma can be measured by any method known to one skilled in the art (examples given above).

In a preferred embodiment, immunohistochemistry staining is performed and a H-score method is used to quantify the expression of SIRPgamma in a cancer tissue sample (biopsy). In an exemplary assay, formalin-fixed, paraffin-embedded tumor tissue sections prepared from a biopsy of the subject's tumor are deparaffinized and treated with antigen retrieval solution to render the SIRPgamma protein readily accessible to anti-SIRPgamma antibodies. Anti-SIRPgamma antibodies are then incubated with the tissue sections and the antibodies bound to the SIRPgamma on the tissue sections are detected by addition of a horse peroxidase (HRP) conjugated secondary antibody that recognizes the anti-SIRPgamma antibody. The HRP on the secondary antibody conjugate catalyzes a colorimetric reaction and upon contacting the appropriate substrate, produces a staining in the locations where SIRPgamma is present. In one approach, the intensity level of the SIRPgamma staining is represented by 0 for negative staining, 1+ for weak staining, 2+ for moderate staining, and 3+ for strong staining according to standard methodology. See ihcworld.com/ihc_scoring.htm. The percentage of SIRPgamma$^{high}$ cells of each intensity level is multiplied with the intensity level, and the results for all intensity levels are summed to generate a H-score between 0-300. In one embodiment, a cancer having a H-score equal to or higher than a predetermined threshold is considered SIRPgamma$^{high}$ (or SIRPgamma) cancer. In a preferred embodiment, the threshold for designating a cancer as SIRPgamma$^{high}$ is an H-score of at least 150. In another embodiment, a SIRPgamma$^{high}$ cancer is one that has at least 10%, 15%, 20%, 25%, or 30% tumor cells having SIRPgamma staining at any intensity. In a preferred embodiment, a SIRPgamma$^{high}$ cancer is one that has at least 10% tumor cells having SIRPgamma staining at any intensity. As noted above, the terms SIRPgamma, SIRPγ, SIRPg, and SIRPG are all used interchangeably with each other in this disclosure.

In one aspect, provided is a method of treating a subject with cancer, the method comprising administering to the patient a pharmaceutically effective amount of a composition comprising a SIRPgamma targeted agent. The SIRPgamma targeted agent is an agent that specifically binds to SIRPgamma protein or to SIRPgamma mRNA. SIRPgamma targeted agents include antibodies, or fragments thereof, peptides, small molecules, and polynucleotides (such as RNA molecules) that specifically bind to SIRPgamma protein or to SIRPgamma mRNA. The composition may further comprise a pharmaceutically acceptable carrier. In some instances, SIRPgamma targeted agents that bind to the SIRPgamma protein may directly inhibit SIRPgamma activity or may otherwise reduce SIRPgamma activity. In other instances, SIRPgamma targeted agents that bind to SIRPgamma mRNA may inhibit or reduce SIRPgamma expression and thereby inhibit SIRPgamma activity.

In another aspect, provided is a method of treating a subject with cancer, the method comprising administering to the patient a pharmaceutically effective amount of a composition comprising a SIRPgamma targeted agent. The SIRPgamma targeted agent is an agent that specifically binds to SIRPgamma protein or to SIRPgamma mRNA. SIRPgamma targeted agents include antibodies, or fragments thereof, peptides, small molecules, and polynucleotides (such as RNA molecules) that specifically bind to SIRPgamma protein or to SIRPgamma mRNA. The composition may further comprise a pharmaceutically acceptable carrier.

As provided herein, treating subjects with cancer that expresses SIRPgamma with a SIRPgamma targeted agent is new approach to treating such cancers. In some instances, the SIRPgamma targeted agent may directly inhibit growth and induce cell death of cancer stem cells (CSC). In some instances, the SIRPgamma targeted agent may enhance phagocytosis by macrophages that would otherwise be suppressed by the interaction of SIRPgamma with CD47, thereby causing killing of tumor cells, most importantly the CSC, and enhancing anti-tumor immunity. In some instances, treating a subject with the methods described herein inhibits at least one of formation of a tumor, the proliferation of tumor cells, the growth of tumor cells, survival of tumor cells in circulation, or metastasis of tumor cells in the individual. In another embodiment, treating a subject with the methods described herein may result in tumor growth stasis, reduction of tumor size and, in some instances, elimination of one or more tumors in the subject.

Sequence information for SIRPgamma is available from public databases. The gene sequence for SIRPgamma can be found at GenBank Accession No. NM 018556.3 and has been assigned Entrez Gene ID No. 55423. The mRNA sequence for SIRPgamma can be found at GenBank Accession No. NM_018556. The SIRPgamma protein sequence can be found at UniProt/SwissProt Accession No. Q9P1W8. The protein has four isoforms: Q9P1W8-1 (full length), Q9P1W8-2 (missing aa 1-33), Q9P1W8-3 (missing aa 144-360), and Q9P1W8-4 (missing aa 250-360).

In some instances, the SIRPgamma targeted agent may specifically bind to SIRPgamma protein at the site of a protein-binding domain (or portion thereof) thereby reducing the binding of a cellular binding partner to the SIRPgamma protein. For example, in some instances, without being held to any particular theory, the SIRPgamma targeted agent may disrupt the binding of SIRPgamma and CD47. Such agents include SIRPgamma targeted antibodies, or fragments thereof, SIRPgamma targeted peptides, and SIRPgamma targeted small molecules.

In one instance, the SIRPgamma targeted agent may comprise a SIRPgamma targeted antibody. The SIRPgamma targeted antibody may be a monoclonal antibody. In some instances, the SIRPgamma targeted antibody may be a humanized antibody. For example, the SIRPgamma targeted antibody may be a humanized antibody corresponding to any one of antibody LSB2.20 (BioLegend, Inc., San Diego, CA; RRID: AB_1227766; Cat. No. 336606), antibody OX119 (GeneTex, Inc., Irvine, CA; Cat. No. GTX42348), antibody AF4486 or MAB4486 (R&D Systems, Inc., Minneapolis, MN; Cat. No. AF4486 or MAB4486); or antibody PA5-47627 (Invitrogen/ThermoFisher Scientific, Cat. No. PA5-47627). In some instances, the SIRPgamma targeted antibody is a monoclonal antibody fragment as described further below.

In another instance, the SIRPgamma targeted agent may be a SIRPgamma targeted peptide. In yet another instance, the SIRPgamma targeted agent may be a SIRPgamma targeted small molecule. The SIRPgamma targeted peptides and small molecules may be derived in a variety of manners as discussed further below. In some instances, the peptides are derived from the sequence of a SIRPgamma targeted antibody.

In one aspect, provided is a method of inhibiting expression of the SIRPgamma protein by contacting a cell expressing the SIRPgamma gene with a synthetic SIRPgamma targeted RNA molecule. SIRPgamma targeted RNA molecules are described further below. The cell expressing the SIRPgamma gene may be a cancer cell, such as a cancer stem cell, in a subject.

In some instances, the SIRPgamma targeted agent may specifically bind to SIRPgamma mRNA. For example, the SIRPgamma targeted agent may be a SIRPgamma targeted RNA molecule. Exemplary SIRPgamma targeted RNA molecules include siRNAs, short hairpin RNAs (shRNAs), single stranded interfering RNAs, and microRNAs (miRNAs), which are described in more detail below. Such RNA molecules are polynucleotides with sufficient complementarity to SIRPgamma mRNA to result in specific binding and having a sequence and associated secondary structured, as discussed below, to trigger cellular mechanisms for degradation of the SIRPgamma mRNA. In some instances, the SIRPgamma targeted agent that specifically bind to SIRPgamma mRNA may be a protein, peptide, or small molecule that triggers cellular mechanisms for degradation of the SIRPgamma mRNA.

In some instances, the SIRPgamma targeted agent itself may not be therapeutic but may be used to target a therapeutic agent to cancer stem cells, as discussed further below.

In such instances, the SIRPgamma targeted agent need only bind specifically to the SIRPgamma protein or SIRPgamma mRNA. Thus, in some instances, the SIRPgamma targeted agent may be conjugated to a therapeutic pharmaceutical agent. The therapeutic pharmaceutical agent may be one or more of a cytotoxic agent, a chemotherapeutic agent, or an immunosuppressive agent.

In some instances, the method further includes administering a second form of cancer therapy to the subject. The second form of cancer therapy may include a cytotoxic agent, a chemotherapeutic agent, an immunosuppressive agent (including immune checkpoint inhibitors), or radiation therapy. Such cancer therapies are discussed further below.

In certain embodiments, the SIRPgamma targeted agent administered to the subject can bind to SIRPgamma on tumor cells to affect second messengers associated with regulation of tumorigenesis, tumor cell proliferation, tumor cell growth, and/or metastasis. In certain embodiments, SIRPgamma targeted agents can prevent, or reduce the risk of at least one of initiation of tumorigenesis, tumor cell proliferation, tumor cell growth, or tumor cell metastasis to thereby treat the subject's cancer. For example, in some embodiments, the SIRPgamma targeted agent may inhibit tumor cell growth. Also, in some embodiments, the SIRPgamma targeted agent may increase tumor cell apoptosis and cell death and/or phagocytosis. By inhibiting tumor cell growth and/or increasing tumor cell death, the SIRPgamma targeted agent may reduce at least one of tumorigenesis, tumor cell proliferation, tumor cell growth and/or metastasis.

Figures 2A, 2B:
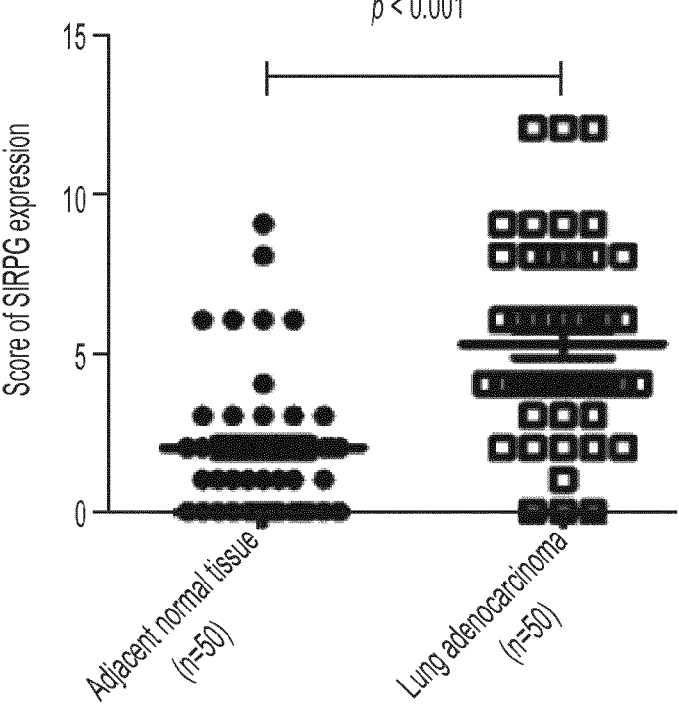
FIG. 2A-2C show analysis of SIRPgamma expression in human lung adenocarcinoma samples according to some aspects of this disclosure. Samples from a group (182) of patients with lung adenocarcinoma (all stages) were assessed immunohistochemically to measure SIRPgamma expression levels.
Figure 2C:
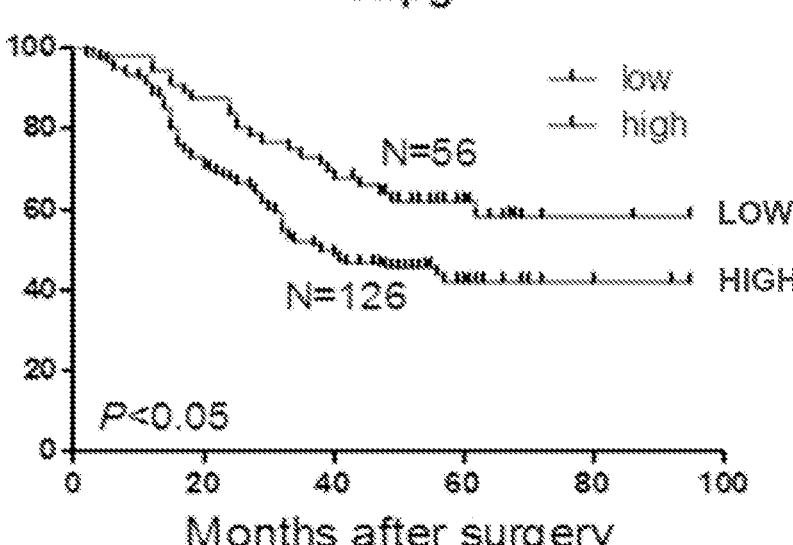

In one embodiment, more than half of the original tumor biopsies in a cohort of lung adenocarcinoma patients (all stages) show definitive staining for SIRPg, with the adjacent non-tumor tissue generally negative. As shown in FIG. 2A and FIG. 2B, such tumors are classified as "SIRPgamma$^{high}$", with non-staining tumors classified as "SIRPgamma$^{low}$". In another embodiment, the survival of patients with SIRPgamma$^{high}$ tumors at 5 years post-biopsy may be more than two-fold below that of patients with SIRPgamma$^{low}$ tumors, as shown in FIG. 2C In another embodiment, this striking survival difference is maintained throughout 15 years after initial diagnosis.

Beyond tumor initiation, a number of surrogate assays are widely recognized to identify CSC. These include spheroid formation and fluorescence-activated cell sorting (FACS) sorting for aldehyde dehydrogenase (ALDH). CSC can initiate, and are significantly enriched in spheroids (also called "oncospheres") that are formed when cancer cells are grown in serum-free medium (usually supplemented with growth factors, e.g., Epidermal Growth Factor (EGF) and Fibroblast Growth Factor (FGF)), and in culture vessels with non-adherent surfaces (e.g., bacteriological petri dishes). CSC preferentially express ALDH and can be enriched by FACS using a substrate for this enzyme giving rise to a non-toxic fluorescent product that accumulates inside cells (e.g., using an Aldefluor™ system, STEMCELL Technologies, Cambridge, MA). In certain embodiments, CSC from A549 and H358 human lung adenocarcinoma cells, enriched by these assays, show elevated expression of SIRPgamma compared to the bulk of cells in standard culture.

In some instances, administering an inhibitor of SIRPgamma to a subject may activate innate immunity to tumor cells by overcoming the CD47 checkpoint. Without being held to any particular theory, a potential mechanism for this may entail: macrophages recognize pro-phagocytic (EAT) signals on tumour cells; tumor cells deliver a "DO NOT EAT" signal through CD47 binding to SIRPalpha; inhibition of SIRPgamma turns off CD47 expression by lung cancer cells and thus prevents binding to SIRPalpha on macrophages; and absence of CD47 turns off the "do not eat" signal and re-activates the phagocytosis of tumor cells by macrophages. Inhibiting SIRP gamma in a subject by the provided methods may inhibit production or secretion of cytokines that inhibit immune function through e.g., inhibition of YAP/TAZ signaling. Non-limiting examples of cytokines that have inhibitory function on the immune system include, but are not limited to, Interleukin 1-beta (IL1-beta) and GM-CSF.

Figure 8:
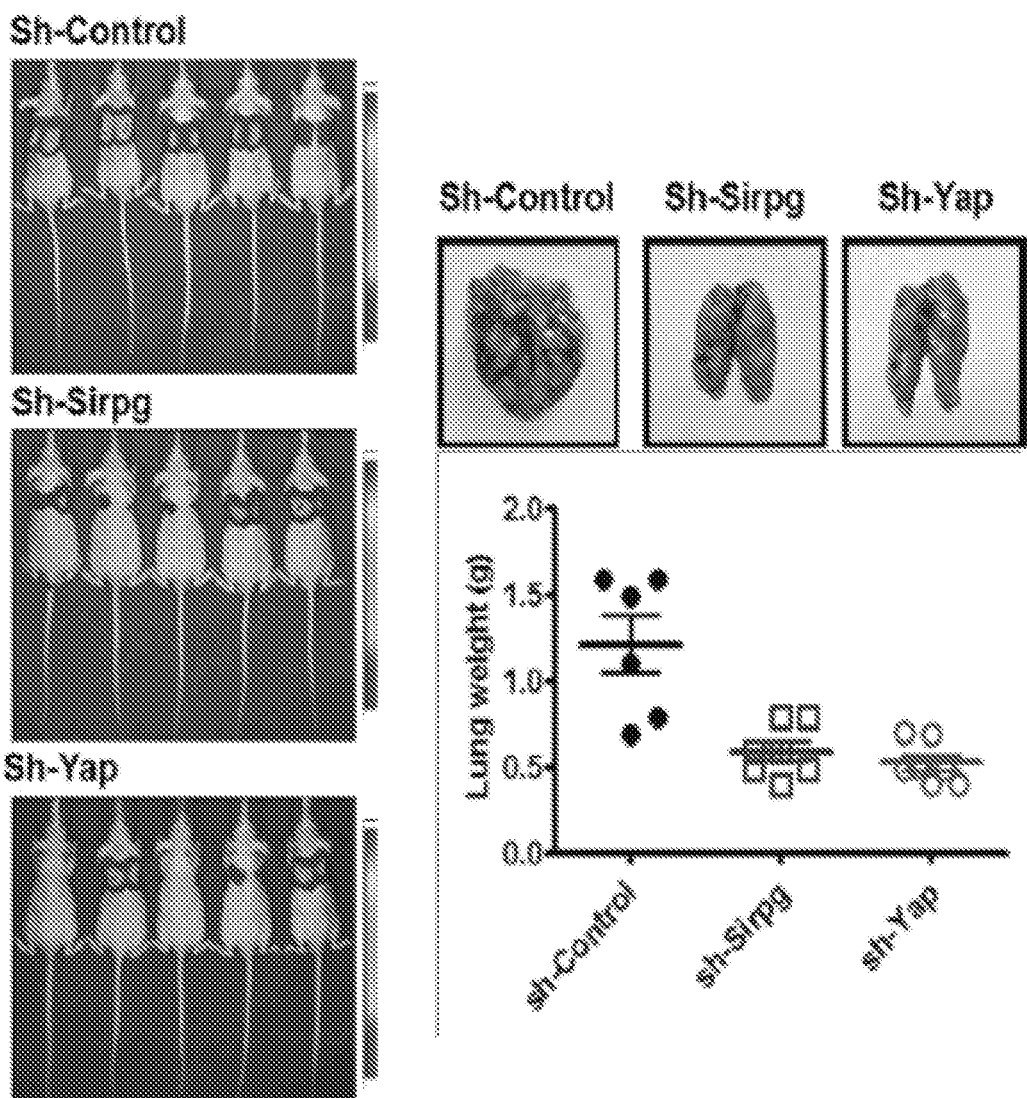
FIG. 8 shows the growth of human adenocarcinoma cells in a xenograft lung metastasis model according to some aspects of this disclosure, demonstrating the dependence of tumor growth on SIRPgamma and YAP1. AS49 cells that had been transfected to stably express firefly luciferase (Xenogen, Alemeda, CA) were infected with lentiviruses carrying control shRNA (Sh-5 Control), shRNA for SIRPgamma (Sh-Sirpg), or shRNA for YAP1 (Sh-Yap). Cells ($1\times10^5$ per mouse) were injected into the lateral tail vein of 6-week-old female SCID mice (6 per group) and tumors were assessed 7 weeks later. Imaging of luciferase in individual mice by IVIS Spectrum is shown on the left. Photographs of representative whole lungs from each of the 3 groups is shown on the top right. Weights of lungs from individual mice is shown on the bottom right.

In another instance, without being held to any particular theory, administering an inhibitor of SIRPgamma to a subject with SIRPgamma$^{high}$ NSCLC may be efficacious in the following manner: inhibition of YAP activates apoptotic genes in CSC and more differentiated (bulk) tumor cells; inhibition of CD47 expression renders CSC and bulk tumor cells susceptible to phagocytosis by macrophages and activates anti-tumor immunity; loss of CSC will inhibit relapse and metastasis; and loss of CSC will eliminate cells most resistant to current standard-of-care therapies. In some instances, inhibiting SIRPgamma by the provided methods causes an increase in the levels of phosphorylated MST1 and LATS1, proteins components in the Hippo signaling pathway, as shown in FIG. 9. Inhibiting SIRPgamma by the provided methods may also inhibit the anchorage-independent growth of the CSC. In some instances, administration of a SIRPgamma targeted agent can cause a significant decrease in tumor burden in the lung, e.g., a decrease of more than 20%, more than 25%, or more than 50%, as shown in FIG. 8.

Figure 2D:
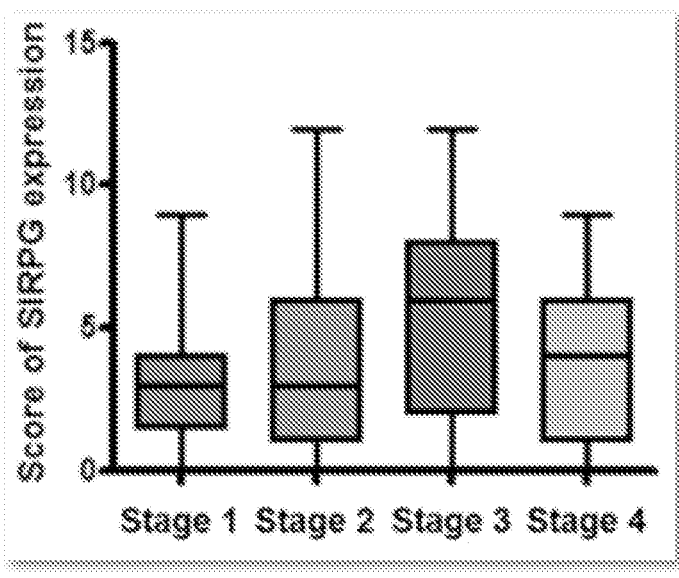
FIG. 2D shows a breakdown of SIRPg expression by disease stage, with more advanced stages of cancer correlating more positively with higher SIRPg expression (relative scoring scale of 1-15).

In one embodiment, over half of human lung adenocarcinomas in a cohort representing all disease stages highly express SIRPgamma, and about one-third co-express SIRPgamma and CD47. In some instances, the double positive phenotype (SIRPgamma$^{high}$, CD47$^{high}$) associates with sharply decreased disease-specific survival. In some embodiments, the level of expression of SIRP gamma is positively correlated with more advanced stages of disease (e.g., stage 3 and 4) as shown in FIG. 2D.

In one embodiment, SIRPgamma is upregulated in CSC of human lung carcinoma cell lines, assayed by sphere formation and expression of stem cell markers. Further, sorted SIRPgamma-positive lung cancer cells proliferate faster and are much more invasive (zebrafish model) than SIRPgamma-negative cells (data not shown).

In another embodiment, knockdown of SIRPgamma by shRNA inhibits invasion and migration of CSC and inhibits the sphere-forming ability of these cells, indicating decreased "stemness." Thus, in one embodiment, administering a SIRPgamma inhibitor to a subject with cancer abrogates CSC stemness, inhibits growth and/or triggers apoptosis of cells expressing SIRPgamma, and/or reverse multiple hallmarks of aggressive cancers as described in FIG. 1A.

In another embodiment, SIRPgamma-positive lung adenocarcinoma cells display considerably more potent tumor-initiating ability than SIRPgamma-negative cells in vivo (xenografts in immune-deficient mice). Knockdown of SIRPgamma with shRNA decreases the tumorigenic potential of the enriched CSC. In another embodiment, inhibition with a commercial pan-SIRP monoclonal antibody confirm this observation. In one embodiment, the SIRP gamma targeted agent is administered at a concentration that causes an increase of at least 2 fold, at least 3-fold, at least 4-fold, or at least 5-fold increase in phagocytosis of human lung adenocarcinoma cells. In some embodiments, SIRPgamma- $^{high}$ lung adenocarcinoma cells have more potent tumor-initiation ability than SIRPgamma$^{low}$ lung adenocarcinoma cells. In some instances, introducing SIRPgamma$^{high}$ lung adenocarcinoma cells (e.g., 5.0× 10e4 of SIRPgamma$^{high}$ A549 cells) can establish xenograph tumors in animals that are immune-deficient, as shown for example in Table 1). In some embodiments, as illustrated in FIG. 17D-17E, when the cell number introduced in the animals and the length of growth period are the same, the average volume of the tumorsderived from SIRPgamma$^{high}$ lung adenocarcinoma cells is at least 30%, at least 40%, or at least 50% larger than the average volume of tumors derived from SIRPgamma$^{low}$ lung adenocarcinoma cells introduced into such immune-deficient animals.

In some embodiments, administering a SIRPgamma targeted agent (e.g., a SIRPgamma targeted antibody) to a subject having a tumor (e.g., a lung adenocarcinoma tumor) enhances cancer cell phagocytosis by at least 13%, at least 30%, or at least 50% as compared to controls, where the extent of phagocytosis is determined based on the number of cancer cells that have undergone phagocytosis. An exemplary embodiment of this as demonstrated in a xenograft mouse model is shown in FIG. 19B in which the SIRPgamma targeted agent is a monoclonal antibody specific for SIRPgamma. For example, the anti-SIRPgamma antibody may be administered at a dose of about 1.19 mg/kg, 2.38 mg/kg, or 5 mg/kg. In some embodiments, administration of a SIRPgamma targeted agent is able to reduce tumor volume by at least 20%, at least 30%, at least 50%, or at least 70% over a period of 21 days. An exemplary embodiment of this as demonstrated in a xenograft mouse model is shown in FIG. 19B-19C in which the SIRPgamma targeted agent is a monoclonal antibody specific for SIRPgamma.

Administration of the SIRPgamma targeted agents described herein can be carried out using therapeutically effective amounts of the agent for periods of time effective to treat a disorder. The effective amount of the compounds and compositions described herein or pharmaceutically acceptable salts thereof as described herein may be determined by one of ordinary skill in the art. Those of skill in the art will understand that the specific dose level and frequency of dosage for any particular subject may be varied and will depend upon a variety of factors, including the type of SIRPgamma targeted agents, the activity of the specific compound employed, the metabolic stability and length of action of that compound, the species, age, body weight, general health, sex and diet of the subject, the mode and time of administration, rate of excretion, drug combination, and severity of the particular condition. The precise dose to be employed in the formulation will also depend on the route of administration, and the seriousness of the disease or disorder, and should be decided according to the judgment of the practitioner and each subject's circumstances. Effective doses can be extrapolated from dose-response curves derived from in vitro or animal model test systems. Further, depending on the route of administration, one of skill in the art would know how to determine doses that result in a plasma concentration for a desired level of response in the cells, tissues and/or organs of a subject.

The SIRPgamma targeted agents described herein are suitable of administration in vitro or in vivo. Optionally, the agents can further comprise a pharmaceutically acceptable carrier. By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. The carrier is selected to minimize any degradation of the active ingredient and to minimize any adverse side effects in the subject.

Suitable carriers and their formulations are described in Remington: *The Science and Practice of Pharmacy*, 21$^{st}$ *Edition*, David B. Troy, ed., Lippicott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally about 5 to about 8 or from about 7 to 7.5. Other carriers include sustained release preparations such as semipermeable matrices of solid hydrophobic polymers containing the immunogenic polypeptides. Matrices are in the form of shaped articles, e.g., films, liposomes, or microparticles. Certain carriers may be more preferable depending upon, for instance, the route of administration and concentration of composition being administered. Carriers are those suitable for administration of the composition, e.g., the polypeptides described herein to humans or other subjects.

The agents are administered in a number of ways depending on whether local or systemic treatment is desired, and on the area to be treated. The compositions are administered via any of several routes of administration, including topically, orally, parenterally, intravenously, intra-articularly, intraperitoneally, intramuscularly, subcutaneously, intracavity, transdermally, intrahepatically, intracranially, nebulization/inhalation, or by installation via bronchoscopy.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives are optionally present such as, for example, antimicrobials, anti-oxidants, chelating agents, and inert gases and the like.

Formulations for topical administration include ointments, lotions, creams, gels, drops, suppositories, sprays, liquids, and powders. Conventional pharmaceutical carriers, aqueous, powder, or oily bases, thickeners and the like are optionally necessary or desirable.

Compositions for oral administration include powders or granules, suspension or solutions in water or non-aqueous media, capsules, sachets, or tables. Thickeners, flavorings, diluents, emulsifiers, dispersing aids or binders are optionally desirable.

Also provided are methods of imaging a tumor in a subject with a SIRPgamma expressing cancer, the method comprising administering to the subject a SIRPgamma targeted agent conjugated to an imaging label, and detecting the imaging label in the subject. Imaging methods may be used to assess tumor size and changes in tumor size over or after the course of a treatment administered to the subject. The methods may be useful to assess response of the subject to an administered treatment. In some instances, the methods may be useful to grade the subject's cancer. Such methods are discussed further below.

A. SIRPgamma Targeted Agent—Antibodies

In some instances, the SIRPgamma targeted agent may be a SIRPgamma targeted antibody. For example, the SIRPgamma targeted antibody may be a monoclonal antibody of any species (e.g., mouse, rat, rabbit, or human). In another example, the SIRPgamma targeted antibody may be a humanized antibody such as, for example, one derived from a non-human antibody (e.g., mouse, rat, or rabbit). In some instances, the SIRPgamma targeted antibody may be any one of antibody LSB2.20 (BioLegend, Inc., San Diego, CA; RRID: AB_1227766; Cat. No. 336606), antibody OX119 (GeneTex, Inc., Irvine, CA; Cat. No. GTX42348), antibody AF4486 or MAB4486 (R&D Systems, Inc., Minneapolis, MN; Cat. No. AF4486 or MAB4486); or antibody PA5-47627 (Invitrogen/ThermoFisher Scientific, Cat. No. PA5-47627). In some instances, the SIRPgamma targeted antibody may be a humanized antibody corresponding to any of these commercially available antibodies.

As used herein, the term antibody encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (κ) and lambda (λ), based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called alpha, delta, epsilon, gamma, and mu, respectively.

The term variable is used herein to describe certain portions of the antibody domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies. The constant domains are not involved directly in binding an antibody to an antigen, but exhibit various effector functions, such as participation of the antibody in antibody-dependent cellular toxicity.

As used herein, the term epitope is meant to include any determinant capable of specific interaction with the provided antibodies. Epitopic determinants usually consist of chemically active surface groupings of molecules such as amino acids or sugar side chains and usually have specific three dimensional structural characteristics, as well as specific charge characteristics. Identification of the epitope that the antibody recognizes is performed as follows. First, various partial structures of the target molecule that the monoclonal antibody recognizes are prepared. The partial structures are prepared by preparing partial peptides of the molecule. Such peptides are prepared by, for example, known oligopeptide synthesis technique or by incorporating DNA encoding the desired partial polypeptide in a suitable expression plasmid. The expression plasmid is delivered to a suitable host, such as E. coli, to produce the peptides. For example, a series of polypeptides having appropriately reduced lengths, working from the C- or N-terminus of the target molecule, can be prepared by established genetic engineering techniques. By establishing which fragments react with the antibody, the epitope region is identified. The epitope is more closely identified by synthesizing a variety of smaller peptides or mutants of the peptides using established oligopeptide synthesis techniques. The smaller peptides are used, for example, in a competitive inhibition assay to determine whether a specific peptide interferes with binding of the antibody to the target molecule. If so, the peptide is the epitope to which the antibody binds. Commercially available kits, such as the SPOTs Kit (Genosys Biotechnologies, Inc., The Woodlands, TX) and a series of multipin peptide synthesis kits based on the multipin synthesis method (Chiron Corporation, Emeryvile, CA) may be used to obtain a large variety of oligopeptides.

The term antibody or fragments thereof can also encompass chimeric antibodies and hybrid antibodies, with dual or multiple antigen or epitope specificities, and fragments, such as F(ab')2, Fab', Fab and the like, including hybrid fragments. Thus, fragments of the antibodies that retain the ability to bind their specific antigens are provided. For example, fragments of antibodies which maintain SIRPgamma binding activity are included within the meaning of the term antibody or fragment thereof. Such antibodies and fragments can be made by techniques known in the art and can be screened for specificity and activity according to general methods for producing antibodies and screening antibodies for specificity and activity (See Harlow and Lane. Antibodies, A Laboratory Manual. Cold Spring Harbor Publications, New York (1988)).

Also included within the meaning of antibody or fragments thereof are conjugates of antibody fragments and antigen binding proteins (single chain antibodies) as described, for example, in U.S. Pat. No. 4,704,692, the contents of which are hereby incorporated by reference in their entirety, and as discussed below.

Optionally, the antibody is a monoclonal antibody. The term monoclonal antibody as used herein refers to an antibody from a substantially homogeneous population of antibodies, i.e., the individual antibodies comprising the population are identical except for possible naturally occurring mutations that may be present in minor amounts. Monoclonal antibodies may be prepared using hybridoma methods, such as those described by Kohler and Milstein, Nature, 256:495 (1975) or Harlow and Lane, Antibodies, A Laboratory Manual. Cold Spring Harbor Publications, New York (1988). In a hybridoma method, a mouse or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent can be SIRPgamma or an immunogenic fragment thereof.

Generally, either peripheral blood lymphocytes (PBLs) are used in methods of producing monoclonal antibodies if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, pp. 59-103 (1986)). Immortalized cell lines are usually transformed mammalian cells, including myeloma cells of rodent, bovine, equine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium") substances that prevent the growth of HGPRT-deficient cells.

Immortalized cell lines useful here are those that fuse efficiently, support stable high level expression of antibody by the selected antibody-producing cells, and are sensitive to a medium such as HAT medium. Immortalized cell lines include murine myeloma lines, which can be obtained, for instance, from the Salk Institute Cell Distribution Center; San Diego, Calif. and the American Type Culture Collection; Rockville, Md. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, Marcel Dekker, Inc., New York (1987) pp. 51-63).

The culture medium in which the hybridoma cells are cultured can then be assayed for the presence of monoclonal antibodies directed against SIRPgamma or selected epitopes thereof. The binding specificity of monoclonal antibodies produced by the hybridoma cells can be determined by immunoprecipitation or by an in vitro binding assay, such as radioimmunoassay (RIA) or enzyme-linked immunoabsorbent assay (ELISA). Such techniques and assays are known in the art, and are described further in Harlow and Lane Antibodies, A Laboratory Manual, Cold Spring Harbor Publications, New York (1988).

After the desired hybridoma cells are identified, the clones may be subcloned by limiting dilution or FACS sorting procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells can serve as a preferred source of such DNA. Once isolated, the DNA may be placed into expression vectors, which are then transfected into host cells such as simian COS cells, Chinese hamster ovary (CHO) cells, plasmacytoma cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (see U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody provided herein, or can be substituted for the variable domains of one antigen-combining site of an antibody to create a chimeric bivalent antibody comprising one antigen-combining site having specificity for SIRPgamma and another antigen-combining site having specificity for a different antigen. In some embodiments, anti-SIRPgamma monoclonal antibody can also be produced using yeast display methods, such as those described in U.S. Pat. Pub. Nos. 20030027213; 20090181855; 20100227774; 20130197201; 20140221250; 20140377269; and 20130331297, or phage display methods, such as those described in U.S. Pat. Pub. No. 20090181855 for example.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348, U.S. Pat. No. 4,342,566, and Harlow and Lane, Antibodies, A Laboratory Manual, Cold Spring Harbor Publications, New York, (1988). Papain digestion of antibodies typically produces two identical antigen binding fragments, called Fab fragments, each with a single antigen binding site, and a residual Fc fragment. Pepsin treatment yields a fragment, called the F(ab')2 fragment that has two antigen combining sites and is still capable of cross-linking antigen.

The Fab fragments produced in the antibody digestion can also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group.

One method of producing proteins comprising the provided antibodies or fragments thereof is to link two or more peptides or polypeptides together by protein chemistry techniques. For example, peptides or polypeptides can be chemically synthesized using currently available laboratory equipment using either Fmoc (9-fluorenylmethyl-oxycarbonyl) or Boc (tert-butyloxycarbonoyl) chemistry (Applied Biosystems, Inc.; Foster City, CA). Those of skill in the art readily appreciate that a peptide or polypeptide corresponding to the antibody provided herein, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group that is functionally blocked on the other fragment. By peptide condensation reactions, these two fragments can be covalently joined via a peptide bond at their carboxyl and amino termini, respectively, to form an antibody, or fragment thereof. (Grant GA (1992) Synthetic Peptides: A User Guide. W. H. Freeman and Co., N.Y. (1992); Bodansky M and Trost B., Ed. (1993) Principles of Peptide Synthesis. Springer Verlag Inc., NY). Alternatively, the peptide or polypeptide can by independently synthesized in vivo. Once isolated, these independent peptides or polypeptides may be linked to form an antibody or fragment thereof via similar peptide condensation reactions.

For example, enzymatic ligation of cloned or synthetic peptide segments can allow relatively short peptide fragments to be joined to produce larger peptide fragments, polypeptides or whole protein domains (Abrahmsen et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776 779 (1994)). The first step is the chemoselective reaction of an unprotected synthetic peptide a thioester with another unprotected peptide segment containing an amino terminal Cys residue to give a thioester linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini et al., FEBS Lett. 307:97-101 (1992); Clark et al., J. Biol. Chem. 269:16075 (1994); Clark et al., Biochemistry 30:3128 (1991); Rajarathnam et al., Biochemistry 33:6623-30 (1994)).

Alternatively, unprotected peptide segments can be chemically linked where the bond formed between the peptide segments as a result of the chemical ligation is an unnatural (non peptide) bond (Schnolzer et al., Science 256:221 (1992)). This technique has been used to synthesize analogs of protein domains as well as large amounts of relatively pure proteins with full biological activity (deLisle et al., Techniques in Protein Chemistry IV. Academic Press, New York, pp. 257-267 (1992)).

The provided polypeptide fragments can be recombinant proteins obtained by cloning nucleic acids encoding the polypeptide in an expression system capable of producing the polypeptide fragments thereof, such as a bacterial, adenovirus or baculovirus expression system. For example, one can determine the active domain of an antibody from a specific hybridoma that can cause a biological effect associated with the interaction of the antibody with SIRPgamma. For example, amino acids found to not contribute to either the activity or the binding specificity or affinity of the antibody can be deleted without a loss in the respective activity.

The provided fragments, whether attached to other sequences, can also include insertions, deletions, substitutions, or other selected modifications of particular regions or specific amino acids residues, provided the activity of the fragment is not significantly altered or impaired compared to the nonmodified antibody or epitope. These modifications can provide for some additional property, such as to remove or add amino acids capable of disulfide bonding, to increase its bio longevity, to alter its secretory characteristics, and the like. In any case, the fragment can possess a bioactive property, such as binding activity, regulation of binding at the binding domain, and the like. Functional or active regions may be identified by mutagenesis of a specific region of the protein, followed by expression and testing of the expressed polypeptide. Such methods are readily apparent to a skilled practitioner in the art and can include site specific mutagenesis of the nucleic acid encoding the antigen. (Zoller et al., Nucl. Acids Res. 10:6487-500 (1982)).

In some instances, the antibody or binding fragment thereof, can be modified to enhance antibody-dependent cell killing. For example, amino acid substitutions can be made in the Fc region of the antibodies or fragments disclosed herein to increase binding of Fc receptors for enhanced antibody dependent cell cytotoxicity or increased phagocytosis.

Further provided herein is a humanized or human version of the antibody. Optionally, the antibody modulates the activity of the SIRPgamma protein by activating or inhibiting the SIRPgamma protein. Optionally, the humanized or human antibody comprises at least one complementarity determining region (CDR) of an antibody having the same epitope specificity as an antibody produced by the hybridoma cell line disclosed herein. For example, the antibody can comprise all CDRs of an antibody having the same epitope specificity as an antibody produced by the hybridoma cell line.

Optionally, the humanized or human antibody can comprise at least one residue of the framework region of the monoclonal antibody produced by a disclosed hybridoma cell line. Humanized and human antibodies can be made using methods known to a skilled artesian; for example, the human antibody can be produced using a germ-line mutant animal or by a phage display library.

Antibodies can also be generated in other species and humanized for administration to humans. Alternatively, fully human antibodies can also be made by immunizing a mouse or other species capable of making a fully human antibody (e.g., mice genetically modified to produce human antibodies) and screening clones that bind SIRPgamma. See, e.g., Lonberg and Huszar, Int. Rev. Immunol. 13:65-93, (1995), which is incorporated herein by reference in its entirety for methods of producing fully human antibodies. As used herein, the term humanized and human in relation to antibodies, relate to any antibody which is expected to elicit a therapeutically tolerable weak immunogenic response in a human subject. Thus, the terms include fully humanized or fully human as well as partially humanized or partially human.

Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from non-human immunoglobulin. Humanized antibodies include human immunoglobulins (recipient antibody) in which residues from a CDR of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues.

Humanized antibodies may also comprise residues that are found neither in the recipient antibody nor in the imported CDR or framework sequences. In general, the humanized antibody will comprise substantially all or at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature, 332:323-327 (1988); and Presta, Curr. Op. Struct. Biol., 2:593-596 (1992)).

Generally, a humanized antibody has one or more amino acid residues introduced into it from a source that is non-human. These non-human amino acid residues are often referred to as import residues, which are typically taken from an import variable domain. Humanization can be essentially performed following the methods described in Jones et al., Nature 321:522-525 (1986); Riechmann et al., Nature 332:323-327 (1988); or Verhoeyen et al., Science 239:1534-1536 (1988), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

In some embodiments, the anti-SIRPgamma antibody described herein is a bi-specific antibody in which one portion of the antibody recognizes SIRPgamma and another portion of the antibody recognizes a second antigen. In some embodiments, the second antigen is SIRPalpha. In some embodiments, the second antigen is SIRPbeta. In some embodiments, the bi-specific antibody binds to an epitope of SIRPgamma and to a epitope of SIRPalpha, SIRPbeta, or both, that have at least 99%, 98%, 97%, 96%, 95%, 90%, 85%, 80%, 75%, or 70% sequence identity with each other. In some embodiments, the bi-specific antibody binds to an epitope of SIRPgamma and to a epitope of SIRPalpha or SIRPbeta that have substantial tertiary structure configuration with each other in the native proteins. In certain embodiments, the bi-specific antibody binds specifically to both SIRPgamma and SIRPbeta. In some embodiments, the anti-SIRPgamma antibody is a pan-SIRP antibody, which binds to SIRPalpha, SIRPbeta, and SIRPgamma.

The nucleotide sequences encoding SIRPgamma targeted antibodies can be readily identified using conventional procedures (e.g., by using oligonucleotide probes that are capable of binding specifically to genes encoding the heavy and light chains of murine antibodies). These nucleotide sequences can also be modified, or humanized, for example, by substituting the coding sequence for human heavy and light chain constant domains in place of the homologous murine sequences (see, e.g., U.S. Pat. No. 4,816,567). The nucleotide sequences encoding such antibodies can be expressed in appropriate host cells. These include prokaryotic host cells including, but not limited to, *E. coli, Bacillus subtilus*, other enterobacteriaceae such as *Salmonella typhimurium* or *Serratia marcesans*, and various *Pseudomonas* species. Eukaryotic host cells can also be utilized. These include, but are not limited to, yeast cells (for example, *Saccharomyces cerevisiae* and *Pichia pastoris*), and mammalian cells such as VERO cells, HeLa cells, Chinese hamster ovary (CHO) cells, W138 cells, BHK cells, COS-7 cells, 293T cells and MDCK cells. The antibodies produced by these cells can be purified from the culture medium and assayed for binding, activity, specificity or any other property of the monoclonal antibodies by utilizing the methods set forth herein and standard in the art.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J (H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., Proc. Natl. Acad. Sci. USA 90:2551-255 (1993); Jakobovits et al., Nature 362:255-258 (1993); Bruggemann et al., Year in Immuno. 7:33 (1993)). Human antibodies can also be produced in phage display libraries (Hoogenboom et al., J. Mol. Biol., 227:381 (1991); Marks et al., J. Mol. Biol., 222:581 (1991)). The techniques of Cole et al. and Boerner et al. are also available for the preparation of human monoclonal antibodies (Cole et al., Monoclonal Antibodies and Cancer Therapy, Alan R. Liss, ed., p. 77 (1985); Boerner et al., J. Immunol., 147 (1): 86-95 (1991)).

B. SIRPgamma Targeted Agent—Small Molecules and Peptides

Optionally, the SIRPgamma targeted agent may be a SIRPgamma targeted small molecule or peptide. Small molecules and peptides that are capable of inhibiting the function of SIRPgamma can be obtained using any of the numerous approaches in combinatorial library methods known in the art, including: biological libraries; spatially addressable parallel solid phase or solution phase libraries; synthetic library methods requiring deconvoluation; and synthetic library methods using affinity chromatograpy selection. Typically, the biological library is a peptide library, while the other four approaches are applicable to peptide, non-peptide oligomer or small molecule libraries of compounds (Lam, K. S. (1997) Anticancer Drug. Des. 12:145).

Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med Chem. 37:1233.

Libraries of compounds can be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. 5,223,409), plasmids (Cull et al. (1992) Proc. Natl. Acad. Sci. USA 89:1865-1869), or on phage (Scott and Smith (1990) Science 249:386-390); (Devlin (1990) Science 249:404-406); (Cwirla et al. (1990) Proc. Natl. Acad. Sci. USA 87:6378-6382); (Felici (1991) J. Mol. Biol. 222:301-310); (Ladner supra.).

One method of producing SIRPgamma targeted peptides is by protein synthesis. In some instances, two or more peptides may be linked together by protein chemistry techniques. For example, peptides can be chemically synthesized using currently available laboratory equipment using either Fmoc (9-fluorenylmethyl-oxycarbonyl) or Boc (tert-buty-loxycarbonoyl) chemistry (Applied Biosystems, Inc.; Foster City, CA). Those of skill in the art readily appreciate that a peptide sequence of interest can be synthesized by standard chemical reactions. For example, a peptide can be synthesized and not cleaved from its synthesis resin whereas the another peptide can be synthesized and subsequently cleaved from the resin, thereby exposing a terminal group that is functionally blocked on the other fragment. By peptide condensation reactions, these two peptides can be covalently joined via a peptide bond at their carboxyl and amino termini, respectively, to form an antibody, or fragment thereof. (Grant GA (1992) Synthetic Peptides: A User Guide. W. H. Freeman and Co., N.Y. (1992); Bodansky M and Trost B., Ed. (1993) Principles of Peptide Synthesis. Springer Verlag Inc., NY). Alternatively, the peptide can by independently synthesized in vivo. Once isolated, these independent peptides may be linked to form an antibody or fragment thereof via similar peptide condensation reactions.

For example, enzymatic ligation of cloned or synthetic peptide segments can allow relatively short peptide fragments to be joined to produce larger peptide fragments, polypeptides or whole protein domains (Abrahmsen et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776 779 (1994)). The first step is the chemoselective reaction of an unprotected synthetic peptide a thioester with another unprotected peptide segment containing an amino terminal Cys residue to give a thioester linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini et al., FEBS Lett. 307:97-101 (1992); Clark et al., J. Biol. Chem. 269:16075 (1994); Clark et al., Biochemistry 30:3128 (1991); Rajarathnam et al., Biochemistry 33:6623-30 (1994)).

Alternatively, unprotected peptide segments can be chemically linked where the bond formed between the peptide segments as a result of the chemical ligation is an unnatural (non peptide) bond (Schnolzer et al., Science 256:221 (1992)). This technique has been used to synthesize analogs of protein domains as well as large amounts of relatively pure proteins with full biological activity (deLisle et al., Techniques in Protein Chemistry IV. Academic Press, New York, pp. 257-267 (1992)).

A number of well-known assays can be used to assess whether a small molecule or peptide can inhibit the function of SIRPgamma. Non-limiting exemplary assays include binding assays (such as Enzyme-Linked Immunosorbent Assays (ELISAs), radioimmunoassays (RIA)), Fluorescence-Activated Cell Sorting (FACS) analysis, cell-based assays, and in vivo assays.

In one embodiment, the assay is a direct binding assay. The SIRPgamma protein can be coupled with a radioisotope or enzymatic label such that binding of the checkpoint protein and the candidate can be determined by detecting the labeled checkpoint protein in a complex. For example, a checkpoint protein can be labeled with $^{125}I$, $^{35}S$, $^{14}C$, or $^{3}H$, either directly or indirectly, and the radioisotope detected by direct counting of radio-emission or by scintillation counting. Determining the ability of candidates to bind their cognate checkpoint protein can be accomplished, e.g., by measuring direct binding. Alternatively, SIRPgamma protein molecules can be enzymatically labeled with, for example, horseradish peroxidase, alkaline phosphatase, or luciferase, and binding of the candidates to the target checkpoint protein is determined by conversion of an appropriate substrate to product.

Enzyme-linked immunosorbent assay (ELISA) are commonly used to evaluate a CIA candidate's binding specificity to the SIRPgamma protein. In one exemplar assay, microtiter plates are coated with the SIRPgamma protein. Candidate small molecules or peptides are diluted in appropriate buffer and are incubated in the wells coated with the SIRPgamma protein. The wells are then washed and antibodies recognizing the SIRPgamma protein is then added to the wells to form immunocomplexes comprising the antibodies, the SIRPgamma protein and the candidate small molecule or peptide. The immunocomplexes are then detected by secondary antibodies that can bind to the anti-SIRPgamma antibodies. The secondary antibodies are typically conjugated to a label or an enzyme, for example, horseradish peroxidase, which produces signals that correspond to the amount of the immunocomplexes formed in the wells.

The binding kinetics (e.g., binding affinity) of the candidates also can be assessed by standard assays known in the art, such as by Biacore analysis (Biacore AB, Uppsala, Sweden). In one exemplary assay, a purified recombinant human SIRPgamma is covalently linked to a CM5 chip (carboxy methyl dextran coated chip) via primary amines, using standard amine coupling chemistry and kit provided by Biacore. Binding is measured by flowing the candidates in a buffer at a concentration and at a flow rate as suggested by the manufacturer. Typically, the SIRPgamma protein-candidate association kinetics are followed for 1 to 10 minutes, e.g., 3 minutes; and the dissociation kinetics are followed for a period of 3 to 12 minutes, e.g., 7 minutes. The association and dissociation curves are fitted to a 1:1 Langmuir binding model using BIA evaluation software (Biacore AB). The $K_D$, $K_{on}$ and $K_{off}$ values of the interaction can be measured. Preferred SIRPgamma inhibitor small molecule or peptide can bind to SIRPgamma with a Kd of $1\times10^{-7}$ M or less.

In another embodiment, the assay to evaluate whether a candidate small molecule or peptide can inhibit the function of SIRPgamma is a cell-based assay. The cell based assay is typically performed after the candidate is confirmed to bind to the SIRPgamma in binding assays, as described above. For example, the various cancer cell lines can be plated in appropriate growth media. Candidate small molecules or peptides can be added to the growth media at suitable concentrations to treat the cancer cells and the viability and proliferation of the cancer cells can be assessed using methods well known in the art, e.g., the CellTiter 96 Aqueous Non-Radioactive Cell Proliferation Assay (Promega). A decrease in cancer cell proliferation and/or viability following the treatment by the candidate small molecule or peptide indicates that the candidate is effective in inhibiting the function of SIRPgamma.

C. SIRPgamma Targeted Agent—RNA Molecules

Optionally, the SIRPgamma targeted agent is a SIRPgamma targeted RNA molecule, i.e., a SIRPgamma interfering RNA. Interfering RNAs, when introduced in vivo, forms a RNA-inducing silencing complex ("RISC") with other proteins and initiate a process known as RNA interference (RNAi). During the RNAi process, the RISC incorporates a single-stranded interfering RNA or one strand of a double stranded interfering RNA. The incorporated strand acts as a template for RISC to recognize complementary mRNA transcript. Once the complementary mRNA is identified, the protein components in RISC activate and cleave the mRNA, resulting in a knock-down of target gene expression. Non-limiting examples of interfering RNA molecules that be used to knock down expression of SIRPgamma include siRNAs, short hairpin RNAs (shRNAs), single stranded interfering RNAs, and microRNAs (miRNAs). Methods for using these interfering RNAs are well known to one of skilled in the art.

In one embodiment, the interfering RNA is a siRNA. siRNA is a double stranded RNA which is typically less than 30 nucleotides long. Gene silencing by siRNA starts with one strand of the siRNA being incorporated into a ribonucleoprotein complex known as the RNA-induced silencing complex (RISC). The strand incorporated in RISC identifies mRNA molecules that are at least partially complementary to the incorporated siRNA strand and the RISC then cleaves these target mRNAs or inhibits their translation.

In one embodiment, the interfering RNA is a microRNA. microRNA is a small non-coding RNA molecule, which can hybridize to complementary sequences within mRNA molecules, resulting cleavage of the mRNA, or destabilization of the mRNA through shortening of its poly(A) tail.

In one embodiment, the interfering RNA is a single-stranded interfering RNA. The single strand can also effect mRNA silencing in a manner that is similar to the double stranded siRNA, albeit less efficient than, the double-stranded siRNA. The single-stranded interfering RNA typically has a length of about 19 to about 49 nucleotides as for the double-stranded siRNA described above.

A short hairpin RNA or small hairpin RNA (shRNA) is an artificial RNA molecule with a tight hairpin turn that can be used to silence target gene expression via the siRNA it produced in cells. Expression of shRNA in cells is typically accomplished by delivery of plasmids or through viral or bacterial vectors. Suitable bacterial vectors include but not limited to adeno-associated viruses (AAVs), adenoviruses, and lentiviruses. shRNA is an advantageous mediator of siRNA in that it has relatively low rate of degradation and turnover.

Interfering RNAs used in the invention may differ from naturally-occurring RNA by the addition, deletion, substitution or modification of one or more nucleotides. Non-nucleotide material may be bound to the interfering RNA, either at the 5' end, the 3' end, or internally. Non-limiting examples of modifications that interfering RNAs may contain relative to the naturally-occurring RNA are disclosed in U.S. Pat. No. 8,399,653, herein incorporated by reference in its entirety. Such modifications are commonly designed to increase the nuclease resistance of the interfering RNAs, to improve cellular uptake, to enhance cellular targeting, to assist in tracing the interfering RNA, to further improve stability, or to reduce the potential for activation of the interferon pathway. For example, interfering RNAs may comprise a purine nucleotide at the ends of overhangs. Conjugation of cholesterol to the 3' end of the sense strand of an siRNA molecule by means of a pyrrolidine linker, for example, also provides stability to an siRNA.

Interfering RNAs used in the invention are typically about 10-60, 10-50, or 10-40 (duplex) nucleotides in length, more typically about 8-15, 10-30, 10-25, or 10-25 (duplex) nucleotides in length, about 10-24, (duplex) nucleotides in length (e.g., each complementary sequence of the double-stranded siRNA is 10-60, 10-50, 10-40, 10-30, 10-25, or 10-25 nucleotides in length, about 10-24, 11-22, or 11-23 nucleotides in length, and the double-stranded siRNA is about 10-60, 10-50, 10-40, 10-30, 10-25, or 10-25 base pairs in length).

Techniques for selecting target motifs in the SIRPgamma gene for RNAi are known to those skilled in the art, for example, as disclosed in Tuschl, T. et al., "The siRNA User Guide," revised May 6, 2004, available on the Rockefeller University web site; by Technical Bulletin #506, "siRNA Design Guidelines," Ambion Inc. at Ambion's web site; and by other web-based design tools at, for example, the Invitrogen, Dharmacon, Integrated DNA Technologies, Genscript, or Proligo web sites. Initial search parameters can include G/C contents between 35% and 55% and siRNA lengths between 19 and 27 nucleotides. The target sequence may be located in the coding region or in the 5' or 3' untranslated regions of the mRNA. The target sequences can be used to derive interfering RNA molecules, such as those described herein.

Efficiency of the knock-down of SIRPgamma can be assessed by measuring the amount of SIRPgamma mRNA or protein using methods well known in the art, for example, quantitative PCR, western blot, flow cytometry, etc and the like. In some embodiments, the level of SIRPgamma protein is evaluated to assess knock-out or knock-down efficiency. In certain embodiments, the reduction of SIRPgamma expression (by any of the identified methods of assessment) is at least 5%, at least 10%, at least 20%, at least 30%, at least 50%, at least 60%, or at least 80% as compared to control cells. In certain embodiments, the efficiency of reduction is from about 10% to about 90%. In certain embodiments, the efficiency of reduction is from about 30% to about 80%. In certain embodiments, the efficiency of reduction is from about 50% to about 80%. In some embodiments, the efficiency of reduction is greater than or equal to about 80%.

D. Conjugates and Co-Therapies

In some instances, the provided methods may include administering to the subject a SIRPgamma targeted agent as described above that is conjugated to a therapeutic agent. The therapeutic agent may be at least one of a cytotoxic agent, a chemotherapeutic agent, or an immunosuppressive agent.

In some instances, the provided methods may include administering a SIRPgamma targeted agent and a second form of cancer therapy to the subject. The second form of cancer therapy may include a cytotoxic agent, a chemotherapeutic agent, an immunosuppressive agent (including immune checkpoint inhibitors), or radiation therapy.

In some instances, the SIRPgamma targeted agent can be labeled, conjugated, or fused with a therapeutic agent or diagnostic agent (such as an imaging agent). The linkage can be covalent or noncovalent (e.g., ionic). Where the SIRPgamma targeted agent is a SIRPgamma targeted antibody, or binding fragment thereof, such antibodies and antibody fragments are referred to antibody-drug conjugates (ADC) or immunoconjugates. The antibody conjugates are useful for the local delivery of therapeutic agents, particularly cytotoxic or cytostatic agents, i.e. drugs to kill or inhibit tumor cells in the treatment of cancer allows targeted delivery of the drug moiety to tumors, and intracellular accumulation therein, where systemic administration of these unconjugated drug agents may result in unacceptable levels of toxicity to normal cells as well as the tumor cells sought to be eliminated. Therapeutic agents include but are not limited to toxins, including but not limited to plant and bacterial toxins, small molecules, peptides, polypeptides and proteins. Genetically engineered fusion proteins, in which genes encoding for an antibody, or fragments thereof including the Fv region, or peptides can be fused to the genes encoding a toxin to deliver a toxin to the target cell are also provided. As used herein, a target cell or target cells are SIRPgamma positive cells.

Techniques for conjugating such a therapeutic moiety to SIRPgamma targeted agents are well known, see, for example, Arnon et al., Monoclonal Antibodies And Cancer Therapy, Reisfeld et al. (eds.), pp. 243-56 (1985); Hellstrom et al., Controlled Drug Delivery (2nd Ed.), Robinson et al. (eds.), pp. 623-53 (1987); Thorpe, Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy" In: Monoclonal Antibodies For Cancer Detection And Therapy, (Baldwin et al. eds.), pp. 303-316 (1985), and Thorpe et al., Immunol. Rev. 62:119-158 (1982). Alternatively, an antibody can be conjugated to a second antibody to form an antibody heteroconjugate as described in U.S. Pat. No. 4,676,980.

Other examples of therapeutic agents include chemotherapeutic agents, a radiotherapeutic agent, and immunotherapeutic agent, as well as combinations thereof. In this way, the antibody or peptide complex delivered to the subject can be multifunctional, in that it exerts one therapeutic effect by binding to the SIRPgamma protein and a second therapeutic effect by delivering a supplemental therapeutic agent.

The therapeutic agent can act extracellularly, for example by initiating or affecting an immune response, or it can act intracellularly, either directly by translocating through the cell membrane or indirectly by, for example, affecting transmembrane cell signaling. The therapeutic agent is optionally cleavable from the SIRPgamma targeted antibody, or fragment thereof, peptide, or small molecule. Cleavage can be autolytic, accomplished by proteolysis, or affected by contacting the cell with a cleavage agent.

A cytotoxin or cytotoxic agent includes any agent that is detrimental to cells. Examples of toxins or toxin moieties include diphtheria, ricin, streptavidin, and modifications thereof. Additional examples include paclitaxel, cisplatin, carboplatin, cytochalasin B, gramicidin D, ethidium bromide, emetine, etoposide, tenoposide, colchicin, dihydroxy anthracin dione, mitoxantrone, mithramycin, actinomycin D, 1-dehydrotestosterone, glucocorticoids, procaine, tetracaine, lidocaine, propranolol, puromycin and analogs or homologs thereof. Therapeutic agents include, but are not limited to, antimetabolites (e.g., methotrexate, 6-mercaptopurine, 6-thioguanine, cytarabine, 5-fluorouracil, decarbazine), alkylating agents (e.g., mechlorethamine, thiotepa, chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Cytotoxic peptides such as auristatin (antineoplastic) peptides auristatin E (AE) and monomethylauristatin (MMAE), which are synthetic analogs of dolastatin, may also be conjugated to the SIRPgamma targeted agents. In some instances, the SIRPgamma targeted agent may be conjugated to a radioactive metal ion.

As referred to herein, a chemotherapeutic agent is a chemical compound useful in the treatment of cancer.

Examples of chemotherapeutic agents include erlotinib (such as TARCEVA®, Genentech/OSI Pharm.), bortezomib (such as VELCADE®, Millenium Pharm.), fulvestrant (such as FASLODEX®, AstraZeneca), sutent (such as SU11248, Pfizer), letrozole (such as FEMARA®, Novartis), imatinib mesylate (such as GLEEVEC®, Novartis), PTK787/ZK222584 (Novartis), oxaliplatin (such as Eloxatin®, Sanofi), 5-fluorouracil (5-FU), leucovorin, rapamycin (also known as sirolimus) (such as RAPAMUNE®, Wyeth), lapatinib (such as TYKERB®, GSK572016, GlaxoSmithKline), lonafarnib (such as SCH 66336), sorafenib (such as BAY43-9006, Bayer Labs.), capecitabine (such as XELODA®, Roche), docetaxel (such as TAXOTERE®), and gefitinib (such as IRESSA®, Astrazeneca), AG1478, AG1571 (such as SU 5271; Sugen Inc.), alkylating agents such as thiotepa and cyclosphosphamide (such as CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, particularly calicheamicin $\gamma_1^{1}$ and calicheamicin $\theta_1^{1}$); dynemicin, including dynemicin A; bisphosphonates, such as clodronate; an esperamicin; as well as neocarzinostatin chromophore and related chromoprotein enediyne antibiotic chromophores), aclacinomysins, actinomycin, anthramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (such as ADRIAMYCIN®, including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; *Trametes Versicolor* polysaccharide-K (Krestin, PSK) (JHS Natural Products, Eugene, OR); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; cytarabine (cytosine arabinoside, "Ara-C"); cyclophosphamide; thiotepa; taxoids, e.g., paclitaxel (such as TAXOL®, Bristol-Myers Squibb Oncology, Princeton, N.J.), ABRAXANE™ (a Cremophor-free, albumin-engineered nanoparticle formulation of paclitaxel (American Pharmaceutical Partners, Schaumberg, IL)), and doxetaxel (such as TAXOTERE®, Rhône-Poulenc Rorer, Antony, France); chloranbucil; gemcitabine (such as GEMZAR®); 6-thioguanine; mercaptopurine; methotrexate; platinum analogs such as cisplatin and carboplatin; vinblastine; platinum; etoposide (VP-16); ifosfamide; mitoxantrone; vincristine; vinorelbine (such as NAVELBINE®); novantrone; teniposide; edatrexate; daunomycin; aminopterin; xeloda; ibandronate; CPT-11; topoisomerase inhibitor RFS 2000; difluorometlhylomithine (DMFO); retinoids such as retinoic acid; capecitabine; and pharmaceutically acceptable salts, acids or derivatives of any of the above.

Chemotherapeutic agents, as used herein, also refers to (i) anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY 117018, onapristone, and toremifene (such as FARESTON®); (ii) aromatase inhibitors that inhibit the enzyme aromatase, which regulates estrogen production in the adrenal glands, such as, for example, 4 (5)-imidazoles, aminoglutethimide, megestrol acetate (such as MEGASE®), exemestane (such as AROMASIN®), formestanie, fadrozole, vorozole (such as RIVISOR®), letrozole (such as FEMARA®), and anastrozole (such as ARIMIDEX®); (iii) anti-androgens such as flutamide, nilutamide, bicalutamide, leuprolide, and goserelin; as well as troxacitabine (a 1,3-dioxolane nucleoside cytosine analog); (iv) aromatase inhibitors; (v) protein kinase inhibitors; (vi) lipid kinase inhibitors; (vii) antisense oligonucleotides, particularly those which inhibit expression of genes in signaling pathways implicated in aberrant cell proliferation, such as, for example, PKC-alpha, Ralf and H-Ras; (viii) VEGF receptor and angiogenesis inhibitors (including ribozymes such as ANGIOZYME®) and a HER2 expression inhibitor; (ix) vaccines such as gene therapy vaccines, for example, ALLOVECTIN-7® vaccine (plasmid/lipid complex containing the DNA sequences encoding HLA-B7 and β2 microglobulin), LEUVECTIN® vaccine (plasmid DNA expression vector encoding interleukin-2 (IL-2) complexed with a lipid delivery vehicle (DMRIE/DOPE)), and VAXID® vaccine (patient-specific naked DNA vaccine); IL-2 or aldesleukin (such as PROLEUKIN®); topoisomerase 1 inhibitors (such as TOPOTECAN®); gonadotropin-releasing hormone antagonists (such as ABARELIX®); (x) anti-angiogenic agents such as bevacizumab (such as AVASTIN®, Genentech); and (xi) pharmaceutically acceptable salts, acids or derivatives of any of the above.

Also provided in this disclosure are treatment methods comprising administration of a SIRPgamma targeted therapy and chemotherapeutic agents that target EGFR.

Such combination therapies may be used to treat cancers that are SIRPgamma$^{high}$ and cancers that contain cancer stem cells (CSC) that express SIRPgamma. There are reports that elevated YAP1 activity appears to cause resistance to one of the most important classes of therapeutic drugs for non-small cell lung cancer (NSCLC), namely, inhibitors of the tyrosine protein-kinase activity of the epidermal growth factor receptor (EGFR). See Sun, P. L., et al., Ann Surg Oncol 2014, 21 (Suppl 4): S610-8; Cheng, H., et al., *Oncotarget* 2016, 7(20): 28976-88; Hsu, P. C., et al., *Oncotarget* 2016, 7(32): 51922-33; Lee, J. E., et al., *Biochem Biophys Res Commun* 2016, 474(1): 154-60). Examples of EGFR-targeted therapeutic drugs in this category include erlotinib, gefitinib, and afatinib (GILOTRIF®, Boehringer Ingelheim). While these EGFR tyrosine-protein kinase inhibitor (TKI) drugs currently are utilized mainly to treat tumors with certain activating mutations affecting EGFR (e.g., exon 19 deletions or the missense mutation L858R, an amino acid substitution at position 858 from leucine to arginine), erlotinib also is approved in the United States to treat advanced NSCLC patients without EGFR mutations who have failed other forms of chemotherapy. Furthermore, SIRPgamma targeted therapy could be utilized in combination with a second-generation or third-generation EGFR TKI that is utilized to treat patients whose cancers have become resistant to a first EGFR TKI because of an additional EGFR mutation such as the missense mutation T790M (an amino acid substitution at position 790 from threonine to methionine). An example of such a drug is osimertinib (TAG-RISSO®, AstraZeneca Pharmaceuticals).

In some embodiments, the EGFR-targeted therapeutic drugs that can be used in combination with the SIRPgamma targeted agent disclosed herein may include monoclonal antibodies targeting the EGFR extracellular domain. An example is necitumumab (Portrazza™, Eli Lilly), which is approved in the United States for treatment, in combination with gemcitabine and cisplatin, of people with metastatic squamous NSCLC. The combination of such a theraeutic with a SIRPgamma targeted therapeuticmay enhance the efficacy of necitumumab or of combination regimens that include necitumumab.

In some embodiments, the treatment methods provided herein include a combination therapy comprising a SIRPgamma targeted therapy and cisplatin. As active YAP1, marked by nuclear localization and observed in about 45 percent of cases of NSCLC, also contributes to resistance to cisplatin (Cheng, H., et al., *Oncotarget* 2016, 7(20): 28976-88), a combination of SIRPgamma targeted therapeutic and cisplatinmay be efficacious in treating cancers with high expression of SIRPgamma.

In some instances, the treatment methods provided herein may further comprise administering an immunosuppressive agent such as an immune checkpoint inhibitor may a administered as part of the method. These treatments work by "taking the brakes off" the immune system (are immunosuppressive), allowing it to mount a stronger and more effective attack against cancer. Several different types of checkpoint inhibitors, targeting different checkpoints or "brakes" on immune cells, are currently in use. Exemplary immunosuppressive agents are PD-1 inhibitors (such as nivolumab and pembrolizumab), PD-L1 inhibitors (such as atezolizumab, durvalumab, and avelumab), and CTLA-4 inhibitors (such as ipilimumab). In one example, the second form of cancer therapy comprises a PD-L1 inhibitor, a PD-1 inhibitor, or a CTLA4 inhibitor. In some instances, combinations of such inhibitors can be administered. In some instances, the PD-L1 inhibitor, the PD-1 inhibitor, and/or the CTLA4 inhibitor may be an inhibitory antibody that binds specifically to PD-L1, PD-1, or CTLA4, respectively.

In some instances, the treatment methods provided herein may further comprise administering radiation therapy to the subject. Radiation therapy uses high-energy radiation to shrink tumors and kill cancer cells. X-rays, gamma rays, and charged particles are types of radiation used for cancer treatment. The radiation may be delivered by a machine outside the body (external-beam radiation therapy), or it may come from radioactive material placed in the body near cancer cells (internal radiation therapy, also called brachytherapy). Systemic radiation therapy uses radioactive substances, such as radioactive iodine, that travel in the blood to kill cancer cells.

E. Vector-Based Administration of SIRPgamma Targeted Agent

Optionally, the nucleic acid molecules or polypeptides described above are administered by a vector comprising the nucleic acid molecule or a nucleic acid sequence encoding the SIRPgamma antibody. There are a number of compositions and methods which can be used to deliver the nucleic acid molecules and/or polypeptides to cells, either in vitro or in vivo via, for example, expression vectors. These methods and compositions can largely be broken down into two classes: viral based delivery systems and non-viral based deliver systems. Such methods are well known in the art and readily adaptable for use with the compositions and methods described herein.

As used herein, plasmid or viral vectors are agents that transport the disclosed nucleic acids into the cell without undesired degradation and include a promoter yielding expression of the nucleic acid molecule and/or adapter polypeptide in the cells into which it is delivered. Viral vectors are, for example, Adenovirus, Adeno-associated virus, herpes virus, Vaccinia virus, Polio virus, Sindbis, and other RNA viruses, including these viruses with the HIV backbone. Also preferred are any viral families which share the properties of these viruses which make them suitable for use as vectors. Retroviral vectors, in general are described by Coffin et al., Retroviruses, Cold Spring Harbor Laboratory Press (1997), which is incorporated by reference herein for the vectors and methods of making them. The construction of replication-defective adenoviruses has been described (Berkner et al., J. Virology 61:1213-20 (1987); Massie et al., Mol. Cell. Biol. 6:2872-83 (1986); Haj-Ahmad et al., J. Virology 57:267-74 (1986); Davidson et al., J. Virology 61:1226-39 (1987); Zhang et al., BioTechniques 15:868-72 (1993)). The benefit and the use of these viruses as vectors is that they are limited in the extent to which they can spread to other cell types, since they can replicate within an initial infected cell, but are unable to form new infections viral particles. Recombinant adenoviruses have been shown to achieve high efficiency after direct, in vivo delivery to airway epithelium, hepatocytes, vascular endothelium, CNS parenchyma, and a number of other tissue sites. Other useful systems include, for example, replicating and host-restricted non-replicating vaccinia virus vectors.

The provided SIRPgamma antibodies, peptides, and/or nucleic acid molecules encoding the SIRPgamma antibodies can be delivered via virus like particles. Virus like particles (VLPs) consist of viral protein(s) derived from the structural proteins of a virus. Methods for making and using virus like particles are described in, for example, Garcea and Gissmann, Current Opinion in Biotechnology 15:513-7 (2004).

The provided SIRPgamma antibodies and peptides can be delivered by subviral dense bodies (DBs). DBs transport proteins into target cells by membrane fusion. Methods for making and using DBs are described in, for example, Pepperl-Klindworth et al., Gene Therapy 10:278-84 (2003).

The provided SIRPgamma antibodies and peptides can be delivered by tegument aggregates. Methods for making and using tegument aggregates are described in International Publication No. WO 2006/110728.

Non-viral based delivery methods, can include expression vectors comprising nucleic acid molecules and nucleic acid sequences encoding the adapter polypeptides, wherein the nucleic acids are operably linked to an expression control sequence. Suitable vector backbones include, for example, those routinely used in the art such as plasmids, artificial chromosomes, BACs, YACs, or PACs. Numerous vectors and expression systems are commercially available from such corporations as Novagen (Madison, WI), Clonetech (Pal Alto, CA), Stratagene (La Jolla, CA), and Invitrogen/ Life Technologies (Carlsbad, CA). Vectors typically contain one or more regulatory regions. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

Preferred promoters controlling transcription from vectors in mammalian host cells may be obtained from various sources, for example, the genomes of viruses such as polyoma, Simian Virus 40 (SV40), adenovirus, retroviruses, hepatitis B virus, and most preferably cytomegalovirus (CMV), or from heterologous mammalian promoters (e.g., β-actin promoter or EF1α promoter), or from hybrid or chimeric promoters (e.g., CMV promoter fused to the β-actin promoter). Of course, promoters from the host cell or related species are also useful herein.

Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 bp in length, and they function in cis. Enhancers usually function to increase transcription from nearby promoters. Enhancers can also contain response elements that mediate the regulation of transcription. While many enhancer sequences are known from mammalian genes (globin, elastase, albumin, fetoprotein, and insulin), typically one will use an enhancer from a eukaryotic cell virus for general expression. Preferred examples are the SV40 enhancer on the late side of the replication origin, the cytomegalovirus early promoter enhancer, the polyoma enhancer on the late side of the replication origin, and adenovirus enhancers.

The promoter and/or the enhancer can be inducible (e.g., chemically or physically regulated). A chemically regulated promoter and/or enhancer can, for example, be regulated by the presence of alcohol, tetracycline, a steroid, or a metal. A physically regulated promoter and/or enhancer can, for example, be regulated by environmental factors, such as temperature and light. Optionally, the promoter and/or enhancer region can act as a constitutive promoter and/or enhancer to maximize the expression of the region of the transcription unit to be transcribed. In certain vectors, the promoter and/or enhancer region can be active in a cell type specific manner. Optionally, in certain vectors, the promoter and/or enhancer region can be active in all eukaryotic cells, independent of cell type. Preferred promoters of this type are the CMV promoter, the SV40 promoter, the beta-actin promoter, the EF1A promoter, and the retroviral long terminal repeat (LTR).

The vectors also can include, for example, origins of replication and/or markers. A marker gene can confer a selectable phenotype, e.g., antibiotic resistance, on a cell. The marker product is used to determine if the vector has been delivered to the cell and once delivered is being expressed. Examples of selectable markers for mammalian cells are dihydrofolate reductase (DHFR), thymidine kinase, neomycin, neomycin analog G418, hygromycin, puromycin, and blasticidin. When such selectable markers are successfully transferred into a mammalian host cell, the transformed mammalian host cell can survive if placed under selective pressure. Examples of other markers include, for example, the *E. coli* lacZ gene, green fluorescent protein (GFP), and luciferase. In addition, an expression vector can include a tag sequence designed to facilitate manipulation or detection (e.g., purification or localization) of the expressed polypeptide. Tag sequences, such as GFP, glutathione S-transferase (GST), polyhistidine, c-myc, hemagglutinin, or FLAG™ tag (Kodak; New Haven, CT) sequences typically are expressed as a fusion with the encoded polypeptide. Such tags can be inserted anywhere within the polypeptide including at either the carboxyl or amino terminus.

F. Dosage

Provided herein is a pharmaceutical composition comprising a SIRPgamma targeted agent, such as antibodies, RNA molecules, small molecules and peptides, which can be administered to a patient in need, e.g., a cancer patient, in an amount effective to achieve their intended purpose. Dosage regimens can be adjusted to provide optimum desired response, e.g., a therapeutic response. Actual dosage levels of the active ingredients in the pharmaceutical compositions may be varied so as to obtain an amount of the active ingredient which is effective to achieve the desired therapeutic response for a particular patient, composition, and mode of administration, without being toxic to the patient. The selected dosage level will depend upon a variety of factors including the activity of the particular compositions of the present invention employed, or the ester, salt or amide thereof, the pharmacokinetics of the composition, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The dosage regimen of the SIRPgamma targeted agent also takes into consideration pharmacokinetics parameters well known in the art, i.e., the rate of absorption, bioavailability, metabolism, clearance, and the like (see, e.g., Hidalgo-Aragones (1996) *J. Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J. Clin. Pharmacol.* 24:103-108; the latest Remington's, supra). The state of the art allows the clinician to determine the dosage regimen for each individual patient based on the disease or condition treated.

In some cases, the SIRPgamma targeted agent is a small molecule, and the pharmaceutical composition comprising the SIRPgamma targeted agent can be administered at a daily dose of about 1 to 2,000 mg, preferably between about 10 and about 1000 mg, and most preferably between about 250 to 500 mg of the active ingredient. The daily dose can be administered in one to four doses per day. Other dosing schedules include one dose per week and one dose per two-day cycle.

In some cases, the SIRPgamma targeted agent is an anti-SIRPgamma antibody, and the dosage (of the active component) ranges from about 0.0001 to 100 mg/kg, and more usually 0.01 to 20 mg/kg, of the patient's body weight. For example dosages can be 0.3 mg/kg body weight, 1 mg/kg body weight, 3 mg/kg body weight, 5 mg/kg body weight, 10 mg/kg body weight or within the range of 0.1-20 mg/kg. In certain examples, the anti-SIRPgamma antibody can be administered at a dose of 1.19 mg/kg, 2.38 mg/kg, or 5 mg/kg once every other day at least four times. An exemplary treatment regime may include administration once per day, once per week, twice a week, once every two weeks, once every three weeks, once every four weeks, once a month, once every 3 months, or once every three to 6 months. In some cases, the treatment comprises administering a SIRPgamma targeted agent according one of the aforementioned dosing regimens for a first period and another of the aforementioned dosing regimens for a second period. In some cases, the treatment discontinues for a period of time before the same or a different dosing regimen resumes. For example, a patient may be on a SIRPgamma targeted agent dosing regimen for two weeks, off for a week, on for another two weeks, and so on. Preferred dosage regimens for a SIRPgamma targeted agent of the invention include 0.1 mg/kg body weight, 0.3 mg/kg body weight, 2 mg/kg body weight, 3 mg/kg body weight, or 10 mg/kg via intravenous administration, with the anti SIRPgamma antibody being given using one of the following dosing schedules: (i) every four weeks for six dosages, then every three months; (ii) every three weeks; (iii) 3 mg/kg body weight once followed by 1 mg/kg body weight every three weeks G. Tumor Imaging In one aspect, the SIRPgamma targeted agent may be useful for analytical purposes (such as protein quantitation or imaging), as discussed further below. In such instances, the SIRPgamma targeted agent need only bind specifically to the SIRPgamma protein or SIRPgamma mRNA. SIRPgamma targeted agents, particularly antibodies, peptides, and small molecules, specific for SIRPgamma may be used in imaging methodologies in evaluating the tumor response to any of the SIRPgamma therapies described above.

Provided are methods of imaging a tumor in a subject with a SIRPgamma expressing cancer. The methods include administering to the subject a SIRPgamma targeted agent conjugated to an imaging label, and detecting the imaging label in the subject to obtain an image of the tumor.

Also provided are methods of monitoring response of a subject with a SIRPgamma expressing cancer to cancer therapy. The methods include administering to the subject a SIRPgamma targeted agent conjugated to an imaging label at a first time point prior to the subject before the subject receives cancer therapy, detecting the imaging label in the subject to obtain a first image of the tumor, administering to the subject a SIRPgamma targeted agent conjugated to an imaging label at a second time point after the subject receives cancer therapy, detecting the imaging label in the subject to obtain a second image of the tumor; and comparing the first image to the second image to determine whether a change in tumor size has occurred. In some instances, the steps of administering to the subject a SIRPgamma targeted agent conjugated to an imaging label at a first time point after the subject receives cancer therapy, detecting the imaging label in the subject to obtain a second image of the tumor; and comparing the first image to the second image to determine whether a change in tumor size has occurred may be repeated at a third time point (or additional time points) after the subject receives cancer therapy.

In one embodiment, a subject or patient is administered one or more agents that carry an imaging label and that are capable of targeting or binding to one or more tumor markers, e.g., SIRPgamma. The agent is allowed to incubate in vivo and bind to the one or more markers associated with the tumors or tissues of a particular phase or associated with tumor tissues. The presence of the label is localized to tumor cells or tissues, and the localized label is detected using imaging devices known to those skilled in the art.

The agent may be a SIRPgamma targeted agent that binds specifically to SIRPgamma. In some embodiments, the SIRPgamma targeted agent may be a SIRPgamma targeted antibody, or binding fragment thereof, a SIRPgamma targeted peptide, or a SIRPgamma small molecule. In some instances, the SIRP-gamma targeted agent may be a SIRP-gamma targeted antibody. For example, the agent may be a polyclonal antibody or monoclonal antibody, or fragments thereof, or constructs thereof including but not limited to, single chain antibodies, bifunctional antibodies, molecular recognition units, and peptides or entities that mimic peptides. The antibodies specific for the tumor markers used in the methods of the invention may be obtained from scientific or commercial sources. Alternatively, recombinant SIRP-gamma peptides or other tumor marker proteins may be also utilized to prepare antibodies etc. as described herein.

The agent may be a SIRPgamma targeted peptide. For example, the peptide may mimic the epitope for an antibody specific for the SIRPgamma protein or other markers associated with the tumor. The peptide may be produced on a commercial synthesizer using conventional solid phase chemistry, as discussed above. By way of example, a peptide may be prepared that includes either tyrosine, lysine, or phenylalanine to which $N_2S_2$ chelate is complexed (see U.S. Pat. No. 4,897,255). An anti-endocrine marker peptide conjugate is then combined with a radiolabel (e.g., sodium $^{99m}$Tc pertechnetate or sodium $^{188}$Re perrhenate) and it may be used to locate tumor cells or tumor tissue.

For imaging purposes, the SIRPgamma targeted agent may be conjugated to an imaging agent. For example, the SIRPgamma targeted agent may be labelled for use in radionuclide imaging. In particular, the agent may be directly or indirectly labelled with a radioisotope. Examples of radioisotopes that may be used in the resent invention are the following: $^{277}$Ac, $^{211}$At, $^{128}$Ba, $^{131}$Ba, $^{7}$Be, $^{204}$Bi, $^{205}$Bi, $^{206}$Bi, $^{76}$Br, $^{77}$Br, $^{82}$Br, $^{199}$Cd, $^{47}$Ca, $^{11}$C, $^{14}$C, $^{36}$Cl, $^{48}$Cr, $^{51}$Cr, $^{62}$Cu, $^{64}$Cu, $^{67}$Cu, $^{165}$Dy, $^{155}$Eu, $^{18}$F, $^{153}$Gd, $^{66}$Ga, $^{67}$Ga, $^{68}$Ga, $^{72}$Ga, $^{198}$Au, $^{3}$H $^{166}$Ho, $^{111}$In, $^{113m}$In, $^{115m}$In, $^{123}$I, $^{125}$I, $^{131}$I, $^{189}$Ir, $^{191m}$Ir, $^{192}$Ir, $^{194}$Ir, $^{52}$Fe, $^{55}$Fe, $^{59}$Fe, $^{177}$Lu, $^{15}$O, $^{191m-191}$Os, $^{109}$Pd, $^{32}$P, $^{33}$P, $^{42}$K, $^{226}$Ra, $^{186}$Re, $^{188}$Re, $^{82m}$Rb, $^{153}$Sm, $^{46}$Sc, $^{47}$Sc, $^{72}$Se, $^{75}$Se, $^{105}$Ag, $^{22}$Na, $^{24}$Na, $^{89}$Sr, $^{35}$S, $^{38}$S, $^{177}$Ta, $^{96}$Tc, $^{99m}$Tc, $^{201}$Tl, $^{202}$Tl, $^{113}$Sn, $^{117m}$Sn, $^{121}$Sn, $^{166}$Yb, $^{169}$Yb, $^{175}$Yb, $^{88}$Y, $^{90}$Y, $^{62}$Zn and $^{65}$Zn. Preferably the radioisotope is $^{131}$I, $^{125}$I, $^{123}$I, $^{111}$I, $^{99m}$Tc, $^{90}$Y, $^{186}$Re, $^{188}$Re, $^{32}$P, $^{153}$Sm, $^{67}$Ga, $^{201}$Tl, $^{77}$Br, or $^{18}$F, and is imaged with a photoscanning device. Procedures for labeling biological agents with the radioactive isotopes are generally known in the art.

The imaging agent may carry a bioluminescent or chemiluminescent label. Such labels include polypeptides known to be fluorescent, bioluminescent or chemiluminescent, or, that act as enzymes on a specific substrate (reagent), or can generate a fluorescent, bioluminescent or chemiluminescent molecule. Examples of bioluminescent or chemiluminescent labels include luciferases, aequorin, obelin, mnemiopsin, berovin, a phenanthridinium ester, and variations thereof and combinations thereof. A substrate for the bioluminescent or chemiluminescent polypeptide may also be utilized in a method of the invention. For example, the chemiluminescent polypeptide can be luciferase and the reagent luciferin. A substrate for a bioluminescent or chemiluminescent label can be administered before, at the same time (e.g., in the same formulation), or after administration of the agent.

The imaging agent may include a paramagnetic compound, such as a polypeptide chelated to a metal (e.g., a metalloporphyrin). The paramagnetic compound may also include a monocrystalline nanoparticle, e.g., a nanoparticle including a lanthanide (e.g., Gd) or iron oxide; or, a metal ion such as a lanthanide. Examples of elements that are useful in magnetic resonance imaging include gadolinium, terbium, tin, iron, or isotopes thereof.

Whole body imaging techniques using radioisotope labeled agents can be used for locating diseased cells and tissues (e.g., primary tumors and tumors which have metastasized). In some cases, the labeled agents for locating the tumor tissue or cells are administered intravenously. The bio-distribution of the label can be monitored by scintigraphy, and accumulations of the label are related to the presence of SIRPgamma or other tumor markers. Whole body imaging techniques are described in, e.g., U.S. Pat. Nos. 4,036,945 and 4,311,688.

An image can be generated in a method of the invention by computer assisted tomography (CAT), magnetic resonance spectroscopy (MRS) image, magnetic resonance imaging (MRI), positron emission tomography (PET), single-photon emission computed tomography (SPECT), or bioluminescence imaging (BLI) or equivalent.

Computer assisted tomography (CAT) and computerized axial tomography (CAT) systems and devices well known in the art can be utilized in the practice of the present invention. (See, for example, U.S. Pat. Nos. 6,151,377; 5,946,371; 5,446,799; 5,406,479; 5,208,581; and 5,109, 97.) The invention may also utilize animal imaging modalities, such as MicroCAT™. (ImTek, Inc.).

Magnetic resonance imaging (MRI) systems and devices well known in the art can be utilized in the practice of the present invention. For a description of MRI methods and devices, see, for example, U.S. Pat. No. 6,151,377. MRI and supporting devices are commercially available, for example, from Bruker Medical GMBH; Caprius; Esaote Biomedica; Fonar; GE Medical Systems (GEMS); Hitachi Medical Systems America; Intermagnetics General Corporation; Lunar Corp.; MagneVu; Marconi Medicals; Philips Medical Systems; Shimadzu; Siemens; Toshiba America Medical Systems; including imaging systems, by, e.g., Silicon Graphics.

Positron emission tomography imaging (PET) systems and devices well known in the art can be utilized in the practice of the present invention. For example, a method of the invention may use the system designated Pet VI located at Brookhaven National Laboratory. For descriptions of PET systems and devices, see, for example, U.S. Pat. No. 6,151, 377. Animal imaging modalities such as micro-PETs (Concorde Microsystems, Inc.) can also be used in the invention.

Single-photon emission computed tomography (SPECT) systems and devices well known in the art can be utilized in the practice of the present invention. (See, for example, U.S. Pat. Nos. 6,115,446; 6,072,177; 5,608,221; 5,600,145; 5,210,421; 5,103,098.) The methods of the invention may also utilize animal imaging modalities, such as micro-SPECTs.

Sensitive photon detection systems can be used to detect bioluminescent and fluorescent proteins externally; see for example, Contag (2000), Neoplasia 2:41-52; adn Zhang (1994), Clin. Exp. Metastasis, 12:87-92. The methods of the invention can be practiced using any such photon detection device, for example, an intensified charge-coupled device (ICCD) camera coupled to an image processor. Photo detection devices are also commercially available from Xenogen, Hamamatsue.

Examples

The following examples are offered to illustrate, but not to limit, the claimed invention.

Example 1. Materials and Method

The materials and methods described in this example were used in performing the experiments described in Examples 2-6. Reference should also be made to the Brief Description of the Drawings for experimental details.

Cell lines and cell culture: Human lung cancer cell lines 293T, Mouse RAW264.7 macrophages, A549 cells were obtained from the American Type Culture Collection (ATCC, Rockville, MD, USA). 293T, Mouse RAW264.7 macrophages and A549 cells were cultured in Dulbecco's modified Eagle's medium (DMEM) containing 10% fetal bovine serum (FBS) in a humidified 37° C. incubator with 5% $CO_2$ atmosphere. Tumor sphere culture was performed as described previously. Cells were grown in serum-free medium (SFM) composed of DMEM/F12 (Gibco, USA), basic fibroblast growth factor (bFGF, 20 ng/ml; Upstate, USA), epidermal growth factor (EGF, 20 ng/ml; Sigma-Aldrich, USA), and B27 supplement (20 µl/ml; Life Technologies, USA). Cancer cells were transduced with lentiviruses which were generated with a pCDH-CMV-MCS-EF1 lentiviral vector expressing a luciferase-eGFP fusion protein and were sorted by flow cytometry with BD FACSAria II cell sorters for GFP cells.

Lentiviral shRNA construction and infection: Potential target sequences for *Homo sapiens* SIRPgamma mRNA (NM_080816) were screened, and the primers targeting human SIRPgamma short hairpin sequences were designed. The forward and reverse primers were digested, annealed, and cloned in to Xhol site of the vector. After confirmation of DNA sequences, the vectors were infected into 293T cells to produce viruses. Approximately $1\times10^5$ cells were seeded in 2 ml DMEM medium with 10% FBS in 6-well plates 24 hours prior to infection. The resulting lentiviral SIRP-gamma-shRNA and control-shRNA were used to infect A549 cell line. A control-shRNA was designed by mutating the antisense nucleotides in the Sirpg-shRNA sequence.

cDNA microarray and data analysis: Human genome microarray analysis was performed and genes were determined to be differentially expressed when logarithmic gene expression ratios were more than 2-fold different, and the p-values were less than 0.05. For data validation, mRNA levels of the interested genes were analyzed by quantitative RT-PCR. All target genes and primer sequences used for validation will be provided upon request. To examine genes that might be systemically altered, both Kyoto Encyclopaedia of Genes and Genomes (KEGG) Pathways Analysis and Gene Set Enrichment Analysis (GSEA) were used for pathway analysis.

Flow Cytometry Analysis: Flow cytometry was performed on a FACS Calibur (BD Biosciences, USA). Cancer cells were dissociated into single-cell suspension that was washed and incubated in staining solution containing 1% BSA and 2 mM EDTA with the fluorescent monoclonal antibodies or respective isotype controls at 4° C. for 30 min. Antibodies were conjugated with FITC, PE, or fluorophore conjugated secondary antibodies were used. SYTOX Blue was used to exclude dead cells. The cells were then analyzed and results were calculated using Cell Quest software (BD Biosciences, USA).

Cell Proliferation assay: Adherent monolayer cells were seeded in 96-well plates at $2\times10^3$ per well in 0.2 ml DMEM medium containing 10% FBS. The cells were incubated at 37° C. and 5% $CO_2$ for 8 days. In the following 8 days, MTT assay was performed each day. MTT solution (50 µl, 2 mg/mL, Sigma-Aldrich, USA) was added to cell culture followed by incubation at 37° C. for 4 h. Culture medium was replaced by 150 µl DMSO and optical density was measured at 570 nm with an automated BioTek Microplate Readers and Spectrophotometers (Bio-Rad, USA).

Self-renewal assay: Adherent monolayer cancer cells were dissociated into single-cell suspension. Equal number of cells was seeded in a 96-well plate. Cells were cultured in stem cell media to obtain primary spheres and second generation spheres. Floating spheres and the total cell numbers were counted under light microscopy.

Colony formation assay: For colony formation, cells were dissociated into single-cell suspension and plated into 4.8 mm dishes at a density of 400 cells/well in DMEM medium with 10% FBS. The plates were further incubated for 14 days at 37° C. with 5% $CO_2$ until colonies were visible. The colonies were stained with 0.01% crystal violet for 5 min and counted under inverted microscopy. The colony formation efficiency was assessed by the ratio of the colony numbers to plated cell numbers in each well.

Phagocytosis assay: FACS-based phagocytosis assays were performed to evaluate the phagocytic abilities of macrophages. Mouse RAW264.7 macrophages or bone marrow derived macrophages (BMDM) were harvested before co-incubation, mouse macrophages were incubated with serum-free DMEM for 12 h. Then, $2\times10^5$ macrophages and equal number of target cancer cells were added in per FACS tube. Mixed the target cells with macrophages and added the total volume up to 200 µl for per tube. All tubes were incubated at 37° C. for 2 h to 24 h with the indicated conditions. After co-incubation, cells were incubated with PE or PE cy7-conjugated anti-mouse F4/80 antibody to stain macrophages for 30 mins. cells were washed thoroughly with serum free-DMEM for 3 times and suspended with 200 µl of serum free-DMEM. Subsequently, the phagocytosis was examed under a BD FACS using an enhanced green fluorescent protein (GFP) or PE or PE-cy7 filter set. At least 1000 macrophages were counted per tube. Macrophages that phagocytosed target cells were F4/80$^+$ and GFP, and the phagocytic index based on FACS was calculated as the number of F4/80 GFP cells divided by the number of F4/80$^+$ cells. In each experiment, phagocytic indexes were normalized to the maximal indexes.

Patient samples: The tissues used in this study were collected from a total of 182 patients with primary lung adenocarcinoma (LAC) who received surgical resection at the Third Military Medical University, China. All patients consented before surgery or any other clinically indicated procedure to the study. Tumor grades were defined according to the criteria of the World Health Organization. The Tumor-Node-Metastasis (pTNM) status of all LACs was assessed according to the criteria of the sixth edition of the TNM classification of the International Union Against Cancer. The clinico-pathological characteristics of the patients were also noted. The study was approved by the Medical Ethics Committee of Cancer Center of the Third Military Medical University.

Immunohistochemistry: Immunohistochemical staining of tumor xenografts was performed on sections using streptavidin-biotin peroxidase complex (SABC) method as described previously. Briefly, xenograft samples were fixed in 4% paraformaldehyde at 4° C. for 72 hrs and embedded in paraffin. The paraffin sections were incubated with primary antibodies at 4° C. overnight. The slides were then reacted with biotinylated goat anti-mouse/rabbit IgG and avidin-biotin complex (ABC). For visualization of the antibody-antigen complex, chromogen reaction was carried out with diaminobenzidine (DAB) and the slides were examined under a light microscope. For quantification, IPP software (image-pro plus 6.0) was used to analyze the optical density of the images within 5 random fields at 400× magnification. The average optical density (AOD), namely IOD/area, was calculated. IHC staining intensity was independently scored by two anatomical pathologists. The staining intensity (negative=0, weak=1, moderate=2, or strong-3 scores) and the proportion of immunostaining positive cells of interest (<25%=1, 25 to 50%=2, >50% to <75%=3, 75%=4) were scored. The immunostaining was semi-quantitatively categorized by combining the intensity and the quantity scores, which yield a staining index (values from 0 to 12). The staining index of 5-12 was regared as high expression, while staining index of 0-4 was considered as low expression.

Immunofluorescence (IF) Staining: For immunofluorescence staining, cells were attached to poly-L-lysine-coated coverslips in DMEM containing 10% FBS for 24 hrs, and subsequently fixed in 4% paraformaldehyde for 20 min. Both monolayer cells and LACSLCs were blocked with pre-immune goat serum at 37° C. for 30 min, and then incubated with primary antibodies at 4° C. overnight. Antibodies used in the experiments will be provided upon request. The cells were subsequently washed in PBS and incubated at 37° C. for 1 hr with Cy3 or Cy5-conjugated goat anti-rabbit or anti-mouse IgG antibodies (1:200; Beyotime). Nuclei were counterstained with Hochest 33258 and observed under laser confocal scanning microscopy (Leica TCS-SP5, Germany). Additionally, freshly frozen human surgical biopsy specimens obtained from eight LAC patients were used in immunofluorescence staining to detect protein expression.

Tumor models/In vivo tumorigenesis and metastasis assays: A549 cells that had been transfected to stably express firefly luciferase (Xenogen) were infected with lentiviruses carrying empty vector, SIRPgamma expression construct, control shRNA, sh-Sirpg. Cancer cells were mixed with Matrigel (1:1) and inoculated into the abdominal mammary fat pad ($1 \times 10^6$ cells) of 6-week-old immunodeficient female nude mice (n=5) or injected into the lateral tail vein ($1 \times 10^5$ cells) of 6-week-old female SCID mice (Center of Experimental Animals, Third Military Medical University). Mice were monitored every week for the appearance of subcutaneous tumors. At the end of 7 weeks, mice were sacrificed, and tumor xenografts were removed, tumor volume (TV) and tumor weight were measured. Tumor volume (TV) was calculated using the following formula: TV (mm$^3$) =d$^2$×D/2, where d and D represent the shortest and the longest diameters.

Western Blot: Cell lysates of cancer cells and tissue tumor cells were prepared using RIPA buffer with protease inhibitors and quantified using a BCA protein assay (Pierce, Rockford, IL). Proteins (20 µg) were loaded onto a 10% SDS-poly-acrylamide gel (SDS-PAGE) and transferred onto PVDF membranes (Millipore, USA). Membranes were incubated with TBS blocking buffer containing 2% milk and subsequently incubated with primary antibodies at 4° C. overnight, followed by incubation with horseradish peroxidase-conjugated secondary antibodies against goat or rabbit IgG (1:10000; Invitrogen, USA). Immunoreactive proteins were visualized using SuperSignal West Femto Trial Kit (Pierce, Rockford, IL) by an enhanced chemiluminescence detection system, followed by X-ray film exposure. The signals of proteins of interest were measured by densitometry. β-actin was used as an internal control.

Quantitative Real-Time PCR (qRT-PCR): Total RNA was extracted from cancer cells using Trizol Reagent (Invitrogen, USA). qRT-PCR was performed using SYBR Prime-Script RT-PCR kit (TaKaRa, Japan) on a Rotor-Gene 6000 real-time genetic analyzer (Corbett Life Science, USA). Glyceraldehyde-3-phosphate dehydrogenase (GAPDH) was amplified as an internal control. The PCR protocol included denaturation (95° C. for 2 min), followed by 40 cycles of amplification and quantification (95° C. for 5 s, 55° C.-57° C. for 30 seconds) and melting curve (55° C.-95° C., with 0.5° C. increment each cycle). Each sample was tested at least in triplicates.

Statistical analysis: All experiments were performed in triplicate and repeated at least three times. Data were presented as the mean±S.D. Statistical analysis was performed using SPSS software. Statistically significant difference was assessed by one-way analysis of variance (ANOVA) followed by multiple mean comparisons by Student-Newman-Keul's test. For univariate survival analysis, survival curves were obtained using the Kaplane-Meier method and comparisons were made using log rank test. Multivariate survival analysis was carried out on all parameters found to be significant in univariate analysis using Cox proportional hazards regression model. Statistical difference was considered significant if P-values were <0.05.

Example 2. SIRPgamma Expression in Patient Tumor Samples

More than half of the original tumor biopsies from the group of patients described in Example 1 showed definitive staining for SIRPg, with the adjacent non-tumor tissue generally negative. These tumors were classified as "SIRPg$^{high}$". Immunohistochemistry for SIRPgamma in two representative human lung adenocarcinoma tissue samples is shown in FIG. 2A (SIRPgamma$^{low}$ sample on right and SIRPgamma$^{high}$ on left). The intensity of SIRPgamma expression in tumor and adjacent normal tissue in tissue biopsies from lung cancer cohort was also scored using a relative scoring scale of 1-15. As summarized in FIG. 2B, this analysis shows positive expression of SIRPgamma in >50% of tumors. Adenocarcinomas showed significantly elevated expression relative to adjacent normal tissue (p<0.001). The data are consistent with results of transcriptional profiling. Expression of SIRPgamma protein in tumor specimens was confirmed by Western immunoblotting with a specific monoclonal antibody (not shown). Patients survival (overall survival) in this cohort was tracked. As shown in FIG. 2C, SIRPgamma expression correlates with significantly reduced disease-free survival in the lung adenocarcinoma cohort (p<0.05). Remarkably, disease-free survival of patients with SIRPg$^{high}$ tumors at 5 years post-biopsy was more than 1.5-fold below that of patients with SIRPg$^{low}$ tumors. This striking survival difference was maintained throughout 8 years after initial diagnosis.

These observations suggest that a therapy capable of reversing the pathological effect associated with high SIRP-gamma expression would have the potential to dramatically improve clinical outcomes in adenocarcinoma of the lung, and potentially in other cancers in which SIRPgamma also is expressed.

Example 3. Human Lung Cancer Stem Cells Express Elevated Levels of SIRPg

Cancer stem cells (CSC) enriched from human lung cancer cell lines (data shown for A549 cell experiments) by sphere formation (as shown in FIG. 3A and FIG. 3B) and by selection for ALDH expression (as shown in FIG. 3C and FIG. 3D) were found to express mRNA encoding SIRP-gamma, along with a number of known CSC markers including Nanog, Sox2, and Pou5F1 (Oct4), three stemness transcription factors found in embryonic stem cells and many CSC. The sphere-enriched CSC also showed elevated expression of ALDH, as would be expected. Confocal microscopy of spheres showed concomitant immunofluo-rescent staining for SIRPgamma and CD133, a cell surface marker found on many normal stem cells and CSC popula-tions (data not shown). The degree of enrichment of mRNA is consistent with the presence of roughly 5 percent CSC in the A549 population.

Fluorescence-activated cell sorting (FACS) was used to isolate A549 cells that express SIRPgamma, using a com-mercially available mAb (LSB2.20) that was raised by immunization with SIRPgamma and does not cross react with SIRPalpha or SIRPbeta. These SIRPgamma-positive cells comprised 4.6% of A549 cells from monolayer culture (FIG. 4A). Western blotting showed that they are enriched strongly for SIRPgamma protein, as expected (FIG. 4B). They also show strong enrichment for the stemness tran-scription factors OCT4 and SOX2. In addition, they express much higher levels of CD47 than the SIRPgamma-negative A549 cells (FIG. 4B). Finally, they have a significant growth advantage in culture over the SIRPgamma-negative popu-lation (FIG. 4C).

Example 4. Human Lung CSC Require SIRPgamma for Stem Cell Functions

SIRPgamma-positive cells were assessed for CSC prop-erties and these cells were utilized in knockdown experi-ments by introducing expression of complementary short-hairpin RNA (shRNA). The aim of the experiment was to determine whether the relevant phenotypes depended on SIRPgamma gene expression. shRNAs are an artificial RNA molecule with a tight hairpin turn that can silence target gene expression via RNA interference (RNAi). A549 cells expressing a shRNA against SIRPgamma showed strongly diminished capacity for spheroid formation under conditions in culture that select preferentially for growth of CSC, as shown in FIG. 5A (efficiency of sphere formation) and FIG. 5B (number of cells per sphere).

The same assay for "oncosphere" formation by A549 CSC was carried out in the presence of a monoclonal antibody generated against SIRPalpha (but which likely has some cross-reactivity with SIRPgamma) and a monoclonal anti-body highly specific for SIRPgamma. Sphere formation appeared to be slightly inhibited by the mAb against SIR-Palpha (not statistically significant), but strongly inhibited by the SIRPgamma monoclonal antibody (FIG. 6). Thus, knockdown of SIRPgamma gene expression by shRNA and functional inhibition of SIRPgamma by a monoclonal anti-body both demonstrate the requirement of the target protein for a well-recognized CSC function, namely, anchorage-independent growth.

Figure 7A:
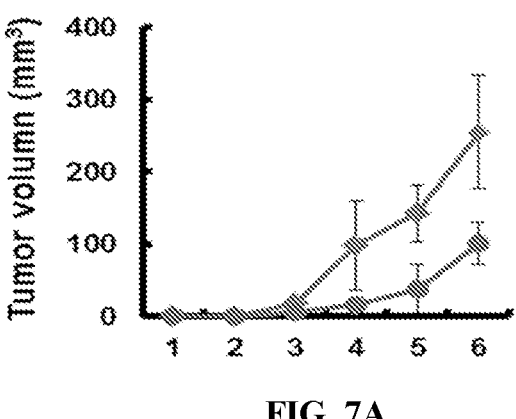
FIG. 7A-7C show that the tumorigenic potential of human lung cancer stem cells depends on SIRPgamma expression according to some aspects of this disclosure. Human A549 lung adenocarcinoma cells were separated into SIRPgamma positive and SIRPgamma negative fractions using FACS, with gating set to select the 4.6% brightest cells (positive) from the remainder of the cell population (negative; see FIG. 4A-4C). Fixed numbers of cells (approx 10e6/mouse) of either fraction were injected into the flanks of immune-deficient mice and tumor volumes were measured over time (weeks).

The cardinal property of CSC is the ability to initiate tumors efficiently. For human cancers this can be assessed in a xenograft assay in immune-deficient mice. In a primary tumor initiation assay with 1 million ($1\times10^6$) flank-injected cells, we compared tumor growth for SIRPgamma-positive versus SIRPgamma-negative cells selected by FACS from adherent A549 cells. We observed that SIRPgamma-positive cells initiate tumors much more rapidly than the SIRPg-negative population (FIG. 7A). Tumor formation by the SIRPgamma-negative cells lagged that of SIRPgamma-positive cells by approximately 2 weeks. This is consistent with the approximately 20-fold enrichment of CSC (tumor-initiating cells) in the SIRPgamma-positive population.

Figure 7B:
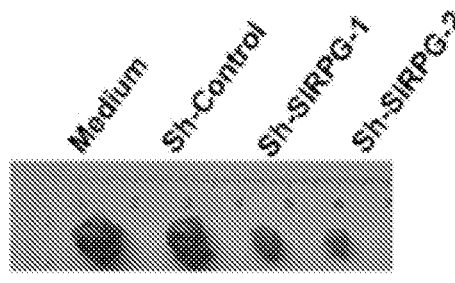
Figure 7C:
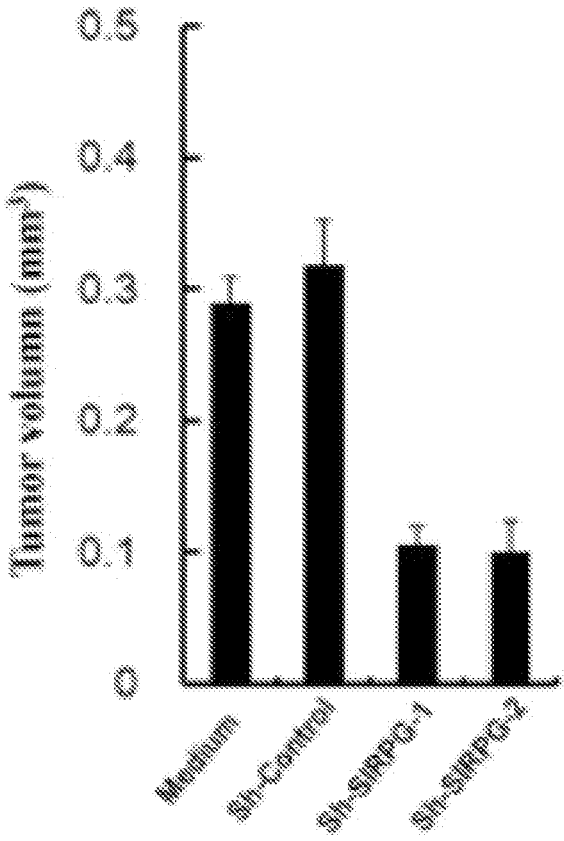

To determine whether SIRPgamma is required for the efficient tumor initiation by A549 CSC, we utilized shRNA introduced by a lentiviral vector to inhibit SIRPgamma gene expression and compared the rate of tumor initiation and growth by the engineered cells. Grown tumors are shown in FIG. 7B and measurements of tumor volume are shown in FIG. 7C. We observed that knockdown of SIRPgamma by each gene-specific shRNA reduced the tumorigenic potential of the CSC to about the level of the SIRPgamma negative FACS-selected population shown in FIG. 7A. These data provide compelling evidence that SIRPgamma is essential for "stemness" of CSC in the A549 human lung adenocar-cinoma cell line. It is likely that SIRPgamma actually is also necessary for survival of the CSC, but this point is not tested rigorously by the experiment shown here. Note further that this experiment measures only the effect of inhibition of SIRPgamma on the intrinsic survival, growth, and tumori-genic potential of the lung cancer CSC. Any additional impact of immune modulation, i.e. restoring sensitivity to killing by phagocytic macrophages and/or cytotoxic T lym-phocytes, would not be observed in the immune-deficient mouse strain used as host in these experiments. (See FIG. 12A-12B for an in vitro demonstration of the impact of SIRPgamma knockdown on immune modulation).

A further in vivo study was conducted to test the ability of A549 cells injected intravenously to form aggressive lung tumors in immune-deficient mice. This assay provides insights into the stemness and metastatic potential of CSC. shRNA was used to assess the effect of knocking down either SIRPgamma gene expression or the expression of the transcription factor YAP1, the activity of which depends on SIRPgamma in A549 cells. Knocking down either SIRP-gamma or YAP1 protein levels caused a dramatic decrease in the tumor burden in the lung. This is shown by imaging individual animals to detect the mass of luciferase-labeled tumor cells, by gross photography of the lungs, and by measurement of the lung weights (FIG. 8).

Taken together the in vitro and xenograft data provide compelling evidence suggesting that SIRPgamma is essen-tial for stemness of CSC in the A549 human lung adeno-carcinoma cell line. It is likely that SIRPgamma actually is also necessary for survival of the CSC, but this point is not tested rigorously by the experiments shown here.

Note further that these data reflect only the role of SIRPgamma in the intrinsic survival, growth, and tumori-genic potential of the lung cancer CSC. The additional potential impact of overcoming immune checkpoints would likely be masked because immune-deficient mice necessar-ily were used in these experiments.

Figure 9A:
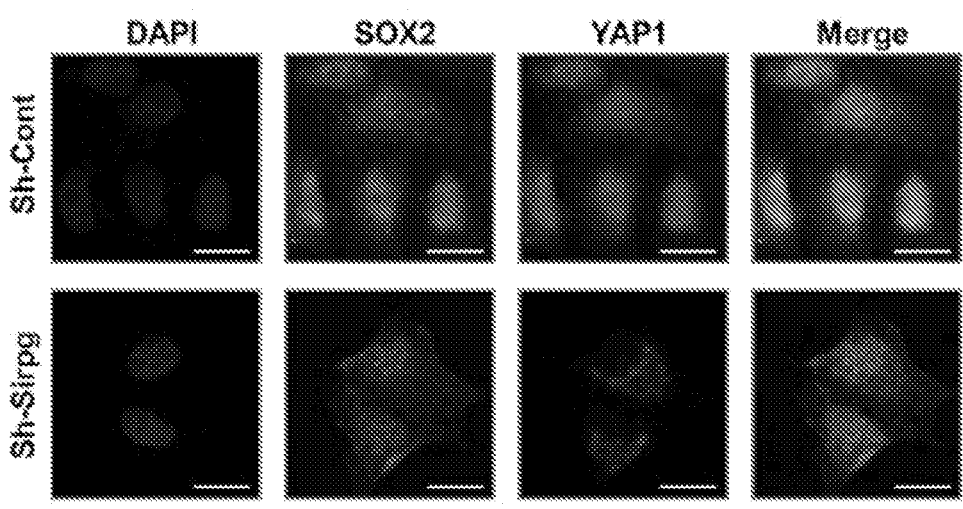
FIGS. 9A-9C show that YAP1 phosphorylation is up-regulated by shRNA-mediated inhibition of SIRPgamma expression in human NSCLC cells, leading to translocation of the protein from nucleus to cytoplasm, according to some aspects of this disclosure.

Example 5. SIRPgamma Regulates Stemness Transcription Factors and Hippo/Yap Pathway Validation of SIRPgamma as a target for cancer therapy is supported by mechanistic understanding of its role in promoting the stemness properties of CSC, as well as its potential role in immune modulation. Transcriptional profiling of A549 adenocarcinoma CSC treated with shRNA-SIRPgamma to knock down expression of SIRPgamma indicated changes in global gene expression consistent with inhibition of activity of YAP1 (yes-associated protein 1), a known oncogene. It also appeared that cells lost the expression of genes directly under control of "stemness" transcription factors (e.g., Pou5F1/Oct4, Sox2, Nanog). To assess possible mechanisms for the linkage of SIRPgamma to activity of these key transcription factors, cells treated with shRNA-SIRPgamma or the shRNA-Control (luciferase) were examined for the subcellular localization of the SOX2 and YAP1 transcription factors (FIG. 9A). In the cells treated with shRNA-Control, both SOX2 and YAP1 were localized almost exclusively in cell nuclei (five representative nuclei are shown in the top panel of 4 images), demonstrating active participation in regulation of the genes transcribed under their control. By contrast, knockdown with shRNA-SIRPgamma induced a shift in the localization of both SOX2 and YAP1 from the nucleus to the cytoplasm, consistent with their functional inactivation (two representative nuclei shown in the bottom panel of 4 images).

Figure 1B:
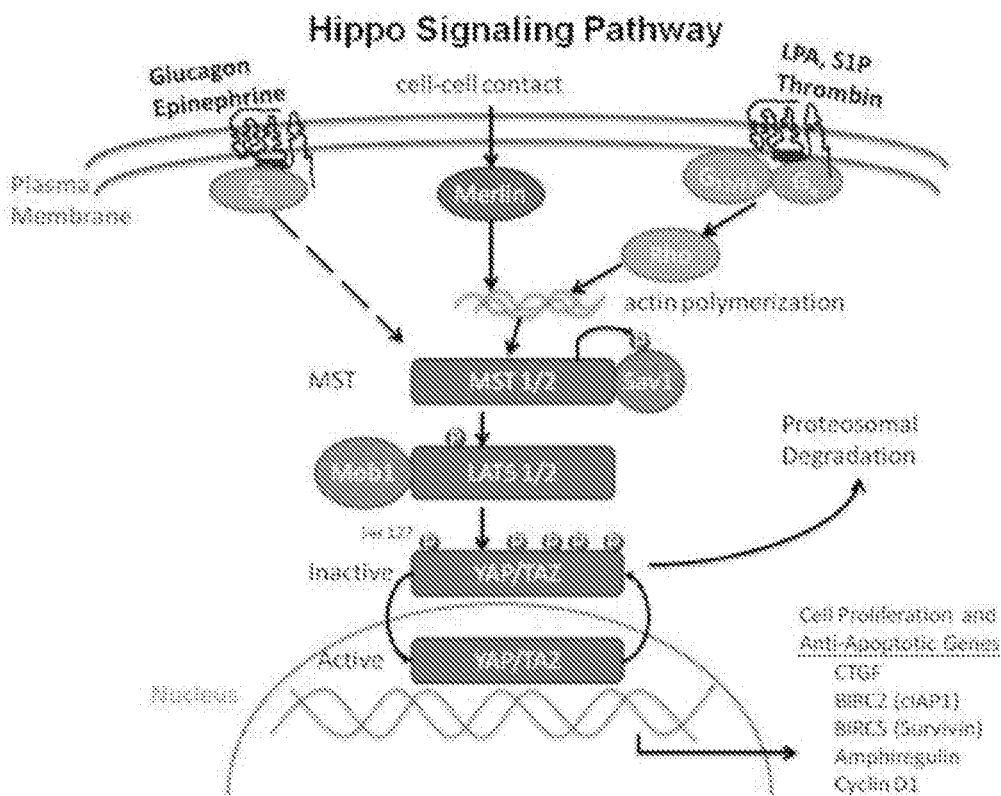
FIG. 1B shows a schematic overview of how the Hippo signaling pathway regulates translocation of YAP/TAZ to the nucleus, thereby activating cell proliferation and anti-apoptotic genes along with genes required for CSC function.

YAP1 is known to function as a transcriptional co-activator. Through interaction with the TEAD family of transcription factors (the major factors interacting with TAZ) and other transcription factors, the proto-oncogene protein YAP1 promotes the expression of genes which promote cell proliferation and oncogenesis, and inhibit apoptosis. YAP is a target for inhibition by the Hippo tumor suppressor pathway (FIG. 1B). Hippo activity leads to phosphorylation of YAP1 that drives its exit from the nucleus to an inactive state in the cytoplasm. Thus, it is reasonable to hypothesize that knockdown of SIRPgamma protein causes inactivation of YAP, marked by its transit from nucleus to cytoplasm, via activation of the Hippo tumor suppressor signaling pathway.

Direct evidence for activation of the Hippo pathway was obtained by assessment of the levels and phosphorylation state of the proteins involved in signal transduction linking cell surface receptors to YAP. We focused on the serine/threonine protein kinase Mst1 which (along with MST2) is the mammalian homolog of the Drosophila Hippo kinase, and on LATS1 (an NDR/LATS protein kinase) which is a substrate for MST1/2.

Figures 9B, 9C:
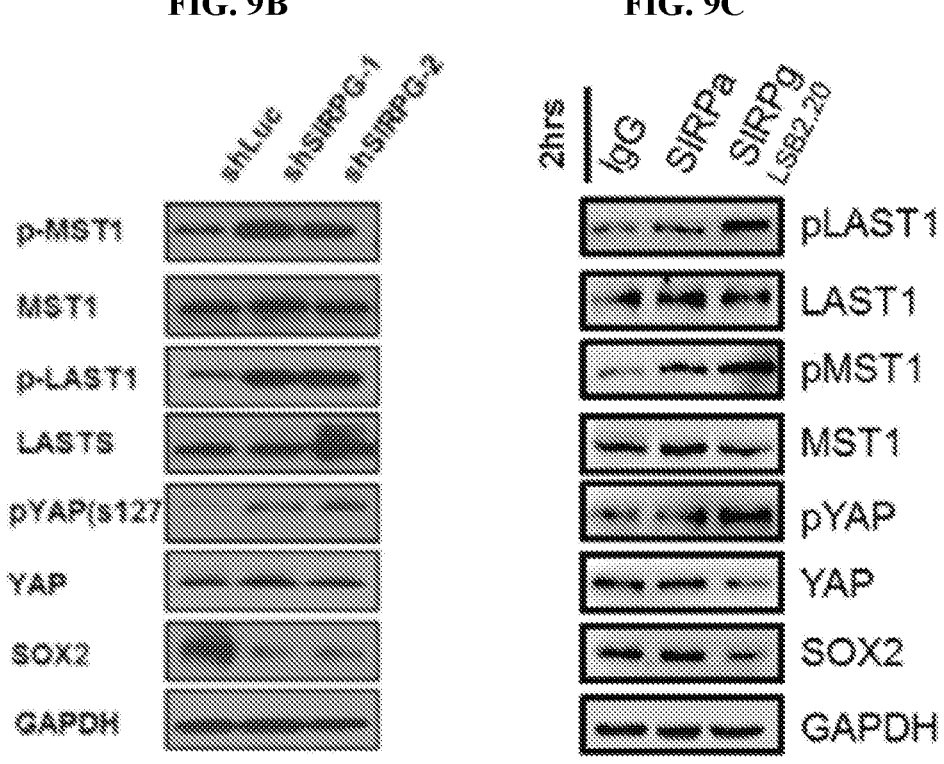

As shown in FIG. 9B, when SIRPgamma protein expression is inhibited by either of the two specific shRNAs, compared to a negative control shRNA (shLuc to luciferase) the levels of phosphorylated MST1 and LATS1 increase sharply. These are the final two components of the protein kinase cascade in the Hippo signaling pathway, directly upstream of YAP, which are known to regulate YAP activity via its phosphorylation Consistent with activation of these two protein kinases, the level of YAP protein phosphorylated on residue Ser127 also increases substantially. The pYAP (S127) phosphorylated form is known to associate with a 14-3-3 protein, leading to sequestration of the YAP protein in the cytoplasm away from its site of activity in the nucleus, as we observed (FIG. 9A). Thus, when SIRPgamma expression is decreased the YAP1 protein in A549 cells is functionally inactivated via the Hippo pathway kinase cascade. The experiment also confirms the loss of the SOX2 transcription factor, consistent with its transport out of the nucleus and subsequent degradation.

A key proof of concept experiment is to determine whether binding of a mAb to the proposed therapeutic target also can activate the Hippo pathway, leading to functional inactivation of YAP. We indeed found that incubation of A549 cells with the SIRPg-specific mAb LSB2.20 for 2 hours precisely mimics the effect of knocking down SIRPgamma expression with shRNA (FIG. 9C). Again we observe robust activation of Hippo pathway, manifested by elevated phosphorylation of two protein kinases (pMST1 and PLATS1) and of YAP (pYAP). As with SOX2, the translocation of YAP from the nucleus to cytoplasm also appears to lead to some degradation of the protein (note bands labeled SOX2 and YAP). A SIRPa mAb (SE7C2) thought to be only weakly cross-reactive with SIRPgamma yields minimal activation of Hippo signaling (possibly a slight elevation of pMST1 and pLATS1).

The turn-off of YAP function when SIRPgamma is inhibited by either shRNA or a specific mAb is significant for target validation because numerous reports associate elevated YAP expression and/or activity with poorer clinical outcomes in lung adenocarcinoma patients. These findings are consistent with YAP's ability to promote tumor cell survival, growth, metastasis, and resistance to chemotherapy. Conversely, in a variety of cancer models inactivation of the YAP/TAZ transcriptional module reverts principal cancer features such as a cancer stem cell properties, epithelial-mesenchymal transition (EMT), increased migration and resistance to anoikis (apoptosis induced by insufficient attachment of cells to a substrate) and increased potential for metastasis, and induced expression of YAP can trigger transition of normal epithelial cells into metastatic cells via EMT and can confer stem cell characteristics. (Moroishi et al., The emerging roles of YAP and TAZ in cancer. *Nat Rev Cancer* 2015; 15:73-9, page 75).

The findings that SIRPgamma is required for efficient oncosphere formation by A549 CSC (FIG. 5A-5B), and that a mAb against this target can inhibit sphere formation (FIG. 6) are consistent with the turnoff of Yap and support the proposed therapeutic approach. The data indicate that a mAb to the target should be able to induce apoptosis of CSC and potentially of bulk tumor cells in SIRPgamma-positive tumors. The observations using shRNA on tumor initiation and growth in the lung after intravenous administration also are entirely consistent with a major role for SIRPgamma in the activation of the YAP proto-oncogene. The data again documents the ability of a specific mAb to block this activation and thereby reverse the stemness and promote the apoptosis of lung adenocarcinoma CSC.

Example 6. SIRPgamma Regulates CD47 Expression and Phagocytosis of Lung Adenocarcinoma Cells This example describes experiments conducted to investigate the role of SIRPgamma in the regulation of expression by CSC of CD47. Many tumor cell types express this cell surface receptor at elevated levels, and that its interaction with SIRPa on macrophages activates "don't eat me" anti-phagocytic signaling.

The results showed that binding of SIRPgamma by either of two specific mAbs (LSB2.20 and OX119) causes by 24 hours a substantial decrease in the level of CD47 mRNA and protein expression by A549 cells. Representative data on mRNA changes measured at 48 hours after exposure to LSB2.20 are presented in FIG. 10A and FIG. 15A. Expression of the stemness transcription factor SOX2 is reduced significantly, consistent with data presented earlier. Similarly, CD47 mRNA is reduced by more than 2-fold. In addition we note a striking reduction in expression of mRNA for the pro-inflammatory cytokine IL1b and a significant decrease for GM-CSF.

The knockdown of SIRPgamma gene expression using three different shRNA constructs confirmed the strong dependence of CD47 expression by A549 cells on the presence of SIRPgamma. Two constructs (designated Sh-SIRPG-77 and Sh-SIRPG-79) caused almost complete suppression of SIRPgamma mRNA, while Sh-SIRPG-78 reduced its expression by about 90 percent (FIG. 11A and FIG. 11B). The levels of SIRPgamma protein observed in this experiment were proportional to SIRPgamma mRNA in cells carrying the shRNA constructs (FIG. 11B, left side).

Reciprocally, the overproduction of SIRPgamma in A549 cells induced by transduction with a lentiviral vector carrying a SIRPgamma cDNA construct caused a parallel strong increase in CD47 protein expression (FIG. 11B, right side).

Analysis by flow cytometry reveals that the large majority of A549 cells (>95%) express CD47. By contrast, only about 5% of the cells in the line, when grown under standard adherent conditions, stain positively for SIRPg. Thus, the robust inhibition of CD47 expression by the anti-SIRP-gamma mAb and SIRPgamma-specific shRNAs initially seems paradoxical.

Figure 10A:
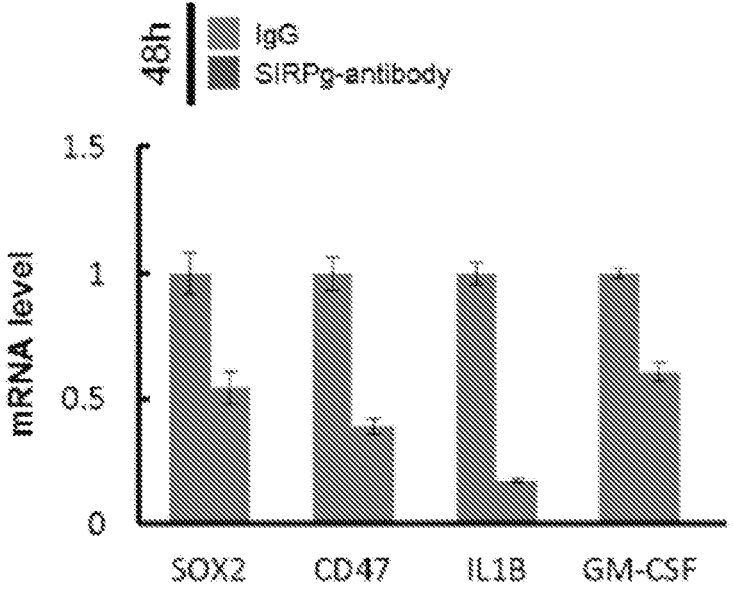
FIG. 10A shows downregulation of CD47 and cytokines by SIRPgamma-specific mAb according to some aspects of this disclosure. A549 cells were incubated with mAb LSB2.20 to SIRPgamma or a control IgG at 20 mg/ml. The mRNA levels of selected YAP target genes were assessed after 48 hours by qRT-PCR. SOX2 and CD47 are described in the text. IL1b=interleukin 1 beta. GM-CSF=granulocyte macrophage colony-stimulating factor. In the graph, for each mRNA assessed, the bar on the left represents the control IgG treated sample and the bar on the right represents the SIRPgamma-mAb treated sample.
Figure 10B:
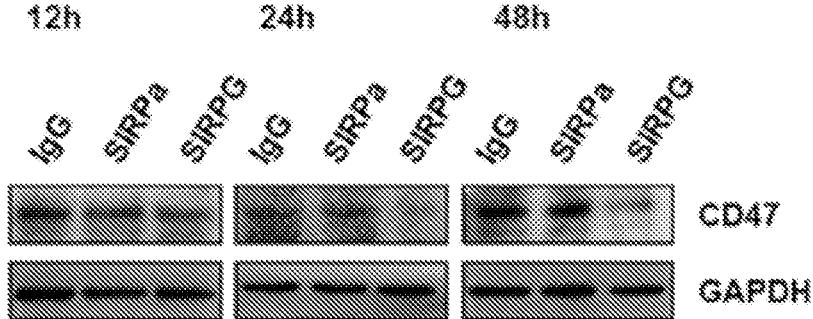
FIG. 10B shows regulation of CD47 protein expression by SIRP-specific monoclonal antibodies according to some aspects of this disclosure. A549 human lung adenocarcinoma cells were incubated with a control IgG, a monoclonal antibody specific to SIRPalpha (SIRPa, SE7C2), or a monoclonal antibody specific to SIRPgamma (SIRPG; LSB2.20). At 12, 24, and 48 hours, samples were obtained and processed for Western immunoblotting with antibodies for GAPDH (loading control) and CD47.

A resolution to this apparent paradox comes from the data shown in FIG. 10A and FIG. 10B. Expression of mRNA for the cytokines IL1b and GM-CSF declines substantially in A549 cells exposed to a SIRPgamma-specific mAb. This led to hypothesize that IL1b and/or GM-CSF or other cytokine(s) produced by A549 CSC might positively regulate CD47 synthesis in the remainder of the A549 cells through a paracrine mechanism. If so, the consequences for tumor growth and metastasis could be profound. First, as already noted, CD47 would protect the cancer cells from phagocytosis by SIRPalpha-positive macrophages. It might also confer on them a more aggressive cancer phenotype through additional mechanisms. Moreover, the cytokines, especially the proinflammatory IL1b would exert multiple additional effects on the tumor microenvironment such as acceleration of angiogenesis, enhancement of niches for CSC, and suppression of additional components of anti-tumor immunity. A corollary of this line of reasoning is that NSCLC tumors comparable to the A549 cell line, in which only a small percentage of cells are SIRPgamma-positive and which might therefore score as SIRPgamma$^{low}$ in the system described in FIG. 2B and FIG. 2C, could still be good candidates for therapy with an anti-SIRPgamma mAb.

To assess the effect of regulation of CD47 expression by SIRPgamma on the susceptibility of cancer cells to phagocytosis by macrophages, preliminary experiments were conducted using an established murine macrophage line (RAW264.7). As shown in FIG. 12A and FIG. 12B, both the inhibition of SIRPgamma gene expression with shRNA and treatment of cells with an anti-SIRPgamma mAb increased phagocytosis of A549 cells from background level to near the level seen when cells were treated with an anti-CD47 mAb. The combination of anti-SIRPgamma plus anti-CD47 was not significantly different from anti-CD47 alone.

Figure 13:
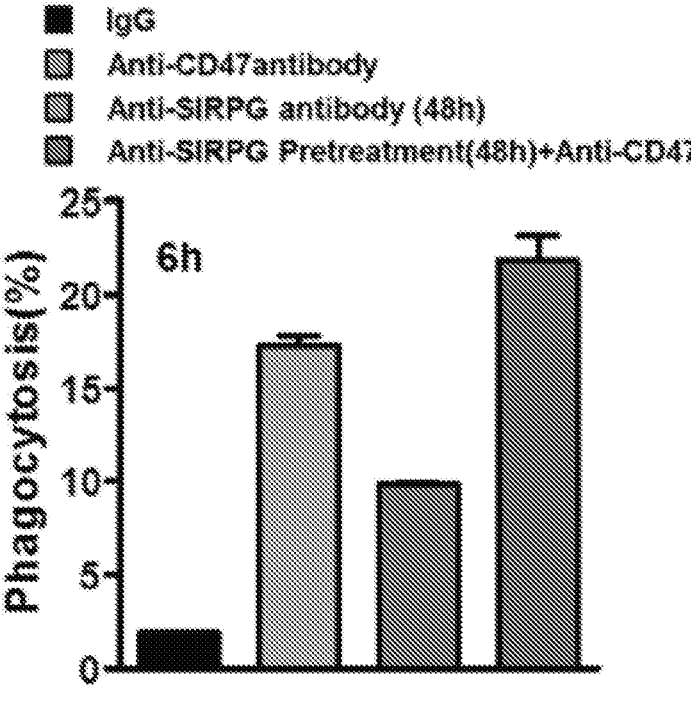
FIG. 13 shows enhanced phagocytosis of lung adenocarcinoma cells by monoclonal antibodies to SIRPgamma and CD47 according to some aspects of the disclosure. Fluorescently labeled (green fluorescent protein, GFP) A549 cells were treated with a blocking mAb to CD47 or a control mAb IgG and co-incubated for 6 hours with an equal number of bone-marrow derived mouse macrophages. Where indicated, the A549 cells were pre-incubated for 48 hours with mAb LSB2.20 to SIRPgamma. Phagocytosis was quantified by flow cytometry using phycoerythrin (PE)-labeled mAb F4/80 to identify macrophages. Phagocytosed cells were identified by double staining for GFP and PE. The four bars, from left to right, represent samples treated with IgG, anti-CD47 antibody, anti-SIRPgamma antibody (48 h), and anti-SIRPgamma pretreatment (48 h) and anti-CD47 antibody, respectively.

When normal murine bone marrow-derived macrophages were tested for phagocytosis of A549 cells, we obtained qualitatively comparable results with both methods of inhibiting SIRPgamma, with a considerably lower background rate of cell engulfment. While these results appear more physiologically relevant, we plan future studies with human macrophages to ensure optimal matching of the CD47 and SIRPalpha and SIRPgamma receptors. As shown in FIG. 13, treatment with a mAb against CD47 greatly enhanced phagocytosis, consistent with numerous published reports. The results showed that the mAb LSB2.20 against SIRP-gamma gave approximately a 5-fold increase in phagocytosis of labeled A549 cells, somewhat less than the effect of blocking CD47. Pretreatment of the cells with mAb to SIRPgamma for 48 hours, followed by treatment with mAb to CD47 gave some further enhancement of phagocytosis over anti-CD47 alone.

Figure 14:
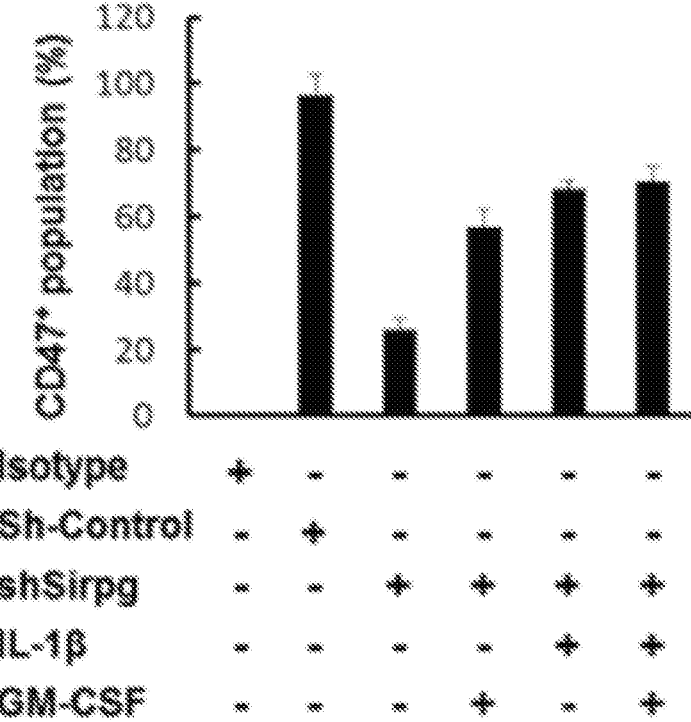
FIG. 14 shows cytokines restore CD47 expression in bulk of A549 cells after knockdown of SIRPgamma expression by shRNA according to some aspects of the disclosure. Percentage of cells staining positively by flow cytometry with mAb to CD47 (Isotype indicates that a nonspecific IgG served as control). With control shRNA, approx. 95% of cells were CD47-positive. SIRPgamma specific shRNA (sh-Sirpg) alone reduced staining to approx. 20% CD47-positive. IL1b, GM-CSF, and the combination substantially restored the percentage of CD47-positive cells.

The following study was conducted to test the hypothesis that agents targeting SIRPgamma on the CSC turn off expression of CD47 in the bulk of SIRPgamma-negative tumor cells through inhibition of cytokine synthesis by the CSC. When A549 cells were treated with shRNA-SIRP-gamma, the fraction of CD47-positive cells fell from nearly 100 percent to approximately 20 percent, as shown in FIG. 14. However, addition of either IL1b or GM-CSF to the shRNA-inhibited cells restored expression of CD47 to 60-75 percent of the population. Addition of both cytokines was about equally effective as IL1b alone. Very similar results were obtained when we treated cells with an anti-SIRP-gamma mAb; CD47 expression was greatly reduced but could be largely restored by the cytokines (data not shown). Taken together, we believe these data support our hypothesis of paracrine regulation of CD47 in the bulk of A549 cells by cytokines produced by the small population of CSC.

To evaluate the significance of the ability of an anti-SIRPgamma mAb turning off YAP function by activation of the tumor suppressive Hippo pathway, a model experiment was carried out as below. This experiment is designed to reinforce the notion that turn-off of YAP should be a primary criterion for a candidate therapeutic mAb, in particular to achieve the desired enhancement of phagocytosis of tumor cells. The same criterion would also apply to attacking the intrinsic stemness and survival of CSC.

Figure 15A:
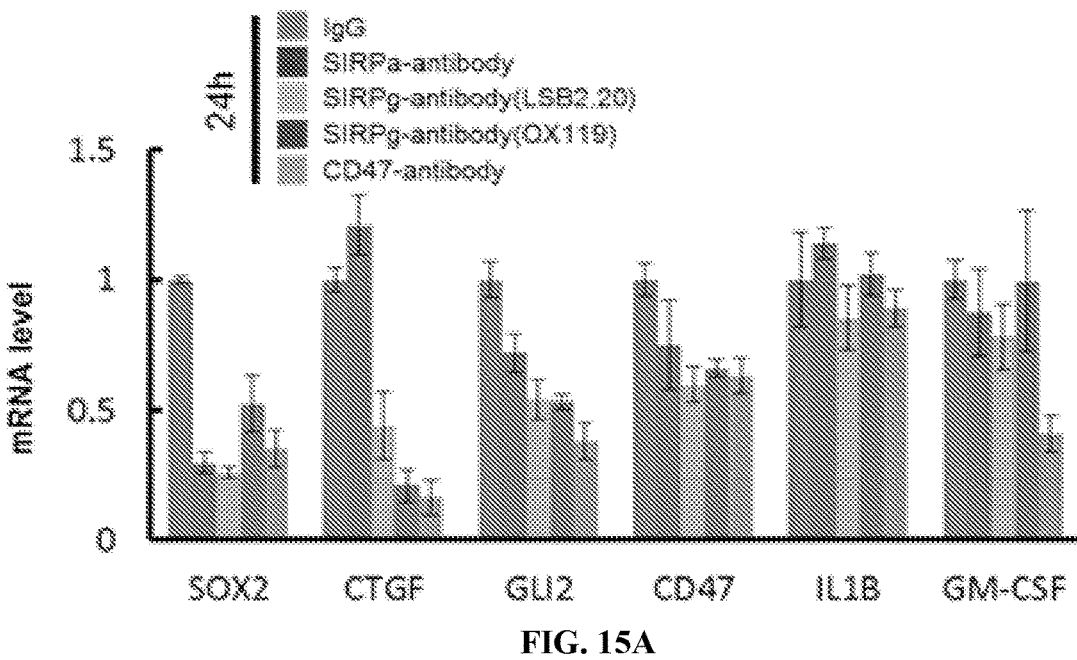
FIG. 15A-15C show that knockdown of YAP1 expression by shRNA promotes phagocytosis, possibly overcoming inhibition by CD47, according to some aspects of this disclosure.

Blocking antibodies against SIRPalpha, SIRPgamma, and CD47, as well as a control IgG were also used to assess the impact on gene expression at 24 hr. As shown in FIG. 15A, SIRPalpha blocking antibody did not significantly impact downstream expression of the genes assessed. However, the SIRPgamma and CD47 antibodies did result in decreased expression of SOX2, CTGF, CLI2, and CD47.

Figure 15B:
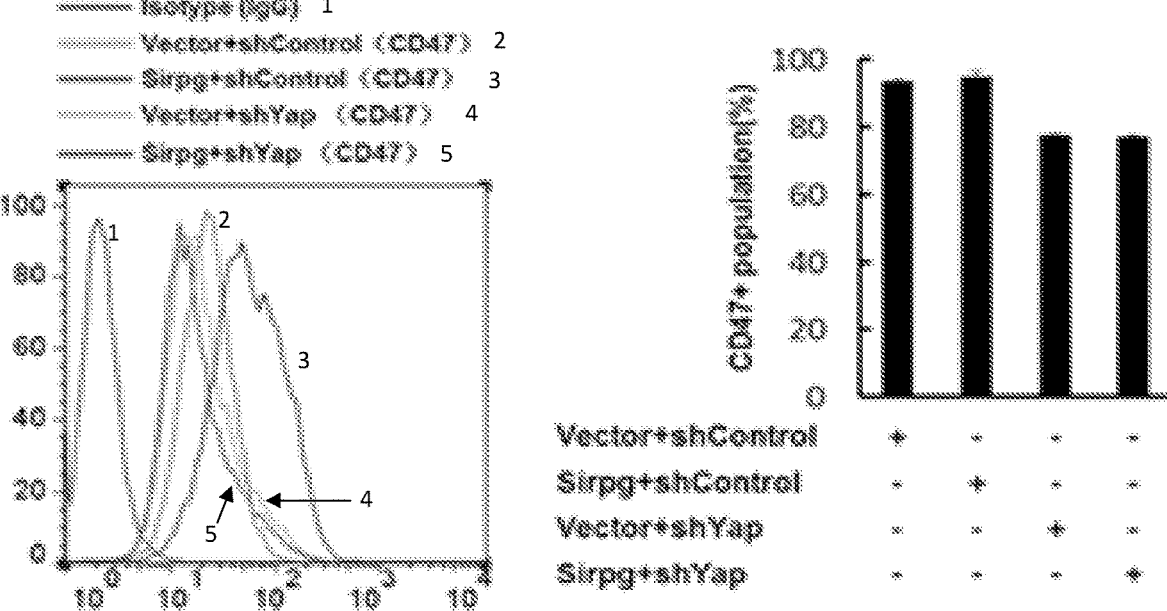
Figure 15C:
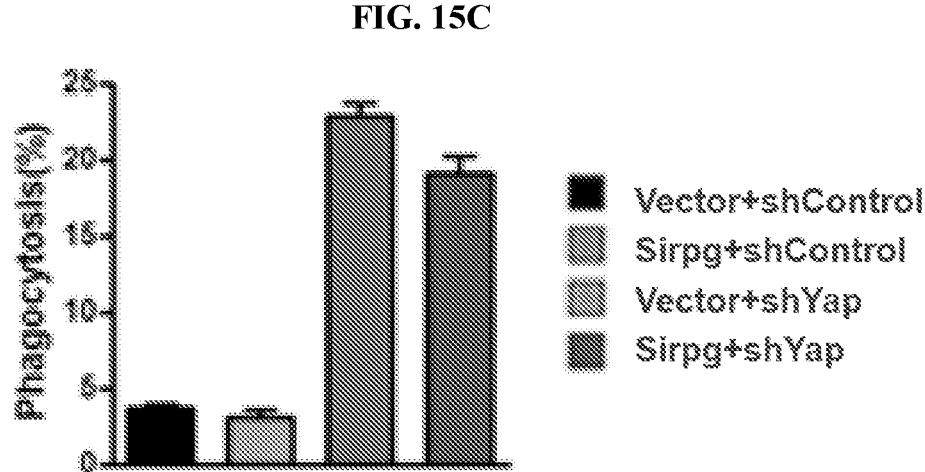
Figure 16A:
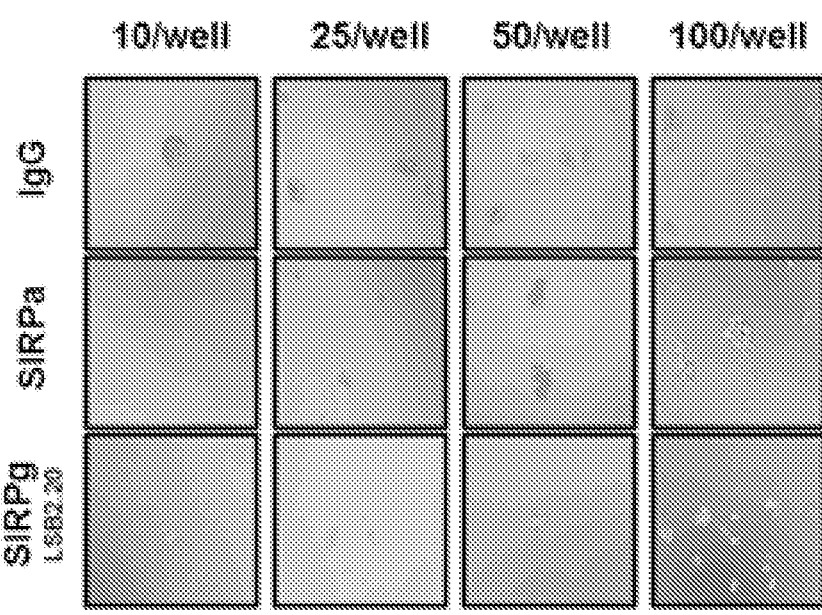
FIG. 16A shows representative images and quantitative analysis, respectively, of the self-renewal capability of A549 cells treatment with antibodies including SIRPalpha specific antibody SE7C2 (20 µg/mL), SIRPgamma specific antibody LSB2.20 (20 µg/mL) and nonblocking control mAb (20 µg/mL), according to some aspects of this disclosure. Cells cultured in serum-free culture media with EGF and bFGF generated non-adherent, multi-cellular spheres. The number of spheres was counted at day 7 and the results are shown in FIG. 6 as described above.
Figure 16B:
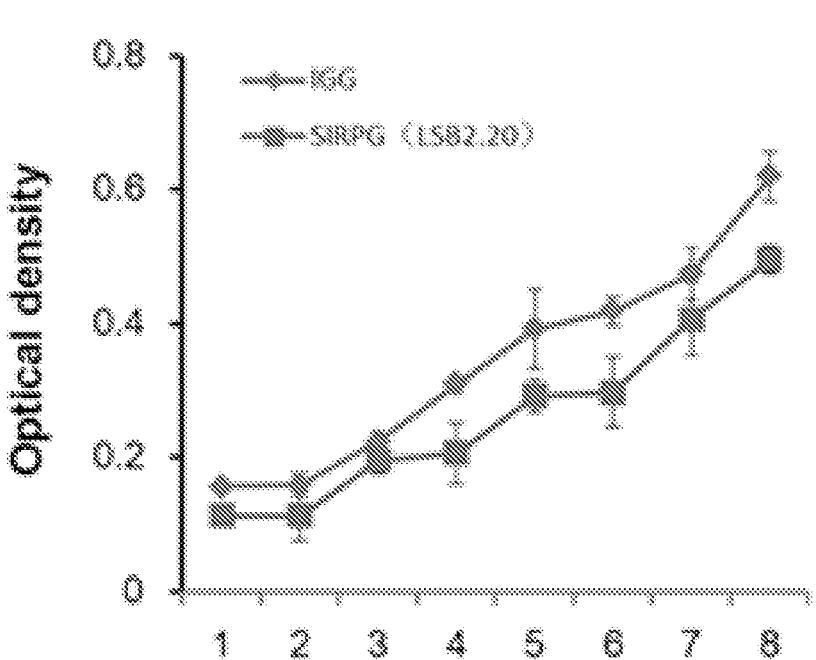
FIG. 16B shows growth curves of A549 cells after treatment with a SIRPgamma specific antibody and a nonblocking control mAb, according to some aspects of this disclosure. Proliferation of A549 cells was inhibited after treatment with SIRPgamma specific antibody LSB2.20 (20 µg/mL) in adherent conditions for four days.
Figure 16C:
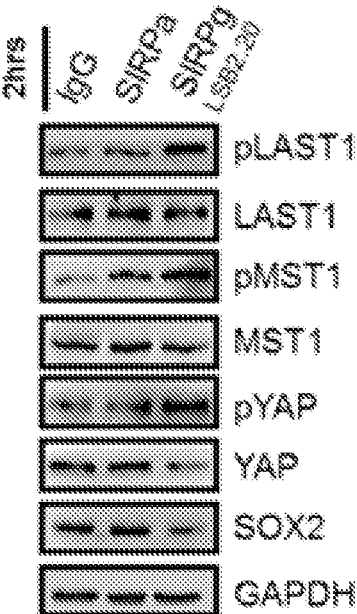
FIG. 16C shows the results of Western blot analysis of protein expression in A549 cells after treatment with SIRPalpha specific antibody SE7C2 (20 µg/mL), SIRPgamma specific antibody LSB2.20 (20 µg/mL), and nonblocking control mAb (20 µg/mL) for 2 hr. Experiments were performed at least in triplicates. Each bar represents the mean±S.E.M.

It was observed that an shRNA specific for YAP1 introduced into A549 cells reduced CD47 expression only to a very modest extent. While nearly 100 percent of cells treated with control shRNA remained CD47-positive, at least 75 percent of those treated with the shRNA-YAP also were CD47-positive by flow cytometry, as shown in FIG. 15B (right side). However, the cells in which YAP expression was knocked down showed greatly enhanced susceptibility to phagocytosis by bone marrow-derived macrophages, despite retaining significant levels of the "don't eat me" signaling protein, as shown in FIG. 15C.

The following experiments was conducted with A549 cells having elevated expression of SIRPgamma in A549 cells via transduction with the lentiviral vector for a full-length SIRPgamma cDNA as described earlier. One might argue that this elevated expression of SIRPgamma effectively converted A549 from a model SIRPg$^{low}$ to a SIRPg$^{high}$ lung adenocarcinoma and that the elevated expression of SIRPgamma could not significantly change the percentage of cells scored as CD47-positive, which was already nearly the entire A549 population. However, introduction of the SIRPgamma expression construct did increase the intensity of staining for CD47 by several-fold. Remarkably, in these cells with significantly elevated SIRPgamma and CD47 expression, introduction of the vector expressing an shRNA against YAP1 again yielded only a modest decrease from nearly 100 percent to about 75 percent CD47-positive cells, but the cells still showed a striking increase in susceptibility to phagocytosis by macrophages, as shown in FIG. 15C.

Therefore, it appears possible that the elimination of CD47 from tumor cells is not the most critical element in overcoming the "don't eat me" signaling that helps to evade host anti-tumor immunity. Some other YAP-dependent factor(s), possibly the cytokines IL1b, GM-CSF, or others, may be required to override the ability of macrophages to phagocytose the tumor cells even when the interaction of tumor-cell CD47 and macrophage SIRPa can occur.

Example 7. SIRPg$^{high}$ Display High Tumorigenic Potential

To explore the role of SIRPgamma in tumor progression, SIRPgamma$^{high}$ and SIRPgamma$^{low}$-cells were sorted using flow cytometry and implanted into mice to establish tumor xenograft models. The assays were performed as follows: SIRPgamma$^{high}$ and SIRPgamma$^{low}$-cells were sorted from A549 monolayer cells by flow cytometry. The serial dilutions of viable cells with equal number (1×10e2; 1×10e3; 1×10e4 and 5×10e4) were diluted in serum-free DMEM medium and injected subcutaneously to four-week-old male nude mice (n=3 each group). Mice were monitored every week for the appearance of subcutaneous tumors. At the end of 7 weeks, mice were sacrificed, and tumor xenografts were removed, tumor volume (TV) and tumor weight were measured. Tumor volume (TV) was calculated using the following formula: TV (mm$^3$)=d$^2$×D/2, where d and D represent the shortest and the longest diameters, respectively.

The results show that SIRPgamma$^{high}$ cells displayed enhanced subcutaneous xenograft growth compared to the SIRPgamma$^{low/-}$ cells in vivo. Serial dilutions were performed to compare the tumorigenicity of SIRPgamma$^{high}$ and SIRPG$^{low/-}$ A549 cells. Sorted SIRPg$^{high}$ and SIRPgamma$^{low/-}$ cells (100, 1000, 10000, and 50000) were subcutaneously injected into the nude mice at body locations as indicated by the dots in FIG. 17A respectively. The results of the tumor cells inoculated into nude mice and the observation of the tumor formation is shown in Table 1. As shown in Table 1, none of the SIRPgamma$^{low/-}$ (SIRPG$^{low/-}$) cells implantations formed xenograft (FIG. 17C), while 50000 SIRPgamma$^{high}$ (SIRP$^{high}$) cells formed xenogranft in most of the recipient mice (FIG. 17B). These results indicate that SIRPgamma$^{high}$ cells can promote tumor growth.

TABLE 1

Tumorigenity of SIRPgamma$^{high}$ and SIRPgamma$^{low/-}$ Tumor Cells

| Injected cell number | Tumor incidence SIRPG$^{high}$ cells | (tumors/injected mice) SIRPG$^{low/-}$ cells |
|---|---|---|
| 5.0 × 10$^4$ | 2/3 | 0/3 |
| 1.0 × 10$^4$ | 0/3 | 0/3 |
| 1.0 × 10$^3$ | 0/3 | 0/3 |
| 1.0 × 10$^2$ | 0/3 | 0/3 |

Example 8. In Vitro Effect of an Anti SIRPgamma Antibody

Figures 18A, 18B, 18C:
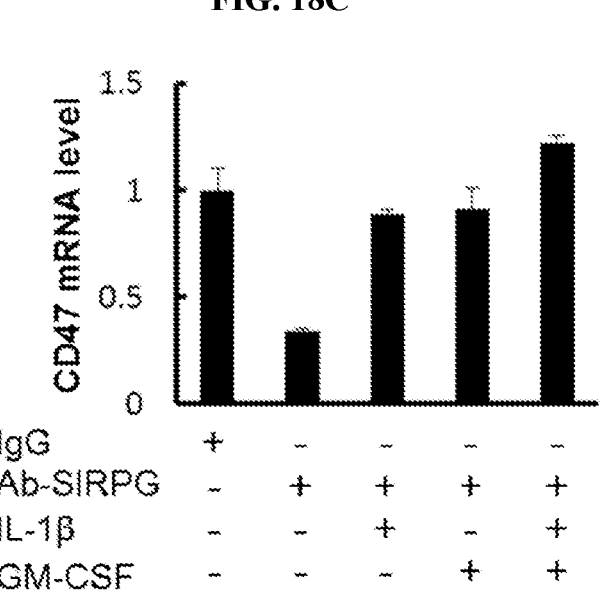
FIG. 18A-18E show the effect of an anti-SIRPgamma antibody treatment in vitro, according to some aspects of this disclosure. A549 cells were incubated with a control IgG, or an anti-SIRPgamma mAb LSB2.20. Protein lysates were prepared for Western immunoblot analysis as in FIG. 18A using antibodies specific to total MST1, LATS1, YAP1, or SOX2, or to the phosphorylated forms p-MST1, p-LATS1, and pYAP (P-Ser127). GAPDH served as a loading control.
Figures 18D, 18E:
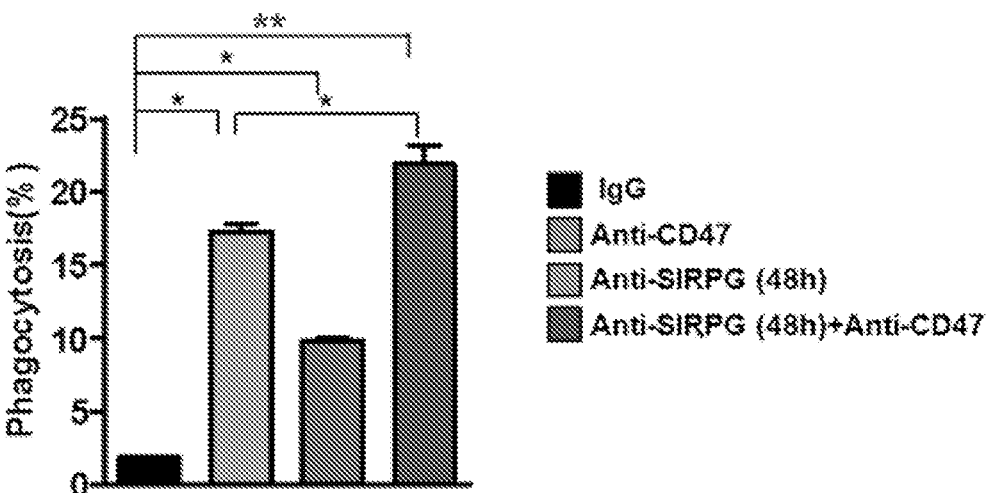

A549 cells were incubated with IgG, anti-SIRPalpha mAb, or anti-SIRPgamma mAb LSB2.20 at 4 µg/ml for 2 hours. Cells lysates were prepared as described in Example 1 and blotted with a panel of antibodies that are specific to phospho-LAST1, LAST1, phosphor-MST1, MST1, phosphor-YAP, YAP, SOX2, or GAPDH, respectively. Western blot experiments were performed as described in Example 1. Anti-SIRPgamma mAb LSB2.20 enhanced the phosphorylation of MST1, LATS1 and YAP, but suppressed Sox2, IL1B, GM-CSF and CD47 expression, indicating that LSB2.20 suppressed SIRPgamma signaling (FIG. 18A-18B). The inhibition of CD47 expression by LSB2.20 was restored by the cytokines IL1B, GM-CSF and the combination thereof (FIG. 18C). Importantly, LSB2.20 inhibited stem cell sphere formation and induced macrophage phagocytosis (FIG. 18E). All of these in vitro effects of LSB2.20 resembled those of SIRPgamma knockdown cells. Thus, LSB2.20 appears to be highly specific in targeting SIRPgamma. Notably, targeting SIRPgamma with LSB2.20 significantly enhanced the phagocytosis effect of the CD47 targeting antibody B6H12.2 antibody (FIG. 18E). This is not surprising because the CD47 antibody may not completely block all of the functions of CD47, and LSB2.20 could be further decreasing CD47 function by inhibiting SIRPgamma. These data demonstrate that LSB2.20 could efficiently target both CSCs and tumor immune evasion from macrophage phagocytosis.

Example 9. In Vivo Effect of an Anti-SIRPgamma Antibody

In this example, the effect of LSB2.20 in preclinical mouse models were investigated by inoculating nude mice with GFP-labeled A549 cells. 1×10e6 A549 monolayer cells were diluted in serum-free DMEM medium and injected subcutaneously to four-week-old male nude mice (n=5 each). Six days after inoculation, the mice were treated with an intraperitoneal injection of LSB2.20 every 2 days for 4 times (IgG 50 µg per dose; LSB2.20 25 µg per dose; 50 µg per dose; 100 µg per dose). These dosages translate into 1.19 mg/kg, 2.38 mg/kg, or 5 mg/kg assuming an average weight of 21 grams for the mice. The average weight of the mice was 21 grams. 5 weeks later, mice were sacrificed. A schematic of the treatment regimen is shown in FIG. 19A.

Following sacrifice, tumor xenografts were removed, tumor volume (TV) and tumor weight were measured as described above. LSB2.20 dramatically inhibited the xenograft size (volume) and weight in a dose-dependent manner, as shown in FIG. 19B and FIG. 19C, respectively.

Analysis of phagocytosis was also performed. Tumor tissues were harvested in PBS 1×, minced, and digested into a single cell suspension in a mixed solution containing collagenase type 1 and type 4 (1.5 mg/ml) in DMEM for 1.5 hr at 37° C. The suspension was filtered through a 70 µm-cell strainer and washed by DMEM for 3 times and then resuspended in cold flow buffer. Single-cell suspensions were incubated with PE-cy7 labeled rat anti-mouse CD11-b and APC labeled rat anti-mouse F4/80 under 4° C. for 30 minutes, then washed and re-suspended in cold flow buffer. Flow cytometric data were obtained using a FACS Calibur (BD Biosciences, USA) and analyzed with FlowJo software.

Quantitative real-time PCR (qRT-PCR) assays were also performed as follows: Total DNA was extracted from the tumor tissue cells using TIANamp Genomic DNA Kit (TIAN, China). qRT-PCR was performed using SYBR PrimeScript RT-PCR kit (TaKaRa, Japan) on a Rotor-Gene 6000 real-time genetic analyzer (Corbett Life Science, USA). Primers of target genes and the product sizes are listed in Table 2 (F=forward primers; R=reverse primers). Mouse DNA was amplified as an internal control. The PCR protocol included denaturation (95° C. for 2 min), followed by 40 cycles of amplification and quantification (95° C. for 5 s, 55° C.-57° C. for 30 seconds) and melting curve (55° C.-95° C., with 0.5° C. increment each cycle). Each sample was tested at least in triplicates.

TABLE 2 qRT-PCR primers

| Gene (Accession no.) | Primer sequence (5'→3') | SEQ ID NO: | Amplification size (bp) |
|---|---|---|---|
| GM-CSF | F: AAATGTTTGACCTCCAGGAGCC | 1 | 135 |
| NM_000758 | R: GAGGGCAGTGCTGCTTGTAG | 2 | |
| | | | |
| IL-10 | F: GAGCAACAAGTGGTGTTCTCC | 3 | 110 |
| NM_000576 | R: AACACGCAGGACAGGTACAG | 4 | |
| | | | |
| CD47 | F: GCGATTGGATTAACCTCCTTCGTCA | 5 | 113 |
| NM_001777 | R: CCATGCATTGGTATACACGCCGC | 6 | |
| | | | |
| SOX2 | F: CAGCCCATGCACCGCTACGACG | 7 | 147 |
| NM_003106 | R: CACCGAACCCATGGAGCCAAGAGC | 8 | |

Figure 19D:
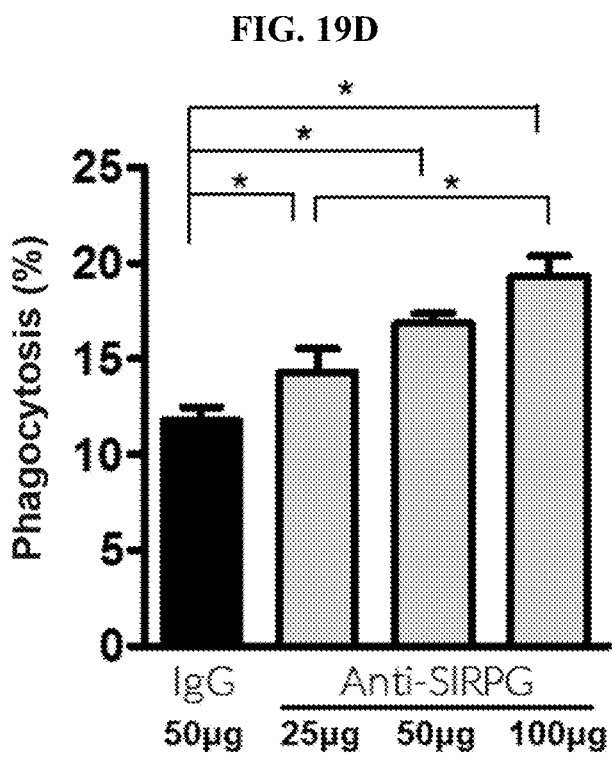
Figure 19E:
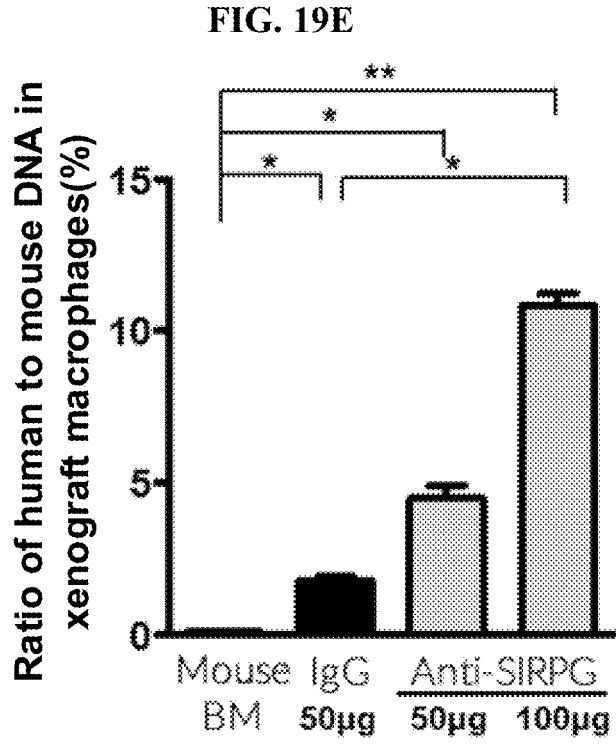

The percentage of F4/80+CD11b$^+$ macrophages containing phagocytosed GFP-labeled A549 cells showed that the LSB2.20 significantly enhanced the tumor cell phagocytosis by macrophages in the in vivo tumor model (FIG. 19D-19E). Macrophages from the mouse xenografts were sorted/isolated based on expression of F4/80 and CD11b using flow cytometry, and the DNA isolated. The amount of human and mouse DNA isolated from the macrophages was quantitated using qRT-PCR using primers for the human and mouse PTGER2 gene as shown in Table 3, and the ratio of human to mouse DNA was determined. The presence of human DNA present in the mouse macrophages reflected tumor cell phagocytosis. The xenograph macrophages from mice treated with the anti-SIRPgamma antibody had increased ratio of human to mouse DNA relative to controls (FIG. 19E), which is consistent with the phagocytosis data in FIG. 19D. Collectively, the results show that targeting SIRP-gamma with the anti-SIRPgamma neutralizing antibody LSB2.20 in vivo inhibits tumor growth and enhances phagocytosis of cancer cells by macrophages.

TABLE 3

Human and mouse specific primers for qRT-PCR

| Gene | Primer sequence (5'→3') | SEQ ID NO: | Amplification size (bp) |
|---|---|---|---|
| HUMAN | F: GCTGCTTCTCATTGTCTCGG | 9 | 189 |
| PTGER2 | R: GCCAGGAGAATGAGGTGGTC | 10 | |
| | | | |
| MOUSE | F: CCTGCTGCTTATCGTGGCTG | 11 | 186 |
| PTGER2 | R: GCCAGGAGAATGAGGTGGTC | 12 | |

All patents, patent publications, patent applications, journal articles, books, technical references, and the like discussed in the instant disclosure are incorporated herein by reference in their entirety for all purposes.

It is to be understood that the figures and descriptions of the invention have been simplified to illustrate elements that are relevant for a clear understanding of the invention. It should be appreciated that the figures are presented for illustrative purposes and not as construction drawings. Omitted details and modifications or alternative embodiments are within the purview of persons of ordinary skill in the art.

It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

What is claimed:

1. A method of treating a subject with cancer, the method comprising administering to the subject a pharmaceutically effective amount of a composition comprising a signal-regulatory protein gamma (SIRPgamma) targeted antibody.

2. The method of claim 1, wherein the SIRPgamma targeted antibody is a monoclonal antibody.

3. The method of claim 1, wherein the SIRPgamma targeted antibody is a humanized antibody.

4. The method of claim 1, wherein the SIRPgamma targeted antibody comprises a humanized antibody corresponding to any one of antibody LSB2.20 (RRID: AB_1227766), antibody OX119, antibody AF4486, or antibody PA5-47627.

5. The method of claim 1, wherein the composition further comprises a pharmaceutically acceptable carrier.

6. The method of claim 1, wherein the cancer comprises at least one of lung cancer, colorectal cancer, breast cancer, prostate cancer, ovarian cancer, cervical cancer, a sarcoma, skin cancer, testicular cancer, renal cancer, brain cancer, or leukemia.

7. The method of claim 6, wherein the lung cancer comprises bronchogenic cancer, squamous cell carcinoma, small cell lung cancer, adenocarcinoma, or undifferentiated large cell lung cancer.

8. The method of claim 1, wherein the method further comprises administering a second form of cancer therapy to the subject.

9. The method of claim 8, wherein the second form of cancer therapy comprises a cytotoxic agent, a chemotherapeutic agent, an immunosuppressive agent, or radiation therapy.

10. The method of claim 8, wherein the second form of cancer therapy comprises a PDL-1 inhibitor, a PD-1 inhibitor, or a CTLA4 inhibitor.

11. The method of claim 10, wherein the PDL-1 inhibitor, the PD-1 inhibitor, or the CTLA4 inhibitor is an inhibitory antibody.

12. The method of claim 8, wherein the second form of cancer therapy comprises an epidermal growth factor receptor (EGFR) inhibitor.

13. The method of claim 12, wherein the EGFR inhibitor is a receptor tyrosine kinase inhibitor.

* * * * *

SEQUENCE LISTING

```
<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic primer"

<400> SEQUENCE: 1
aaatgtttga cctccaggag cc                                              22

<210> SEQ ID NO 2
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
gagggcagtg ctgcttgtag                                                 20

<210> SEQ ID NO 3
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 3
gagcaacaag tggtgttctc c                                               21

<210> SEQ ID NO 4
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
aacacgcagg acaggtacag                                                 20

<210> SEQ ID NO 5
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
gcgattggat taacctcctt cgtca                                           25

<210> SEQ ID NO 6
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
ccatgcattg gtatacacgc cgc                                             23

<210> SEQ ID NO 7
<211> LENGTH: 22

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
cagcccatgc accgctacga cg                                          22

<210> SEQ ID NO 8
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 8
caccgaaccc atggagccaa gagc                                        24

<210> SEQ ID NO 9
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 9
gctgcttctc attgtctcgg                                             20

<210> SEQ ID NO 10
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
gccaggagaa tgaggtggtc                                             20

<210> SEQ ID NO 11
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 11
cctgctgctt atcgtggctg                                             20

<210> SEQ ID NO 12
<211> LENGTH: 20
<212> TYPE: DNA
<213> ORGANISM: Artificial Sequence
<220> FEATURE:
```

-continued

```
<221> NAME/KEY: source
<223> OTHER INFORMATION: /note="Description of Artificial Sequence:
      Synthetic primer"

<400> SEQUENCE: 12
gccaggagaa tgaggtggtc                                                    20
```